(12) United States Patent
Cho

(10) Patent No.: US 11,498,042 B2
(45) Date of Patent: Nov. 15, 2022

(54) METHOD FOR THE PRODUCTION OF MICROGEL BUILDING BLOCKS FROM POLLEN

(71) Applicant: NANYANG TECHNOLOGICAL UNIVERSITY, Singapore (SG)

(72) Inventor: Nam-Joon Cho, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 71 days.

(21) Appl. No.: 16/965,425

(22) PCT Filed: Jan. 29, 2019

(86) PCT No.: PCT/SG2019/050045
§ 371 (c)(1),
(2) Date: Jul. 28, 2020

(87) PCT Pub. No.: WO2019/147190
PCT Pub. Date: Aug. 1, 2019

(65) Prior Publication Data
US 2021/0077969 A1 Mar. 18, 2021

(30) Foreign Application Priority Data

Jan. 29, 2018 (SG) .......................... 10201800742R

(51) Int. Cl.
| | | |
|---|---|---|
| A61K 8/9783 | (2017.01) | |
| B01J 13/00 | (2006.01) | |
| A61K 8/04 | (2006.01) | |
| A61K 8/11 | (2006.01) | |
| A61K 9/06 | (2006.01) | |
| A61K 9/50 | (2006.01) | |
| C09D 11/02 | (2014.01) | |
| C12N 5/00 | (2006.01) | |

(52) U.S. Cl.
CPC .......... *B01J 13/0065* (2013.01); *A61K 8/042* (2013.01); *A61K 8/11* (2013.01); *A61K 8/9783* (2017.08); *A61K 9/06* (2013.01); *A61K 9/5063* (2013.01); *C09D 11/02* (2013.01); *C12N 5/0068* (2013.01); *A61K 2800/10* (2013.01); *C12N 2533/90* (2013.01)

(58) Field of Classification Search
None
See application file for complete search history.

(56) References Cited

U.S. PATENT DOCUMENTS

| 7,449,501 B2 | 11/2008 | Uerz et al. |
| 2018/0092852 A1 | 4/2018 | Gill et al. |

FOREIGN PATENT DOCUMENTS

| CN | 104941544 A | 9/2015 |
| JP | 2002-284926 A | 10/2002 |

OTHER PUBLICATIONS

C. Pöhlker, J. A. Huffman, J.-D. Förster, U. Pöschl, Autofluorescence of atmospheric bioaerosols: spectral fingerprints and taxonomic trends of pollen. Atmospheric Measurement Techniques 6, 3369-3392 (2013).
R. Skouri, F. Schosseler, J. P. Munch, S. J. Candau, Swelling and Elastic Properties of Polyelectrolyte Gels. Macromolecules 28, 197-210 (1995).
S. K. De et al., Equilibrium swelling and kinetics of pH-responsive hydrogels: models, experiments, and simulations. Journal of Microelectromechanical Systems 11, 544-555 (2002).
Q. Pu, K. Sarkanen, Donnan Equilibria in Wood-Alkali Interactions. Part 1. Quantitative Determination of Carboxyl-, Carboxyl Ester and Phenolic Hydroxyl Groups. Journal of Wood Chemistry and Technology 9, 293-312 (1989).
Sollich et al. ("Soft glassy rheology." in Molecular Gels, pp. 161-192. Springer, Dordrecht, 2006).
Mundargi, R. C. et al., Extraction of sporopollenin exine capsules from sunflower pollen grains. RSC Adv., Feb. 9, 2016, vol. 6. No. 20, pp. 16533-16539.
Gan, T. et al., Thermogelable PNIPAM microgel dispersion as 3D cell scaffold: effect of syneresis. J. Mater. Chem., Jun. 14, 2010, vol. 20, No. 28, pp. 5937-5944.
O'Bryan, C.S. et al., Self-assembled micro-organogels for 3D printing silicone structures. *Sci. Adv.*, May 10, 2017, vol. 3, No. 5, pp. 1-8.
J. M. Tylianakis, the global plight of pollinators. *Science* 339, 1532-1533 (2013).
T. Ariizumi, K. Toriyama, Genetic regulation of sporopollenin synthesis and pollen exine development. *Annual review of plant biology* 62, 437-460 (2011).
G. Mackenzie, A. N. Boa, A. Diego-Taboada, S. L. Atkin, T. Sathyapalan, Sporopollenin, the least known yet toughest natural biopolymer. Frontiers in Materials 2, 66 (2015).
M. B. Davis, R. G. Shaw, Range shifts and adaptive responses to Quaternary climate change. Science 292, 673-679 (2001).
V. M, Bryant, G. D. Jones, Forensic palynology: Current status of a rarely used technique in the United States of America. Forensic Science International 163, 183-197 (2006).
J. F. van Leeuwen et al., Fossil pollen as a guide to conservation in the Galápagos. Science 322, 1206 (2008).
I. J. Gomez et al., Three-dimensional magnetite replicas of pollen particles with tailorable and predictable multimodal adhesion. Journal of Materials Chemistry C 3, 632-643 (2015).

(Continued)

*Primary Examiner* — Jessica Worsham
(74) *Attorney, Agent, or Firm* — Alston & Bird LLP

(57) ABSTRACT

A new type of biomaterial that can be generated from pollen, methods for its production, the various uses thereof in, for example, biological, medicinal, cosmetic, nutritional and printing applications and the materials/devices that comprise this new material are provided. The biomaterial comprises microgels of sporoderm polymer complex microcapsules (SPC-MCs), produced by deproteinizing the pollen from eudicot plants, in particular of genus *Baccharis*, *Helianthus* or *Camellia*, by contacting it with an aqueous base solution at elevated temperatures for up to 10 hours to obtain porous SPC-MCs, and hydrolytically degrading the SPC-MCs by contacting it with an aqueous base solution for periods up to 60 days to obtain microgels of SPC-MCs.

11 Claims, 30 Drawing Sheets

(56) References Cited

OTHER PUBLICATIONS

O. O. Fadiran, N. Girouard, J. C. Meredith, Pollen fillers for reinforcing and strengthening of epoxy composites. Emergent Materials, 1-9 (2018).

M. G. Potroz et al., Plant-Based Hollow Microcapsules for Oral Delivery Applications: Toward Optimized Loading and Controlled Release. Advanced Functional Materials 27, 1700270 (2017).

A. Diego-Taboada, S. T. Beckett, S. L. Atkin, G. Mackenzie, Hollow pollen shells to enhance drug delivery. Pharmaceutics 6, 80-96 (2014).

R. C. Mundargi et al., Eco-friendly streamlined process for sporopollenin exine capsule extraction. Scientific reports 6, 19960 (2016).

P. Gonzalez Cruz, M. J. Uddin, S. U. Atwe, N. Abidi, H. S. Gill, Chemical treatment method for obtaining clean and intact pollen shells of different species. ACS Biomaterials Science & Engineering, (2018).

F. W. Gibbs, the history of the manufacture of soap. Annals of Science 4, 169-190 (1939).

E. Katifori, S. Alben, E. Cerda, D. R. Nelson, J. Dumais, Foldable structures and the natural design of pollen grains. Proceedings of the National Academy of Sciences 107, 7635-7639 (2010).

J. Rieka, T. Tanaka, Swelling of ionic gels: quantitative performance of the Donnan theory. Macromolecules 17, 2916-2921 (1984).

A. Drozdov, J. deClaville Christiansen, Modeling the effects of pH and ionic strength on swelling of polyelectrolyte gels. The Journal of chemical physics 142, 114904 (2015).

B. R. Saunders et al., Microgels: From responsive polymer colloids to biomaterials. Advances in colloid and interface science 147, 251-262 (2009).

D. R. Griffin, W. M. Weaver, P. O. Scumpia, D. Di Carlo, T. Segura, Accelerated wound healing by injectable microporous gel scaffolds assembled from annealed building blocks. Nature Materials 14, 737 (2015).

A. S. Mao et al., Deterministic encapsulation of single cells in thin tunable microgels for niche modelling and therapeutic delivery. Nature Materials 16, 236 (2017).

L. A. Goetz, B. Jalvo, R. Rosal, A. P. Mathew, Superhydrophilic anti-fouling electrospun cellulose acetate membranes coated with chitin nanocrystals for water filtration. Journal of Membrane Science 510, 238-248 (2016).

H. Zhang et al., Aligned two- and three-dimensional structures by directional freezing of polymers and nanoparticles. Nature Materials 4, 787-793 (2005).

W. S. Judd, R. G. Olmstead, a survey of tricolpate (eudicot) phylogenetic relationships. American Journal of Botany 91, 1627-1644 (2004).

F. J. Martin-Martinez, K. Jin, D. López Barreiro, M. J. Buehler, the Rise of Hierarchical Nanostructured Materials from Renewable Sources: Learning from Nature. ACS Nano, (2018).

J. Song et al., Processing bulk natural wood into a high-performance structural material. Nature 554, 224 (2018).

J. Aguílera, M. Karel, Preservation of biological materials undec desiccation. Critical Reviews in Food Science & Nutrition 37, 287-309 (1997).

C. M. Yakacki, S. Willis, C. Luders, K. Gall, Deformation Limits in Shape-Memory Polymers. Advanced Engineering Materials 10, 112-119 (2008).

T. J Young et al., The use of the PeakForceTM quantitative nanomechanical mapping AFM-based method for high-resolution Young's modulus measurement of polymers. Measurement Science and Technology 22, 125703 (2011).

A

B

C

D

E

F

G

H

D

E

B

C

METHOD FOR THE PRODUCTION OF MICROGEL BUILDING BLOCKS FROM POLLEN

CROSS-REFERENCE TO RELATED APPLICATION APPLICATIONS

The present application is a national phase entry of PCT/SG2019/050045, filed on Jan. 29, 2019, which claims the benefit of priority of Singapore Patent Application No. 10201800742R filed on 29 Jan. 2018, the content of which is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates generally to a new type of biomaterial that can be generated from pollen, methods for its production, the various uses thereof in, for example, biological, medicinal, cosmetic and nutritional applications and the materials/devices that comprise this new material.

BACKGROUND OF THE INVENTION

Pollen plays a critical role in plant reproduction, transferring cellular material between different reproductive parts of plants. Plants have evolved mechanisms to renewably produce pollen grains in large quantities, and the fidelity of these biosynthetic mechanisms is remarkably high. For each plant species, a particular type of pollen grain is produced that is composed of a hollow microcapsule structure with uniform size and function-driven shape and ornamental architecture. In all cases, the microcapsule structures possess a strong outer layer that is composed of sporopollenin, which is a crosslinked biopolymer comprising fatty acid, phenylpropanoid and phenolic components. Often regarded as the diamond of biopolymers, sporopollenin imparts extreme durability, mechanical strength and chemical stability to pollen grains. Such properties have led pollen to be regarded as practically indestructible and pollen is widely used as stable, content-rich markers for archaeological, ecological and forensics applications.

In nature, pollen shells have evolved not only to be the first defensive line in a quiescent, dehydrated state, to protect internal microgametophytes during indeterminate periods, but also to be a dynamic "smart" carrier in a responsive, rehydrated state, to transfer the haploid male genetic materials to a receptive stigma during pollination. Constitutive materials and nano-/microstructures of the pollen shell facilitate large volume changes of its pollen grain, particularly for harmomegathy, a self-defensive and environment-responsive process to maintain the internal moisture in arid environments by closing off the apertures of the shell. This phenomenon has long been mysterious until recently it has been evidenced as dynamic gelation of pollen grains, in which pectin acts like "valves" for water entry, enabling a regulated process of water uptake into the dehydrated pollen grain.

Sporopollenin-based sporoderms form the outer shell wall in a wide range of pollens (pollen grains) and plant spores so as to protect sensitive genetic material from harsh environmental conditions. The sporoderm polymer complex (SPC) typically comprises sporopollenin as an outermost layer (exospore or exine) with cellulose, hemicellulose, and pectin as an inner layer (so-called intine). The exine layer is often intricately sculptured in species-specific patterns, allowing material recovered from (for example) lake sediments to provide useful information to palynologists about plant and fungal populations in the past. The intine layer is located on the inside of the exine and adjacent to the pollen plasma membrane. The intine layer consists of two separate layers, the granular exintine with pectine and protein inclusions facing the exterior, and a microfibrillar cellulosic endintine facing the interior. The pectin network is known to interact with the cellulose network through both covalent ester linkages and non-covalent hydrogen bonding. Similar to pectinase, the treatment with strong alkali (potassium hydroxide; KOH) at high temperature (80° C.) de-esterifies pectin through an alkaline hydrolysis reaction, increasing water absorption capability due to the resultant gelation. Besides the influence on pectin, strong alkali not only disrupts hydrogen bonding between hemicellulose and cellulose microfibrils or between pectin and cellulose microfibrils, but also degrades pectin and cellulose molecules along with the increased duration of alkali treatment, ultimately leading to softening of intine. As a result, pollen transforms from the close state (or termed as "off") to the open state (or termed as "on") due to opening of apertures which are the weakest spots of the pollen surface, providing the main route for uptake of water and nutrients from the environments and serving as the exit point of a pollen tube.

There has been growing interest to explore pollen for materials science applications, including as templates for materials fabrication, structural reinforcements for composite materials and drug delivery vehicles among other possibilities. A key advantage is that pollen is readily obtainable from numerous plant sources at low cost and can be processed into isolated capsules. Defatted pollen grains, or more commonly extracted sporopollenin shells, are the main types of pollen-derived materials that have been used for microencapsulation and drug delivery applications.

However, the extremely high stability of sporopollenin has resulted in this remarkable material being largely overlooked in the fields of fundamental and applied materials science.

While it is known in the art to use acid/base processing strategies to produce pollen-derived capsules from pollen grains to remove sensitive biological materials such as proteins, polysaccharides and nucleic acids while preserving the physical and chemical properties of the sporopollenin shell, the present invention is based on the inventors' surprising identification of a one-pot processing strategy that challenges the prevailing notion that pollen is practically indestructible and structurally immutable. When pollen from sunflower plants (*Helianthus annuus*) was incubated in alkaline conditions for extended periods of time (a simple process replicating the basic step of soapmaking), it was discovered that the hard pollen grains were transformed into pliable, soft microgel particles. In marked contrast to the pollen precursors, the alkaline-treated microgel building blocks could be assembled into two-dimensional sheets and three-dimensional sponges, opening the door to an entirely new class of naturally sourced, bioinspired materials with advantageous properties. In addition, they could be directly applied to three-dimensional (3D) printing systems as either a "write-in" supporting matrix or a "write-out" smart material ink component.

To date, there have been no references to sporopollenin being dissolved, oxidized, and degraded/eroded under any chemical conditions except human fluid (e.g. specific enzyme or blood for partial degradation/erosion). Specifically, there have been no studies specifically exploring the base-hydrolysis degradation and gelation process of sporopollenin and no reports of strategies to design functional materials from pollen-based materials.

SUMMARY OF THE INVENTION

The present invention changes this by providing, in a first aspect, a method for the formation of microgels of sporoderm polymer complex microcapsules (SPC-MCs), and the method is comprised of the following steps:

(a) providing pollen grains from eudicot plants;

(b) deproteinizing the pollen by contacting it with an aqueous base solution at elevated temperatures for up to 10 hours to obtain porous SPC-MCs;

(c) hydrolytically degrading the SPC-MCs by contacting it with an aqueous base solution for periods up to 60 days to obtain microgels of SPC-MCs.

In these methods, the pollen may originate from a flowering plant of the genus *Baccharis*, *Helianthus* or *Camellia*, more preferably *Helianthus annuus*.

In various embodiments of the inventive methods, the pollen used is either defatted pollen or the method further includes a step of defatting the pollen prior to step (b), optionally by treatment with an organic solvent, such as, without limitation, acetone. Irrespective of whether the pollen is defatted or not, it may be used in dry form for step (b).

The aqueous base solution used in step (b) and/or (c) may, in various embodiments of the invention, comprise, consist essentially of or consist of an aqueous alkaline metal hydroxide solution, preferably potassium hydroxide (KOH) or sodium hydroxide (NaOH) solution, more preferably KOH solution. In these solutions, the alkaline metal hydroxide concentration may range from about 0.5 to about 40% (w/v), preferably from 1 to 25% (w/v) relative to the total volume of the solution.

In various embodiments, step (b) is carried out at a temperature of 40 to 95° C., preferably 60 to 90° C., more preferably 70 to 85° C. and/or for a period of 1 to 6 hours, preferably 2 to 4 hours.

Step (c) may be carried out at a temperature of 10 to 30° C., preferably 15 to 25° C., and/or wherein step (c) is carried out for 7 to 35 days, preferably 14 to 28 days.

In various embodiments, step (c) further includes a step of neutralizing the suspension of partially degraded SPC-MCs after the hydrolytic degradation by washing the partially degraded SPC-MCs with water until the suspension has a pH in the range of 6.0 to 8.5, preferably in the range of 6.5 to 8.0, more preferably in the range of 7.0 to 7.5, to obtain a neutralized microgel solution.

The microgel obtained may typically be a viscous aqueous gel comprising 1 to 6 wt.-% SPC-MCs and the remainder being water.

In a second aspect, the invention also encompasses a microgel comprising SPC-MCs obtainable by a method according to the invention.

In a still further aspect, the invention features a method for the formation of flexible sheets or sponge structures, comprising the steps of forming microgels of sporoderm polymer complex microcapsules (SPC-MCs) according to the method of the invention and further comprising the steps of (d) forming a film of the microgel on a substrate and drying the film to obtain a flexible sheet of SPC-MCs; or (e) lyophilizing the microgel to obtain sponge structures of SPC-MCs.

Flexible sheets or sponges comprising SPC-MCs obtainable by the method described herein also form part of the invention.

Another aspect is directed to a composition comprising the microgel or the flexible sheets or sponges according to the invention, wherein the composition is a cosmetic, nutritional or pharmaceutical composition. Alternatively, the composition may be a printing composition, such as a composition for 3D printing or a printing ink composition.

The microgels of the invention may, for example, be used as a thickener or gelling agent for cosmetic or food compositions. Also contemplated is their use in 3D printing and ink compositions. Alternatively, the microgels, flexible sheets or sponges may be used as scaffolds for cells, for example in cell culture or medicinal applications, for example to stimulate cell proliferation.

A still further use of the microgel, the flexible sheets or sponges is in the delivery of an active agent, wherein said active agent is preferably encapsulated in the SPC-MCs. The active agent may be a pharmaceutically or cosmetically active agent or a cosmetic or pharmaceutical composition.

A still further aspect relates to a method for promoting cell proliferation comprising (a) contacting cells with a sheet or sponge according to the invention; and (b) culturing said cells in the presence of said sheet of sponge as a scaffold under suitable culturing conditions.

Further encompassed is a method for the delivery of a pharmaceutically or cosmetically active agent, comprising providing a composition comprising the microgel or the flexible sheets or sponges of the invention, the microgel, flexible sheets or sponges comprising the pharmaceutically or cosmetically active agent encapsulated in the SPC-MCs, and administering a pharmaceutically or cosmetically active amount of the composition to a subject.

In the following the invention will be described in greater detail by reference to the accompanying drawings and examples.

BRIEF DESCRIPTION OF THE DRAWINGS

The invention will be better understood with reference to the detailed description when considered in conjunction with the non-limiting examples and the accompanying drawings.

Figure 16:
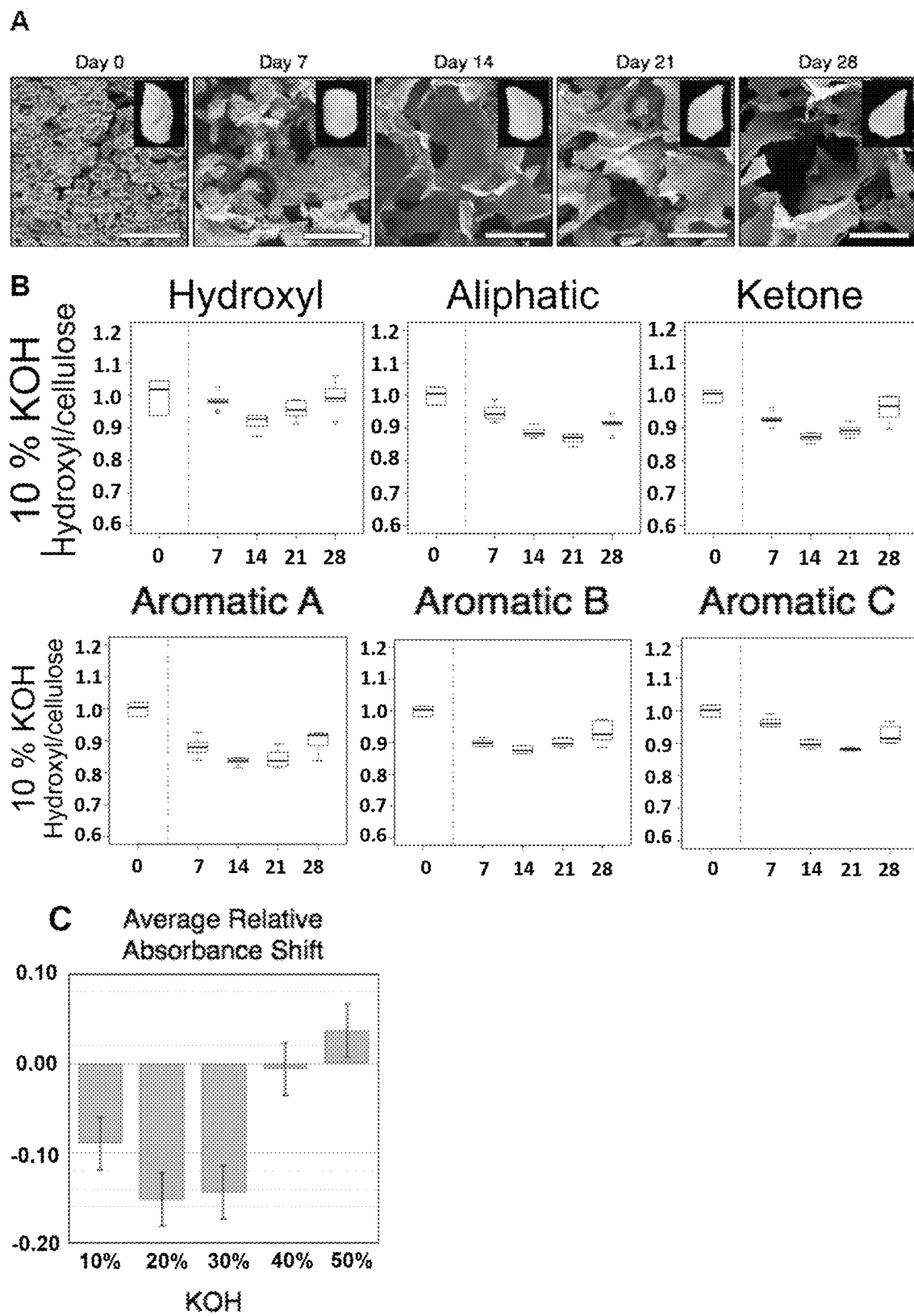
FIG. 16. Porous sponge-like structures form when SPC-microgel systems are frozen and lyophilized (FIG. 16A).
Figure 16:
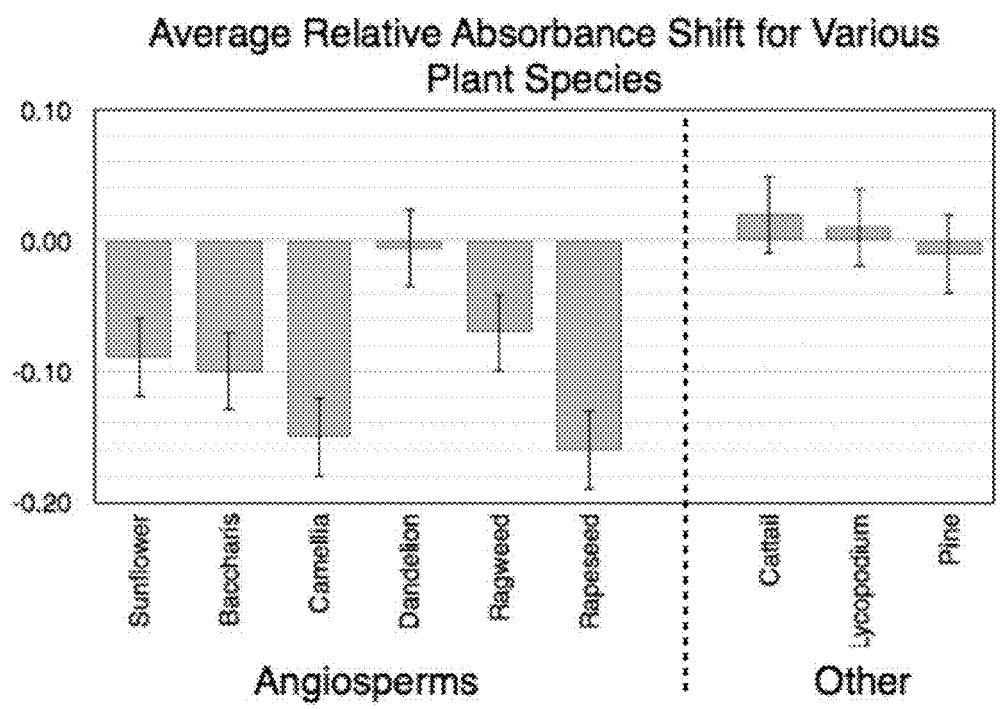
Figure 16:
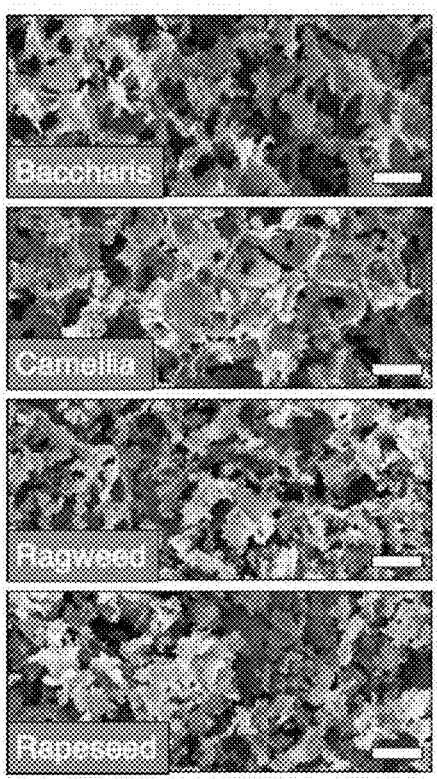
Figure 16:
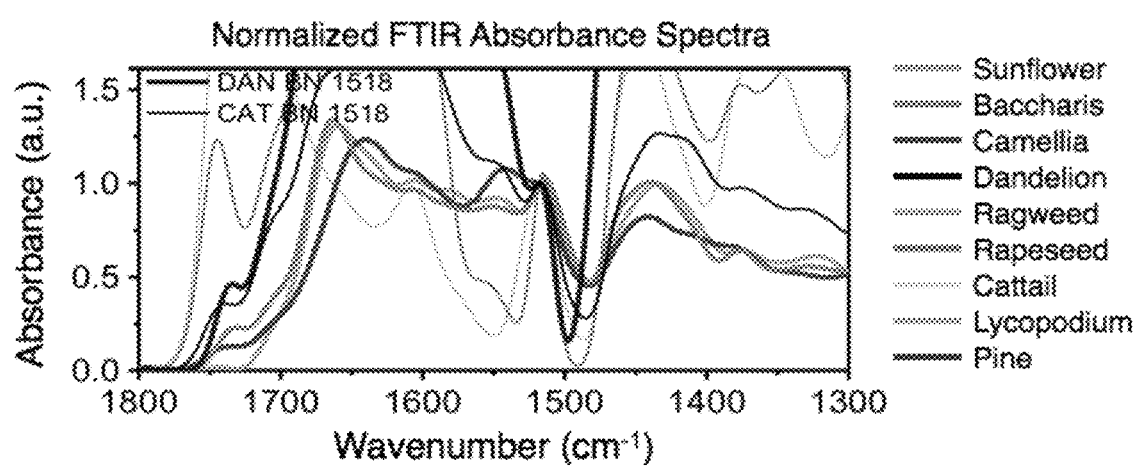

Pollen particle morphology reduces from day 0 to day 14 where upon smooth pore walls are formed and sponge morphology remains similar for days 21 and 28. Lyophilized SPC-microgel samples were analyzed by ATR-FTIR to determine general trends in SPC bond degradation. Peak height ratio analysis of ATR-FTIR data identified relative decreases in molecular bond proportions from day 0 to day 14, with stabilization and increases at days 21 and 28 for all major peaks (FIG. 16B). Height ratios were taken relative to the most stable spectra peak, being 1062 cm$^{-1}$ for *H. annuus* under 10% KOH solution conditions and attributable to α-cellulosic compounds. This trend supports the overall degradation of SPC up to day 14 followed by SPC restructuring. Averaging total shifts in relative peak height proportions across all incubation periods and major peaks for each of 10%, 20%, 30%, 40%, and 50% KOH$_{aq}$ processing conditions indicates increased total reductions from 10% to 30% KOH$_{aq}$ with decreased reductions at 40% and inhibition at 50% KOH$_{aq}$ (FIG. 16C). This trend indicates an alkaline assisted hydrolytic degradation process. Increasing concentrations of aqueous alkaline solutions has been shown to inhibit degradation in polymer systems due to a lack of bulk water phase H$_2$O molecules required for hydrolysis. Analysis of lyophilized SPC-microgels. The generality of alkaline assisted hydrolytic degradation for various SPC sources was explored with 10% KOH$_{aq}$ for an additional 9 plant species, comprising 5 angiosperms: *Baccharis; Camellia*; dandelion; ragweed; and rapeseed, and 3 non-angiosperms commonly studied in sporopollenin research literature: cattail; *Lycopodium*; and pine. Four of the five additional angiosperms exhibit ATR-FTIR peak height degradation trends similar to sunflower (FIG. 16D) and result in the formation of porous sponge materials upon gelation, freezing, and lyophilization (FIG. 16E). One angiosperm and the 3 non-angiosperm sourced pollens indicated no significant major peak degradation from FTIR analysis, and upon processing resulted in a powdery discrete particle agglomeration rather than a stable porous sponge.

Figure 17:
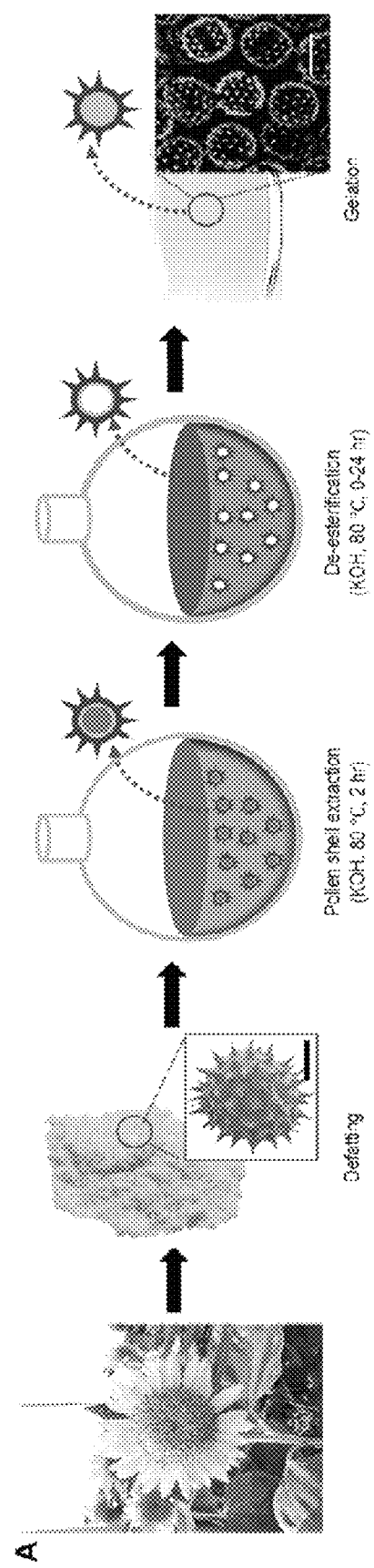
Figure 17:
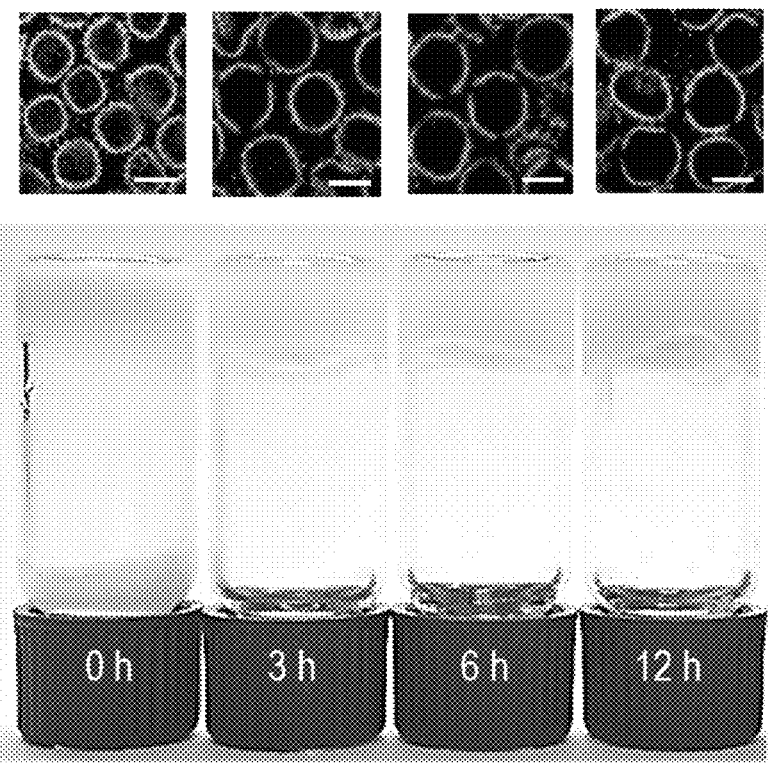
Figure 17:
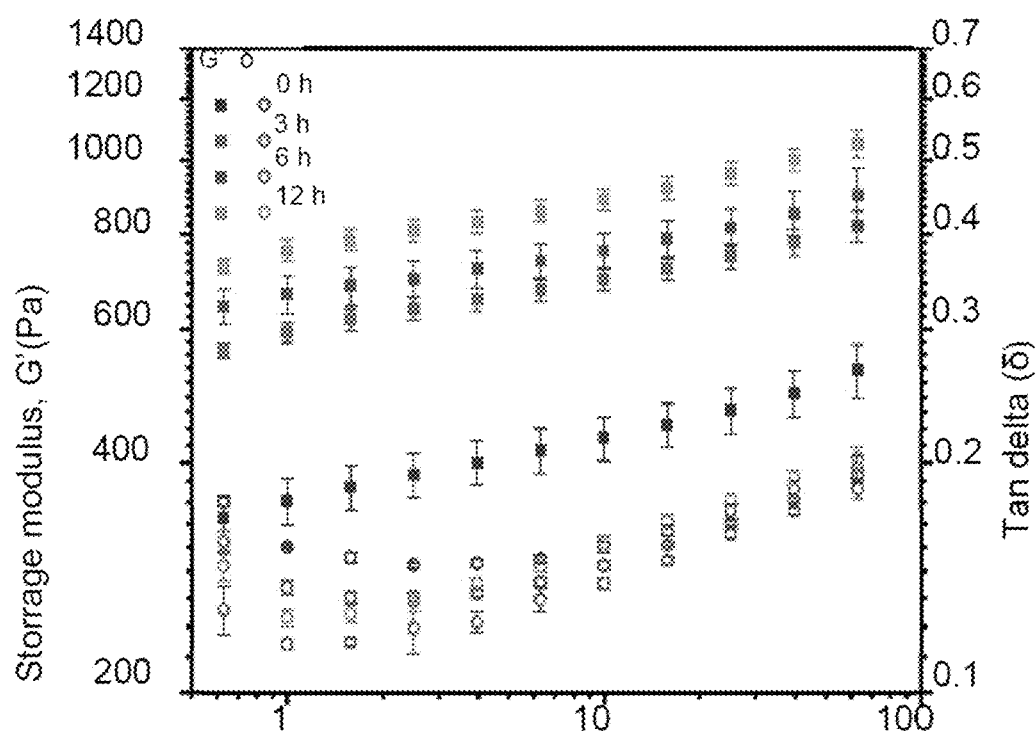
Figure 17:
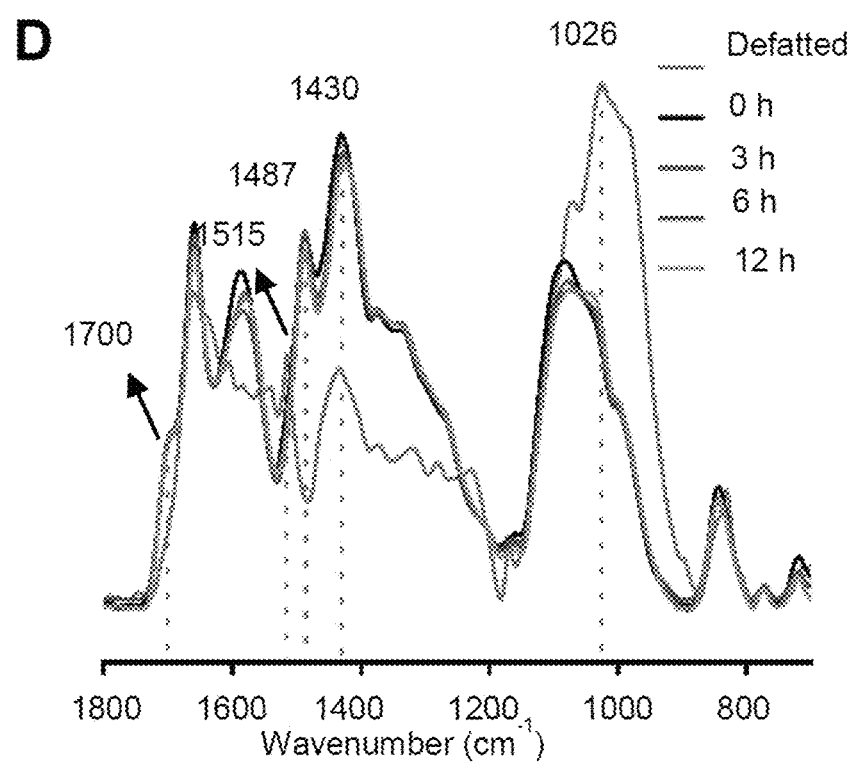

FIG. 17. Development of pollen microgels inspired by nature. A. Schematic of pollen grains with aperture opening mechanisms through gelation of pectin in intine. B. Schematics of the fabrication process of pollen microgels. Step 1. hard pollen grains are harvested from sunflower; Step 2. treatment with organic solvents for the removal of excess lipid coating ("defatting"); Step 3. incubation of hard pollen grains in strong alkaline (KOH) solution for 2 hrs at 80° C. ("Pollen shell extraction), Step 4. extended incubation in strong alkaline (KOH) solution at 80° C. for up to 24 hrs ("De-esterification"). This step involves de-esterification of methyl acetate in pectin; Step 5, neutralization and gelation of pollen microgels with deionized water. Scale bars for defatted pollen, 10 μm and for pollen microgels, 30 μm. C. Optical images of pollen microgel dispersion in inverted vials with various de-esterification time. D. 2D CLSM images of pollen microgels. The white arrows indicate aperture opening of pollen microgels. All scale bars, 30 μm. E-G. Size distribution (E), FT-IR spectra (F) and rheological behavior (G) of pollen microgel dispersion depending on de-esterification times.

Figure 18:
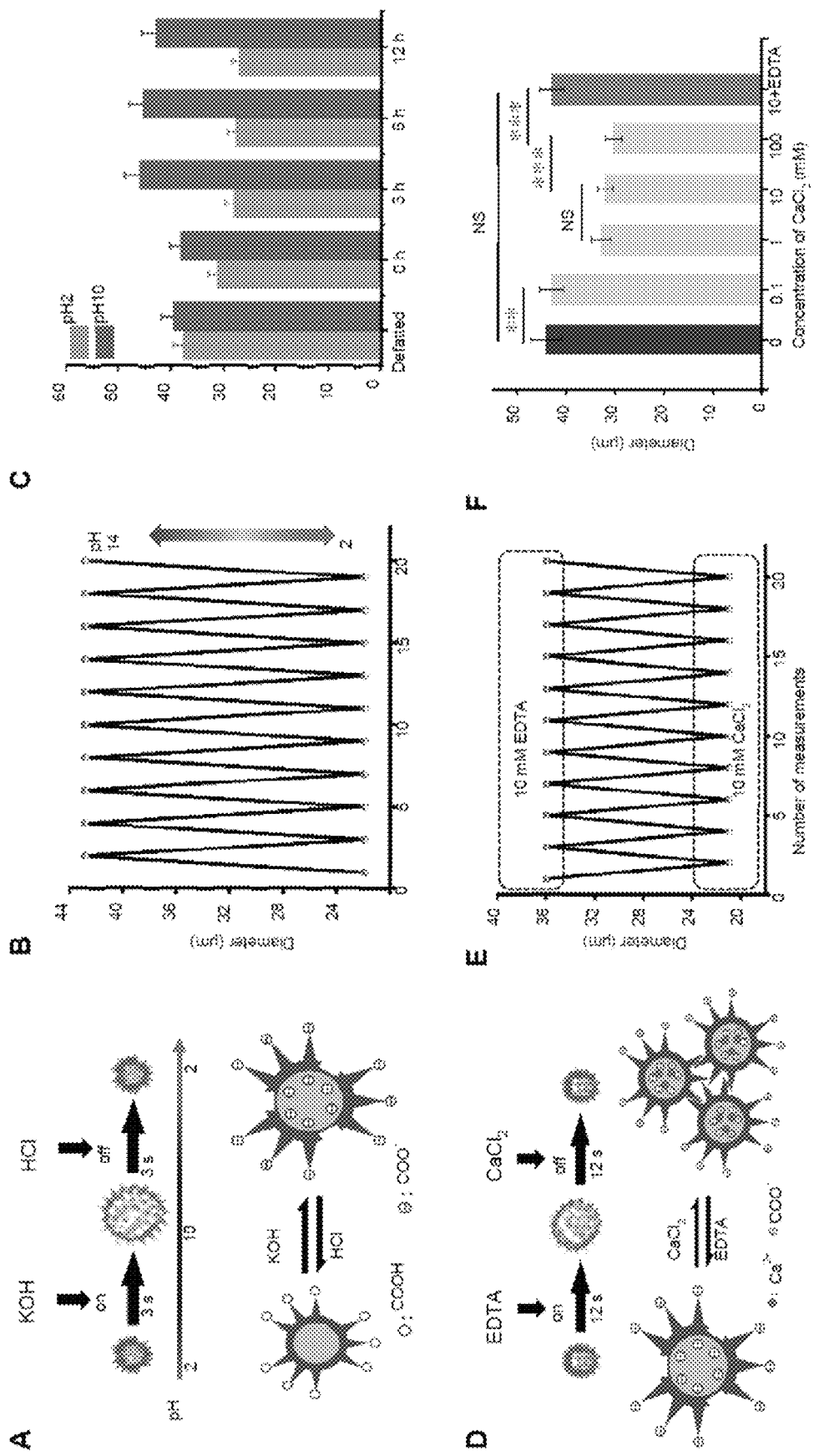

FIG. 18. Stimulus-responsive mechanisms of pollen microgels associated with pectin. A. Time-lapsed optical micrographs of individual pollen microgels (3 hr deesterification time) in aqueous solution with the solution pH changed from pH 10 to pH 2 and then pH 10. Depending on pH, association and de-association of protons in carboxyl groups of pectin lead de-swelling and swelling of microgels in response to pH change. B. Repeatability of pH-responsive behavior of pollen microgels (up to 20 cycles). C. pH responsive swelling and deswelling equilibrium diameters of pollen microgels with various deesterification times. D. Time-lapsed optical micrographs of individual pollen microgels (3 hr deesterification time) in aqueous solution with the sequential treatment of calcium chloride and EDTA solution. Ca ion-induced physical crosslinking of pectin increases crosslinking density of the network, decreasing swelling diameter of pollen microgels. With EDTA chelating, the crosslinking density decreases again with restored swellability. E. Repeatability of Ca$^{2+}$/EDTA-responsive behavior of pollen microgels (up to 20 cycles). F. Ca$^{2+}$/EDTA-responsive swelling and deswelling equilibrium diameters of pollen microgels with various deesterification times. All scale bars, 50 μm.

Figure 19:
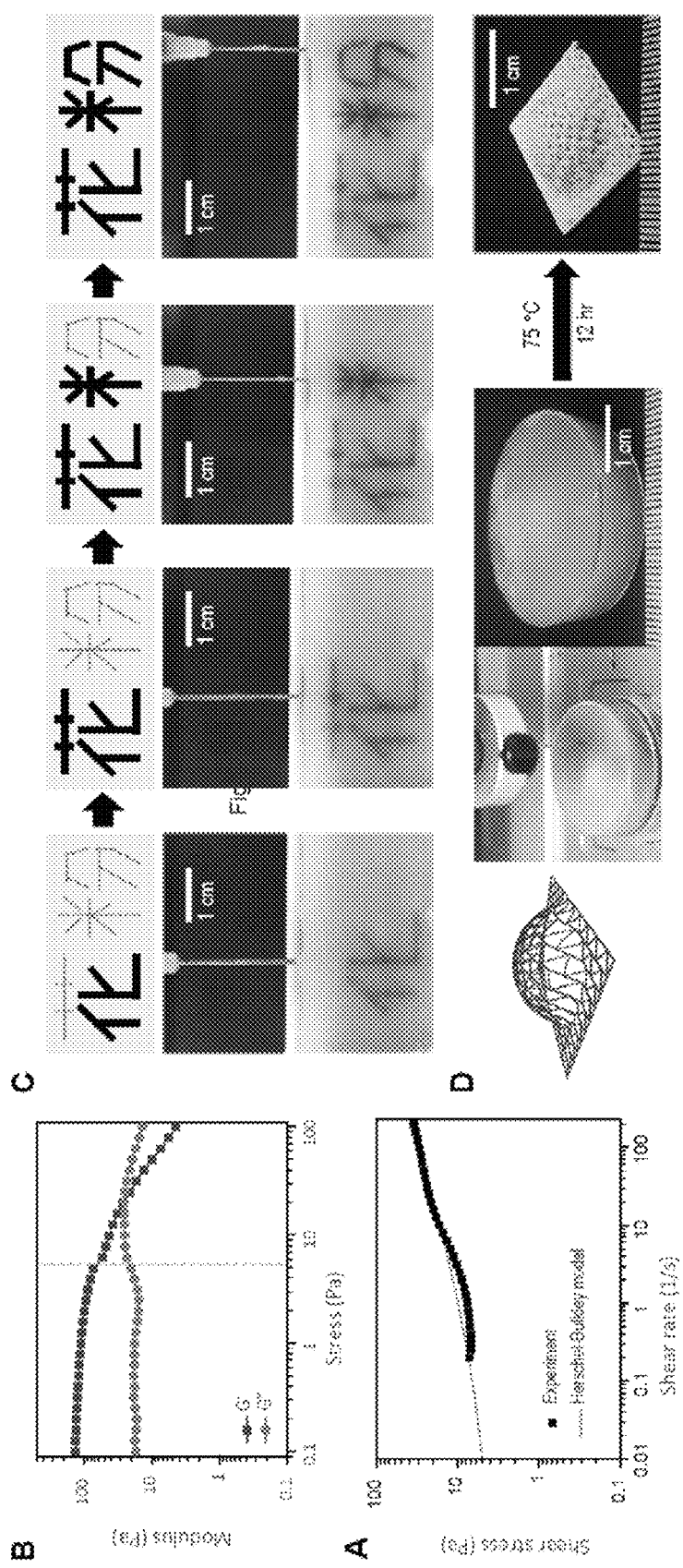

FIG. 19. Writing in the pollen microgel medium. A. Shear stress as a function of the shear rate for pollen microgels obtained after 6 hr deesterification process. The red dashed line indicates curve fitting with the Herschel-Bulkley model. B. Storage (G') and loss (G") moduli as a function of the oscillatory strain for pollen microgels obtained after 6 hr deesterification process. The grey vertical line indicates yield strain (γ_0) where tan δ=1. C. Storage (G') and loss (G") moduli with three oscillatory intervals for assessment of thixotropic behavior at γ=1% for t=0-200 s, γ=70% (>γ_0) for t=200-500 s, and then γ=1% for t=500-950 s. D. Images of the letter, "花粉" in the pollen microgel medium printed in black alginate ink, indicating the sequential printing path of the letter. E. A model of a meshed dome structure and its printed object from 3D freeform printing in the pollen microgel medium using PDMS ink. The printed silicone was cured at 75° C. for 12 hrs directly inside the gel medium. All scale bars, 1 cm.

Figure 20:
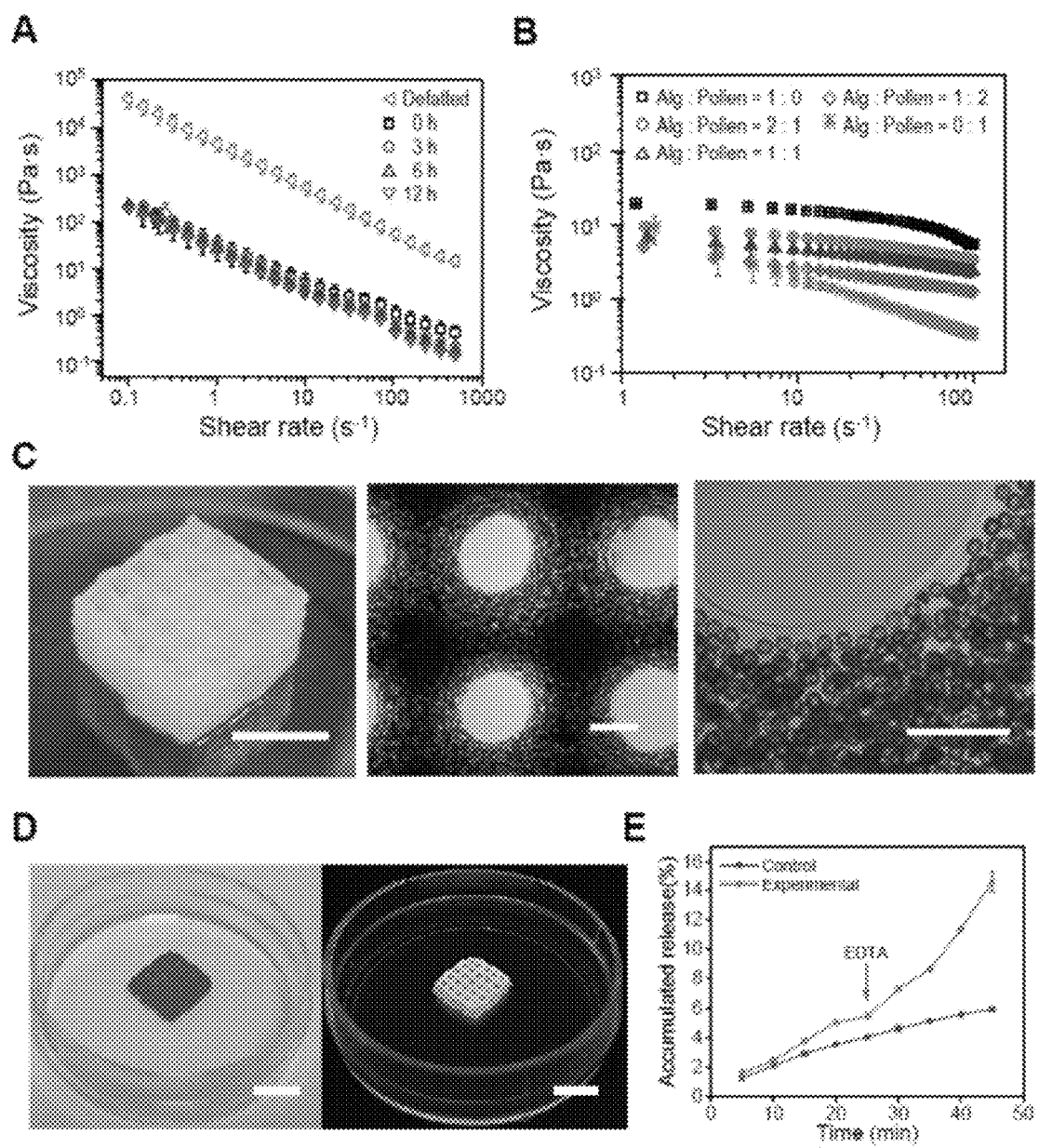

FIG. 20. Pollen microgels as additives in various hydrogel inks. A. The viscosity of pollen grains varies with the treatment conditions during the pollen process. 10 v/v % defatted pollen exhibit two orders of magnitude larger viscosity than 10 v/v % KOH-treated pollen. B. As one of common hydrogel inks, alginate has been applied to various 3D printing systems due to its simple and cell-friendly crosslinking process. Various alginate-pollen composite inks with different volumetric ratios of 0:1, 1:2, 1:1, 2:1 and 1:0 were prepared in order to confirm the viscosity of those inks depending on the composition of inks. All composite inks show lower viscosity than pure alginate inks due to the higher water content of pollen microgels. All prepared inks were printable, maintaining their printed structure after the post-treatment using 153 mM CaCl$_2$) solution. C. The 3D porous scaffold of algihate-pollen composite was successfully fabricated where pollen microgels were well-dispersed within the alginate strut. D. Smart pollen microgel carriers were assessed using a fluorescent dye, Rhodamine B. The Ca$^{2+}$/EDTA-associated stimulus-responsive mechanism of pectin was used for EDTA-initiated release of drugs for pollen microgels. To avoid the influence of EDTA to other ink materials, a photo-crosslinkable hyaluronic acid (HAc)/alginate/pollen system was used. While printability of the HAc-based composite inks was good, for printing quality, a gelatin granular medium was used for the printing of the HAc-based composite inks. With Rhodamine B-loaded pollen microgels, the printed scaffolds became red due to the passive diffusion of Rhodamine B. The EDTA-responsive release behavior of Rhodamine B-loaded pollen microgels was quantitatively assessed.

DETAILED DESCRIPTION OF THE INVENTION

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

A central assumption behind all known applications of pollen is that pollen grains are practically indestructible and structurally immutable. The inventors have now identified a one-pot processing strategy akin to classical soapmaking as described herein that converts hard pollen grains into pliable, soft microgel particles. The approach works by reducing cross-linker density in the pollen wall. The microgel building blocks could form bulk gels or assemble into high-strength sheets and three-dimensional sponges. Profiling pollen grains and spores from across the plant kingdom revealed that microgel formation is restricted to eudicot plants. Considering the high abundance and low cost of pollen, these findings have broad implications for scalable fabrication of complex materials from natural, renewable sources.

With the intention to develop a functional material incorporating the potential benefits of sporopollenin, the process of SPC hydrolytic degradation under alkaline conditions for a wide range of pollen species was studied. Angiosperm-derived SPCs exhibited the tendency to degrade, and unexpectedly form functional gel-based systems that undergo inter-particle binding to produce sheets and porous 3D structures. The protocol described herein requires only the use of alkaline metal hydroxide (preferably KOH) aqueous solutions and water to obtain these results, along with controlled amounts of incubation time and other steps to control the material properties of the fabricated structures. It was found that it is thus possible to manipulate the SPC structure in a controllable manner and specifically engineer the material properties.

It was identified that the hydrolytic degradation of the sporoderm polymer complex (SPC) derived from angiosperm pollen is facilitated in alkaline conditions. Base-hydrolysis and 28-day incubation resulted in SPC degradation followed by restructuring and stabilization. Individual particles were shown to exhibit functionality as a bio-derived pH responsive hollow core-shell microgel system. Particle-particle adhesion led to aggregation and sheet formation under simple drying conditions. Freeze-casting and lyophilization of SPC gels produced porous 3D structures. One potential application of SPC sponges for use in tissue engineering applications was demonstrated.

The advantages and improvements over existing methods, devices or materials reside in that the described alkaline-assisted hydrolytic degradation of pollen gives a versatile biopolymer for the formation of responsive microgel systems, sheets, and sponges/foams. Polymer degradation proceeds until sufficient proportions of acidic groups capable of hydrogen bonding cause the polymer chains to realign and stabilize the system. The properties of the SPC can be varied through process optimization to tune the resultant material systems and allow for a diverse range of fundamental and applied materials science studies. For example, it was found that a simple and scalable chemical treatment method could be used to mimic the stimulus-responsive swelling-deswelling behavior of pollens by synthetically activating pectin. This allowed to directly apply the natural smart microgel building blocks derived from pollens to three-dimensional (3D) printing systems as either a "write-in" supporting matrix or a "write-out" smart material ink component. Furthermore, this also facilitate the use of the SPC containing microgels for EDTA-initiated release of encapsulated agents from the pollen microgels by exploiting the $Ca^{2+}$/EDTA-associated stimulus-responsive mechanism of pectin. The ease of processing and biocompatibility of the SPC material highlights the significant potential of SPC as a new biomaterial.

The invention relates in a first aspect to a method for the formation of microgels of sporoderm polymer complex microcapsules (SPC-MCs), the method comprising the steps of (a) providing pollen grains from eudicot plants;

(b) deproteinizing the pollen by contacting it with an aqueous base solution at elevated temperatures for up to 10 hours to obtain porous SPC-MCs;

(c) hydrolytically degrading the SPC-MCs by contacting it with an aqueous base solution for periods up to 60 days to obtain microgels of SPC-MCs.

The term "microgel", as used herein in relation to the sporoderm polymer complex microcapsules, is used as commonly understood in the art, namely to relate to macromolecular networks swollen by the solvent in which they are dissolved. Microgel networks range in size from several micrometers down to nanometers (then sometimes called "nanogels"). While in a collapsed state, they can resemble hard colloids but they can still contain significant amounts of solvent, whereas when swollen, they are soft and may have a fuzzy surface. The presence of cross-links provides structural integrity, and the properties of microgels may be tuned by the cross-linker content such that the microgels behave more "colloidal" or "macromolecular".

The combination of being soft and porous while still having a stable structure through the crosslinked network allows for designing microgels that have different properties due to a different architecture while retaining the same chemical composition. Microgels may have the property to adjust both their shape and volume in response to external stimuli (e.g., temperature, ionic strength and composition, pH, electrochemical stimulus, pressure, light) and thus may allow reversible tuning of their physicochemical properties.

Herein, the term "microgel" when used in relation to SPC-MC based compositions relates to microgels made of sporoderm polymer complex microcapsules swollen in an appropriate solvent, i.e. typically in an aqueous solvent, after having been subjected to an alkaline treatment and partial hydrolysis. In such a state, i.e. partially hydrolyzed by methods described herein, dispersed in and swollen by an aqueous solvent, usually at about neutral pH, the SPC-MCs exhibit the typical behavior of microgels and show tunability of certain properties by change in pH values, as will be described in more detail below.

"Sporoderm polymer complex" or "SPC", as used herein, relates to the polymer of the shell wall of pollen, more particularly comprising sporopollenin as an outermost layer (exospore or exine) with cellulose, hemicellulose, and pectin as an inner layer (so-called intine). Sporopollenin is the essential component of the SPC and responsible for most of its properties. As already described above, sporopollenin is a crosslinked biopolymer with a highly complex structure, essentially composed of fatty acids, phenylpropanoids and phenolic components, such as ferulic acid (3-methoxy-4-hydroxycinnamic acid) and p-coumaric acid (4-hydroxycinnamic acid).

In contrast to the term "SPC", the term "sporopollenin exine capsule" or "SEC", only relates to the outermost shell of the pollen grain made of sporopollenin, i.e. without the intine inner shell layer.

The term "capsule" or "microcapsule", as used herein, is used in the meaning as established in the field, i.e. to relate to a hollow particle, typically essentially spherical, that has an average diameter in its largest dimension of micron scale. In relation to the SPC-MCs or SECs, as used herein, the term describes hollow capsules with shell walls made of sporopollenin and optionally other polymers derived from the intine layer, that may have been modified by the alkaline-assisted hydrolytic degradation methods described herein. Typical sizes are those of the pollen grains they are derived from and thus range from about 5 µm to about 120 µm in diameter, usually about 6 to about 90-100 µm. These sizes relate to the main body of the spore and do not include any sculpted surface structures, such as spikes or the like. "About", as used herein in relation to numerical values, means said referenced value ±10%, preferably ±5%.

The term "pollen" as used herein, relates to the fine to coarse powdery substance comprising pollen grains which are male microgametophytes of seed plants, which produce male gametes (sperm cells). Pollen and pollen grains can be obtained from various sources and are for example also commercially available.

"Eudicot plants", as used herein, is another term for "Eudicotidae" or "eudicotyledons" and relates to a clade of flowering plants that had previously been called tricolpates or non-magnoliid dicots by previous authors. As used herein, it relates to those plants that are classified as eudicots according to the APG IV system of flowering plant classification, this being the fourth version of a modern, mostly molecular-based, system of plant taxonomy for flowering plants (angiosperms) being developed by the Angiosperm Phylogeny Group (APG) as published in 2016. According to the APG IV system, the clade "eudicots" comprises plants of the following orders and clades: order Ranunculales; order Proteales; order Trochodendrales; order Buxales; in the clade Core eudicots: order Gunnerales; order Dilleniales; in the clade Superrosids: order Saxifragales; in the clade Rosids: order Vitales; in the clade Fabids: order Fabales; order Rosales; order Fagales; order Cucurbitales; order Oxalidales; order Malpighiales; order Celastrales; order Zygophyllales; in the clade Malvids: order Geraniales; order Myrtales; order Crossosomatales; order Picramniales; order Malvales; order Brassicales; order Huerteales; order Sapindales; in the clade Superasterids: order Berberidopsidales; order Santalales; order Caryophyllales; in the clade Asterids; order Cornales; order Ericales; in the clade Campanulids: order Aquifoliales; order Asterales; order Escalloniales; order Bruniales; order Apiales; order Dipsacales; order Paracryphiales; in the clade Lamiids: order Solanales; order Lamiales; order Vahliales; order Gentianales; order Boraginales; order Garryales; order Metteniusales; and order Icacinales.

The claimed methods are based on the surprising finding of the inventors that when subjecting pollen of *Helianthus annuus* to standard protocols for SEC extraction, the common standard protocols involving a defatting step with acetone, a protein removal step with an aqueous solution of KOH, an intine removal step with an aqueous solution of phosphoric acid ($H_3PO_4$) and multiple washing steps with water, solvents, acids and bases, it was surprisingly discovered that the pollen formed a gel-like paste during the protein removal step with aqueous KOH solution. This behaviour was previously unknown and stands in stark contrast to the behaviour of pollen from other sources, such as the most commonly studied source of pollen, *Lycopodium clavatum*. By following studies, it was found that this behaviour of forming paste-like microgels when subjected to alkaline-assisted hydrolytic degradation, appears to be a characteristic of eudicot plants.

In the claimed method for the formation of microgels of sporoderm polymer complex microcapsules (SPC-MCs), the method comprises the steps of (a) providing pollen grains from eudicot plants;

(b) deproteinizing the pollen by contacting it with an aqueous base solution at elevated temperatures for up to 10 hours to obtain porous SPC-MCs;

(c) hydrolytically degrading the SPC-MCs by contacting it with an aqueous base solution for periods up to 60 days to obtain microgels of SPC-MCs.

The pollen provided may originate from any common source for pollen, with pollen and pollen grains being commercially available from a variety of sources, such as from Sigma Aldrich. The pollen is typically provided in powder form that may, depending on the species it is derived from, be fine or coarse. While it is commonly provided in powder form, in alternative embodiments, the pollen may also be provided in form of a dispersion in an adequate solvent, such as water. It is however preferred to provide the pollen in solid form. The pollen may comprise, consist essentially of or consist of pollen grains.

The pollen used in step (a) may be defatted. It is generally preferred to use pollen that has been defatted before use in the inventive methods. Accordingly, in various embodiments, the pollen used is either defatted pollen or the method further includes a step of defatting the pollen prior to step (b). The defatting step may be carried out by dispersing the pollen in an organic solvent, such as, without limitation, acetone or other ethers or ketones, such as diethyl ether, methyl ethyl ketone and the like. In principle, all organic solvents having the capability to dissolve fats and waxes while not adversely affecting the shell polymer structure can be used. Suitable methods for defatting pollen are known in the art. To avoid that organic solvents are introduced into the alkaline solutions used in the following steps, it is preferred that the defatted pollen is dried before it is subjected to the following processing steps.

The pollen used may be from any suitable source, i.e. any eudicot plant. Exemplary clades and orders of plants from which the pollen may be derived have been described above and include plants of any one of the orders and clades listed above in connection with the definition of the term "eudicot plants".

In various embodiments, the pollen may originate from a flowering plant of the genus *Baccharis, Helianthus* or *Camellia*, such as *Helianthus annuus*.

To ensure the isolation of the sporoderm it is usually necessary to adequately remove all proteinaceous pollen compounds. In various embodiments of the inventive methods, the aqueous base solution used in step (b) comprises, consists essentially of or consists of an aqueous alkaline metal hydroxide solution, preferably potassium hydroxide (KOH) or sodium hydroxide (NaOH) solution, more preferably KOH solution. "Consist essentially of", as used herein, means that a given composition is primarily made of the respective component, i.e. comprises it in an amount of more than 50% by weight/volume, preferably more than 70%, more preferably more than 80%. It can also mean that the given composition does not contain any other component that has the desired functionality, i.e. all other components, if present, are irrelevant for the intended purpose and serve only as auxiliaries.

In these solutions, the alkaline metal hydroxide concentration is sufficient to allow the desired protein degradation and polymer hydrolysis. Typical concentrations may range from about 0.5 to about 40% (w/v), preferably from 1 to 25% (w/v) relative to the total volume of the solution. In various embodiments, the concentration may range between 5 and 25% w/v, such as 6, 10, 15, 20 or 25% w/v KOH. The given amounts preferably relate to KOH. If NaOH is used instead, the given concentrations may be increased by a factor of 1.4.

The "contacting" is preferably carried out by dispersing the pollen in the aqueous base solution. The dispersing can be achieved by any suitable means, commonly by stirring. Alternatively, the pollen can also be provided in already dispersed form, for example in water as the continuous phase. In such embodiments, the two liquid solutions are combined, usually while stirring, agitating or shaking or the like.

The hydrolysis reaction is typically carried out for periods of time of up to 20 hours, usually durations of up to 10 hours, 30 minutes to 8 hours, for example 1 to 6 hours, such as 1, 2, 3, 4, 5 or 6 hours. During said incubation period, the solution is typically agitated by shaking or stirring.

The hydrolysis reaction is more effective if carried out at elevated temperatures. "Elevated", as used herein in relation to temperatures, means temperatures above room temperature, i.e. typically above 20, preferably above 25° C. In various embodiments, step (b) is carried out at a temperature of 40 to 95° C., preferably 60 to 90° C., more preferably 70 to 85° C. and/or for a period of 1 to 6 hours, preferably 2 to 4 hours.

Typically, the aqueous base solution is used in mass ratios of 5:1 to 25:1, preferably 7.5:1 to 15:1 with respect to the mass of the pollen used. This means that typically about 1 g of pollen is dispersed in 7.5 to 15 mL aqueous base solution.

After step (b) has terminated, i.e. the intended incubation period has been reached, the suspension may be washed with the aqueous base solution to remove proteinaceous debris. In various embodiments, the aqueous base solution used for such washing steps is the same as the one used for the hydrolysis reaction. In any case, it is preferred to remain high pH values during washing, in particular pH values higher than 10 or 12. These washing steps may be carried out using (vacuum) filtration or centrifugation to separate the hydrolyzed pollen particles from the undesired protein debris.

One standard protocol includes exposing the pollen to a 6% (w/v) KOH solution for 6 h at 70° C. followed by filtering to remove $KOH_{aq}$ and refreshing of the KOH solution. Alternatively, protein removal can be achieved with hydrolysis durations of 1, 2, and 4 h, with 1%, 10%, and 25% KOH, at 80° C.

After this deproteinization or base hydrolysis step (b), the pollen particles are incubated with fresh aqueous base solution for step (c). Said aqueous base solution used in step (c) may be defined as described above for the solutions used in step (b). In particular, it is again preferred to use KOH or NaOH solutions of the above-given concentrations, preferably KOH solutions.

While step (c) may be carried out at elevated temperatures, it is typically preferred to use temperatures in the range of 10 to 30° C., preferably 15 to 25° C.

The hydrolytic degradation of the pollen particles, also called saponification step, can be carried out for extended periods of time ranging from one or more days to several months.

Saponification occurs when lipidic compounds are exposed to bases such as NaOH or KOH. This is a fundamental chemical reaction in the process of soap making, wherein triglycerides are treated with strong bases to cleave ester bonds and produce fatty acid salts and glycerol. Saponification typically requires a prolonged reaction time of 24-48 h at room temperature. If high temperature is applied, the saponification process duration can be reduced. However, these time frames are quite variable and are for standard fats used in soap making. For example, known processes for soap making also indicate that curing of soaps is typically performed for 4 to 6 weeks, wherein reactions continue to occur, consuming any residual base.

Typical periods of time useful in the methods of the invention are thus up to 60 days long, typically up to 42 days, for example 7 to 35 days, preferably 14 to 28 days. It is understood that by changing the process conditions, such as the temperature, shorter times may similarly be sufficient.

The incubation in step (c) can be carried out in a static state or can be carried out while agitating the suspension, i.e. by stirring or shaking. Preferred are static state treatments.

In various embodiments, step (c) further includes a step of neutralizing the suspension of partially degraded SPC-MCs after incubation for the above-indicated time periods by washing the partially degraded SPC-MCs with water until the suspension has a pH in the range of 6.0 to 8.5, preferably in the range of 6.5 to 8.0, more preferably in the range of 7.0 to 7.5. Thus it is possible to obtain a neutralized microgel solution. After said step, the pollen particles are hydrolytically degraded such that they form a soft, pliable microgel swollen with the respective solvent, typically water.

Water washing of pollen-derived capsule systems typically involves multiple washing steps with deionized (DI) water. In a wash step, samples are topped up with water, stirred or vortexed for several minutes, centrifuged or vacuum filtered, and the supernatant is removed. After all water washing is completed, centrifugation with removal of supernatant is performed multiple times so as to ensure removal of as much free water as possible.

"Partially degraded", as used in this context, means that the crosslinking density in the pollen wall, i.e. in particular the sporopollenin shell, is reduced relative to the naturally occurring polymer by hydrolyzing part of the crosslinking bonds, in particular ether (COC) and ester (COOC) bonds. This may be monitored by X-ray photoelectron spectroscopy (XPS). The degradation is notable by decreases in the amount of these bonds. As described above, this changes the physicochemical properties of the microcapsules obtained and provides for microgels of the SPC-MCs. In various embodiments, the SPC-MCs of the present invention are characterized in that they undergo a reduction in ester bonds during the alkaline treatment, as monitored by XPS. This is a clear distinction over pollen capsules from other plant species that show no change or an increase in the number of ester bonds under the same treatment.

The microgel obtained typically is a viscous aqueous gel comprising 1 to 6 wt.-% SPC-MCs and the remainder being water, i.e. 94 to 99 wt.-% being water.

The present invention is directed to the SPC-MCs as obtained after the described methods and also encompasses the microgel and microgel-containing compositions obtainable or obtained according to the described methods. The microgels contain the SPC-MCs in the form of soft, pliable microgel particles, which can be used as microgel building blocks in a variety of applications, such as to form bulk microgels or to assemble into high-strength sheets and three-dimensional sponge structures.

The SPC-MCs that form the microgel may be subjected to further processing steps, such as an intine removal step, for example by treatment with phosphoric acid. Thus, sporopollenin exine capsules (SECs) may be obtained. These may be further purified by various washing steps, for example with water, acids and bases. It is however preferred to use the SPC-MCs without an intine removal step.

To form such sheet or sponge structures, the microgels may be produced according to the afore-described methods followed by the step of (d) forming a film of the microgel on a substrate and drying the film to obtain a flexible sheet of SPC-MCs; or (e) lyophilizing the microgel to obtain sponge structures of SPC-MCs.

To form sheets, the microgels obtained may be poured onto a substrate or into a mold and then dried. The drying may occur under reduced pressure (vacuum) and/or elevated temperatures. This reduces the water content in the microgel to such an extent that a flexible sheet can finally be obtained.

The lyophilization can be carried out using standard procedures known in the art. Typically, the microgel or microgel solution is cast into a suitable container or mold, then frozen and the solvent (water) then sublimated under vacuum. Thus, sponge-like structures of various shapes can be obtained.

It is understood that the flexible sheets or sponges comprising SPC-MCs obtainable by the methods described herein also form part of the invention.

The microgels, sheets and sponges of the invention may be used in various compositions. Examples for compositions in which they may be advantageously used include, without limitation, cosmetic, nutritional or pharmaceutical compositions. Further compositions are compositions for 3D printing and printing ink compositions. Such compositions also form part of the invention.

Exemplary cosmetic products include masks, anti-aging and anti-wrinkling compositions, but are not limited thereto. Suitable applications of the sheets of the invention may include wound healing, skin protection (against UV), soft tissue engineering and regenerative medicine. The foams and sponges of the invention can be use as medical implants, for wound dressing and wound healing, as UV blocking materials, 3D cell culture and tissue engineering platforms, and as drug delivery vehicles.

One possible use of the microgel particles of the invention includes the use as a thickener or gelling agent. Such agents are widely used in various fields of technology, including pharmaceuticals, paints, inks, adhesives, liquid detergents, cosmetics and foods. Accordingly, in various embodiments, envisioned is the use of the microgels of the invention in printing, cosmetic or food compositions.

Alternative uses of the microgels, flexible sheets or sponges are as scaffold materials for cells, for example in cell culture or medicinal applications. It has been found that such scaffolds can significantly promote cell proliferation compared to other materials that have been proposed for this purpose.

A still further use of the microgel, the flexible sheets or sponges is in the delivery of an active agent, wherein said active agent is preferably encapsulated in the SPC-MCs. The active agent may be a pharmaceutically or cosmetically active agent or a cosmetic or pharmaceutical composition that comprises a pharmaceutically or cosmetically active agent. Methods and techniques for loading such agents into the pollen capsules described herein are known to those skilled in the art. The release of said agent may be triggered by various stimuli, such as by controlling the pH or calcium levels.

Such pharmaceutically or cosmetically or any other active agent may then be delivered to a specific site, for example in a subject in need thereof. Generally, such methods may comprise providing a composition comprising the microgel or the flexible sheets or sponges of the invention, the microgel, flexible sheets or sponges comprising the pharmaceutically or cosmetically active agent encapsulated in the SPC-MCs, and administering a pharmaceutically or cosmetically active amount of the composition to a subject. The amount is selected such that the concentration of the active agent achieved is sufficient to cause the desired effect.

A still further aspect of the invention relates to a method for promoting cell proliferation comprising (a) contacting cells with a sheet or sponge according to the invention; and (b) culturing said cells in the presence of said sheet of sponge as a scaffold under suitable culturing conditions.

Suitable culturing conditions, as used herein, refers to such culturing conditions, i.e. temperature, nutrients, pH, $CO_2$ concentration, etc., that allow the cells to stay viable, grow, differentiate or proliferate. Such cell culturing conditions are well known in the art for various cell types and cell lines and may be adopted, with the only difference lying in that conventional scaffolds for cell growth are replaced by the sheets or sponges of the invention.

The present invention is further illustrated by the following examples. However, it should be understood, that the invention is not limited to the exemplified embodiments.

EXAMPLES

Example 1

Defatted *H. annuus* pollen was obtained from Greer Labs (USA). Potassium hydroxide (KOH) was obtained from Sigma-Aldrich (Singapore).

Pollen (2 g) was added to aqueous 1, 10, or 25 (w/v) % KOH (20 ml) in a 50 ml PTFE round bottom flask with a 2 cm stirring bead. The solution was mixed thoroughly by magnetic stirring bead at 750 rpm until all pollen agglomerates were dispersed. The solution was refluxed for 2 h at 80° C. with stirring at 200 rpm. The solution was transferred to a 50 ml falcon tube, then centrifuged at 4500 rpm for 5 min. The supernatant was removed and the sample was topped up to 20 ml with fresh $KOH_{aq}$ of the same concentration used for the initial base-hydrolysis step. The mixture was vortexed at high speed for 2 min, followed by centrifugation at 4500 rpm for 5 min. The $KOH_{aq}$ washing was repeated for a total of 5 times. Finally, fresh $KOH_{aq}$ was added up to a total of 20 ml, followed by vortexing at high speed for 2 min, and the sample was left to sit at room temperature (25° C.) to incubate for a duration of 0, 7, 14, 21, or 28 days.

After the appropriate incubation period of 0, 7, 14, 21, or 28 days, the pollen in $KOH_{aq}$ was vortexed at high speed for 2 min to ensure uniform mixing, and 2 ml of suspension was aliquoted into a 15 ml falcon tube for water washing. The aliquoted suspension was topped up to 10 ml with distilled water and vortexed at high speed for 2 min, followed by centrifugation at 4500 rpm for 5 min. The pH of the supernatant was measured and then the supernatant was then removed. If the supernatant pH was greater than 7.5, the tube was topped up to 10 ml with distilled water, followed again by vortexing and centrifugation. The water washing was typically repeated for a total of 4 to 6 washes to achieve neutral pH (~7.5).

The remaining base-hydrolyzed and water-washed pollen was transferred to a 2 ml vial using a 3 ml disposable dropper, and topped up to 2 ml with distilled water and vortexed briefly to mix. The suspension was centrifuged at 14000 rpm for 5 min, and the supernatant was removed. The centrifugation and supernatant removal process were repeated for a total of 3 times, so as to remove as much free water as possible. Wet samples were used within 4 hours of preparation for morphological analysis of the bulk microgel by confocal laser scanning microscopy (CLSM), and rheological analysis of the bulk microgel.

For analytical techniques requiring dry samples, the tube was covered with parafilm, and needle holes were added, then additional filter paper was taped over the parafilm to ensure no pollen particles could come out during lyophilization. The covered tube was frozen overnight (~12 h) at −20° C. and lyophilized overnight (~24 h) and checked until stable weight. The tube plus processed pollen was weighed, followed by weighing the lyophilized processed pollen only. Wet weight+tube, dry weight+tube, and dry weights, allowed for calculation of processed pollen yields, as well as water content and pollen content of the bulk microgel. The lyophilized samples were stored in a dry cabinet until further characterization.

The results indicate that pollen from 5 of 10 species that were explored can degrade in alkaline conditions.

Figure 1:
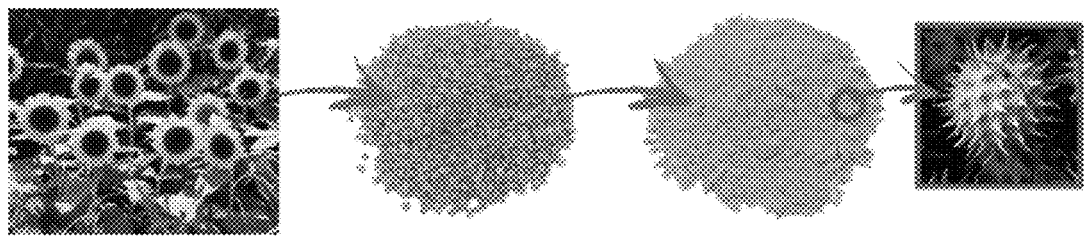
FIG. 1 illustrates the strategy to transform pollen grains into processable microgel building blocks. (A) Hard pollen grains are readily obtained from flowering plants and can be processed into soft microgel particles. (B) The pollen-derived microgel particles are further assembled into bulk gels, sheets, and sponges with a diverse range of material properties and without fillers or additives.
Figure 1:
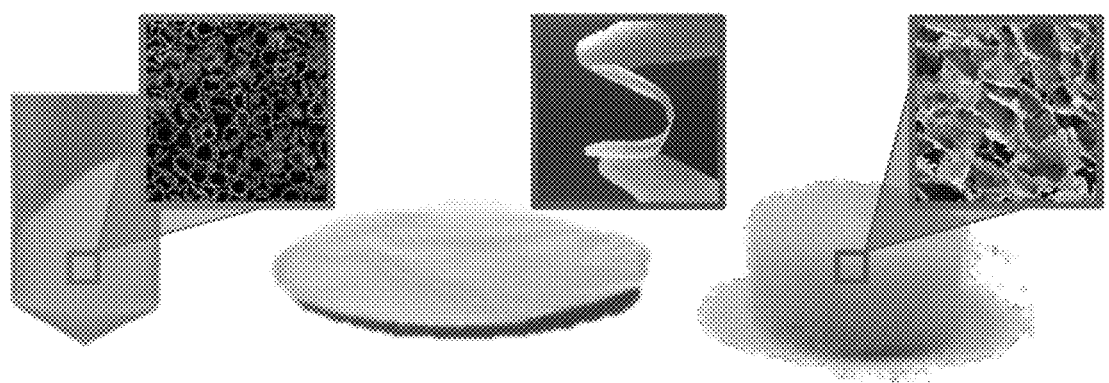
Figure 2:
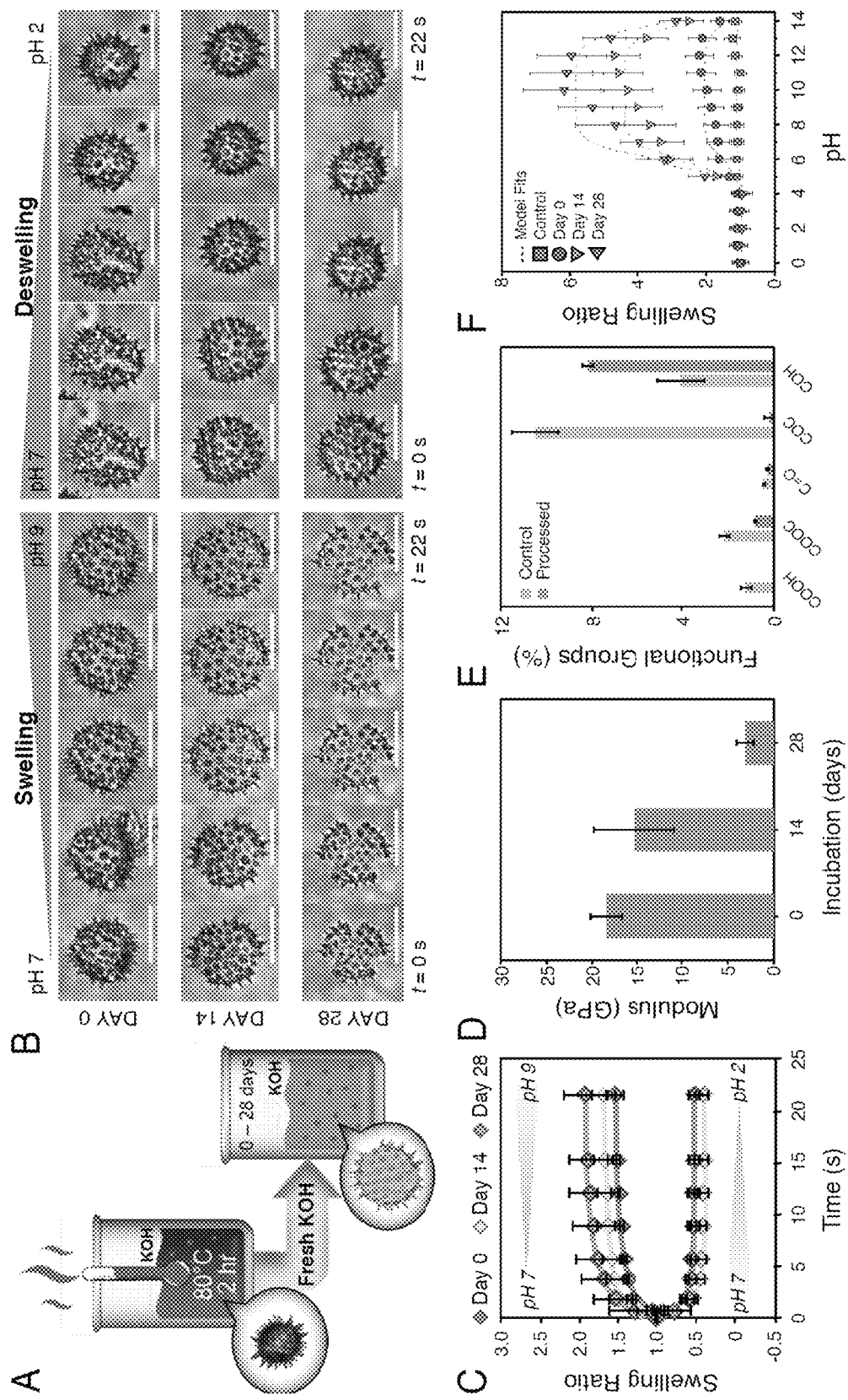
FIG. 2 shows structural characterization and mechanistic understanding of pollen microgel building blocks. (A) Processing schematic to convert hard pollen grains into soft microgel particles. Day 0 treatment is defined as pollen treatment in 80° C. KOH for two hours, without further incubation. (B) Time-lapsed optical micrographs of single pollen grains in aqueous solution with various pH conditions. Over the measured period, the solution pH was changed from pH 7 to pH 9 (left panel) or from pH 7 to pH 2 (right panel). The pollen grains samples were prepared after incubation in alkaline conditions for 0, 14 or 28 days. (C) Quantitative measurement of swelling behavior of 0-, 14- or 28 day-treated pollen grains as a function of time from pH 7 to pH 2 or pH 7 to pH 9 (n=3 particles). (D) Determination of the Young's modulus of 0-, 14- or 28 day-treated pollen grains by nanomechanical AFM measurements (n=60 particles). (E) XPS analysis of functional groups (COOH, COOC, C=O, COC, and COH) in alkaline-treated pollen grains without and with 28-day alkaline treatment. Mean±s.d. are reported from 3 independent samples. (F) Experimental swelling data and curve fit of 0-, 14- or 28 day-treated pollen grains as a function of solution pH, compared to unprocessed pollen grains (n=50 particles). Dotted lines correspond to theoretical fits of swelling ratios for sporopollenin polymer network. Data in C-F depict mean±standard deviation (s.d.).
Figure 4:
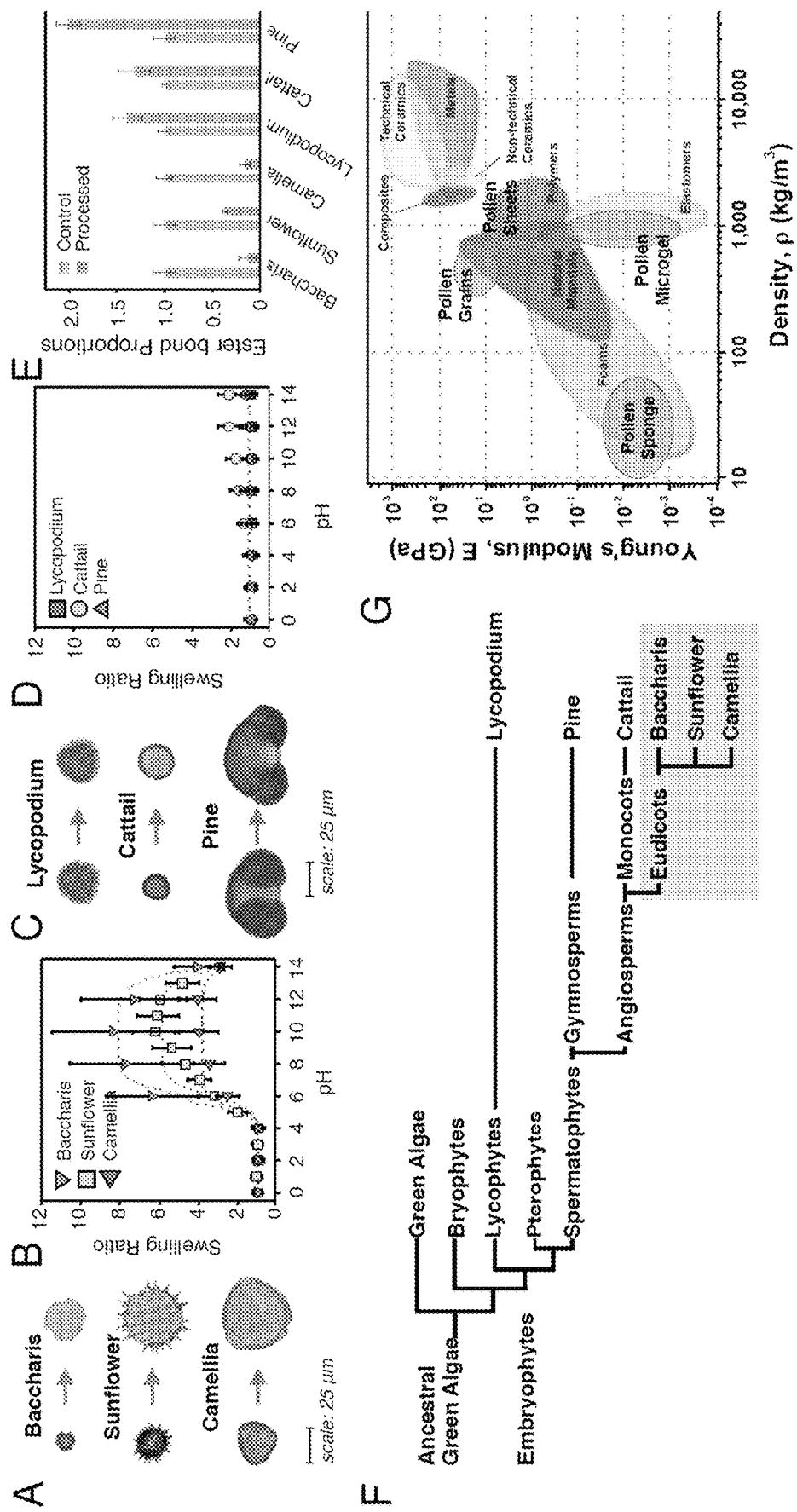
FIG. 4 shows the profiling of microgel formation from various plant species. (A) Optical micrographs of individual pollen grains from three species (*Baccharis*, Sunflower and *Camelia*) produced by 28 day-treatment, after the pH was changed from pH 2 to pH 9. (B) Equilibrium swelling data and curve fit of 28 day-treated pollen grains (*Baccharis*, Sunflower and *Camelia*) as a function of pH (n=50 particles). Dotted lines correspond to theoretical fits of swelling ratios. (C) Optical micrographs of individual pollen grains from three species (*Lycopodium*, Cattail and Pine) produced by 28 day-treatment, after the pH was changed from pH 2 to pH 9. (D) Equilibrium swelling data and curve fit of 28 day-treated pollen grains (*Lycopodium*, Cattail and Pine) as a function of pH (n=50 particles). Dotted lines correspond to theoretical fits of swelling ratios. (E) XPS analysis of ester bond proportions in unprocessed and processed pollen from six different plant species. Data depict mean±s.d (n=3 independent samples). (F) Evolutionary cladogram of algae and green plants. The highlighted region indicates plant species that produce microgel-forming pollen species. (G) Material property charts for natural and synthetic materials: Young's modulus vs density. The chart compares pollen and pollen-derived materials to other engineered and natural materials.
Figure 5:
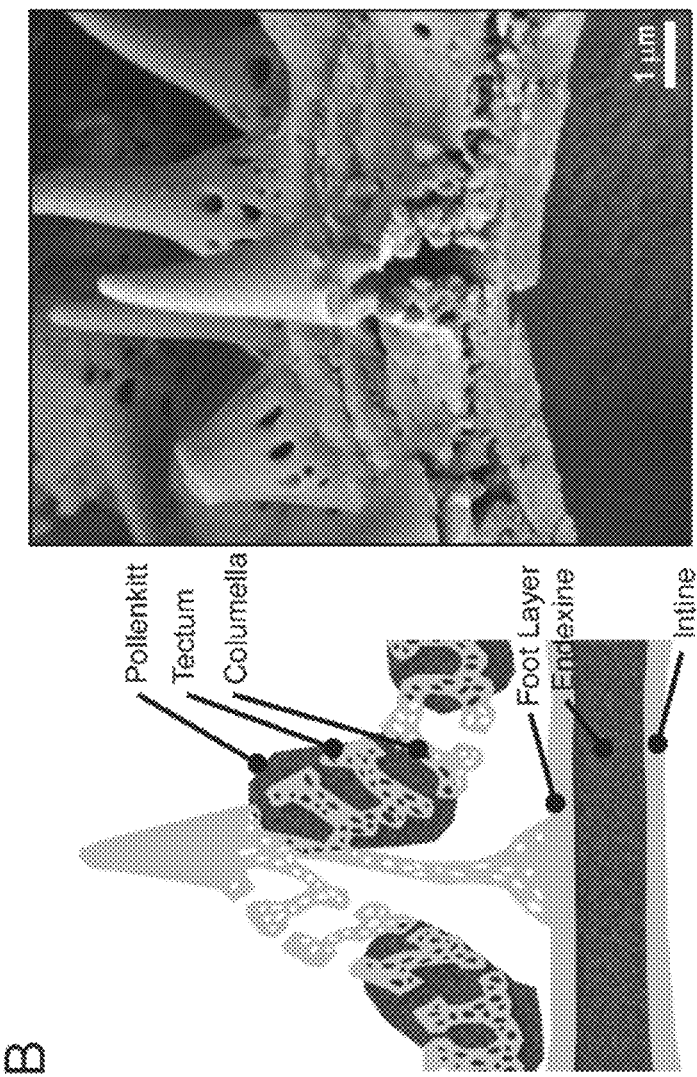
FIG. 5. Sunflower pollen morphology and porosity. (A) Scanning electron microscopy (SEM) images of sunflower pollen surface morphology. (B) Schematic diagram and SEM image of sunflower pollen cross-section.
Figure 6:
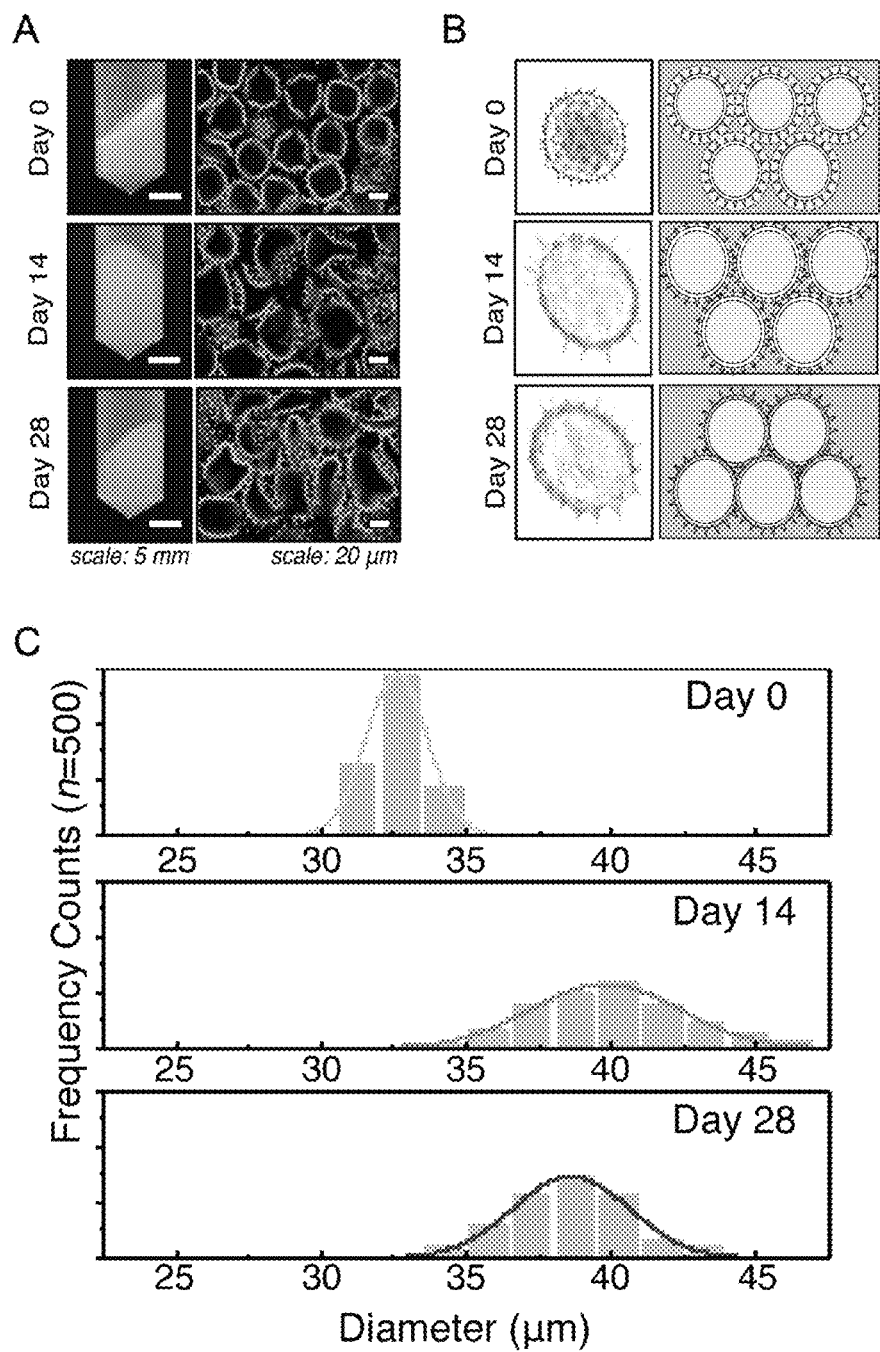
FIG. 6. Characterization of alkaline-treated sunflower pollen microgels with respect to duration of extended KOH incubation. (A) Photographs and confocal laser scanning microscopy (CLSM) cross-section images of sunflower pollen microgels. (B) Optical microscopy images of representative pollen particles and illustrative drawings indicating pollen volume and water volume per particle. (C) Pollen particle diameter distributions, as measured by dynamic image particle analysis (DIPA) (n=500 particles).
Figure 7:
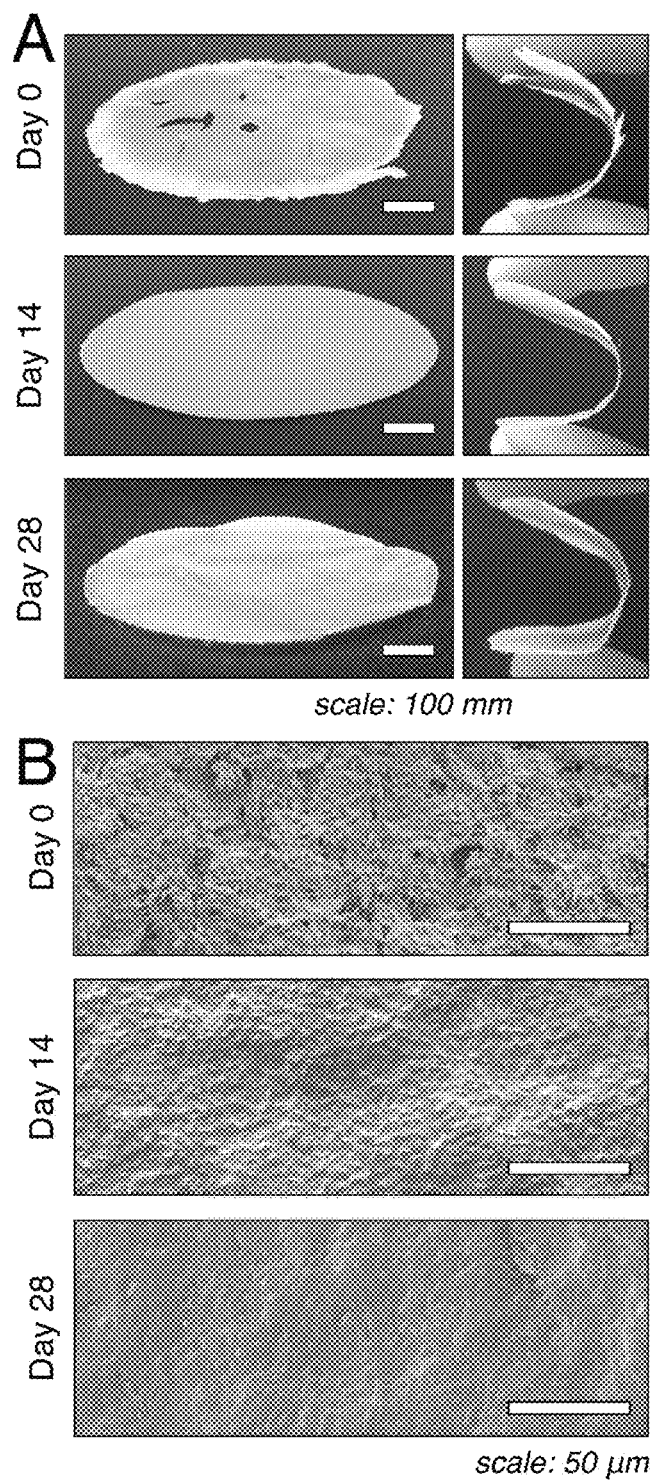
FIG. 7. Characterization of alkaline-treated sunflower pollen sheets with respect to duration of extended KOH incubation. (A) Photographs of sunflower pollen sheets. (B) Scanning electron microscopy (SEM) images of sunflower pollen sheets.
Figure 8:
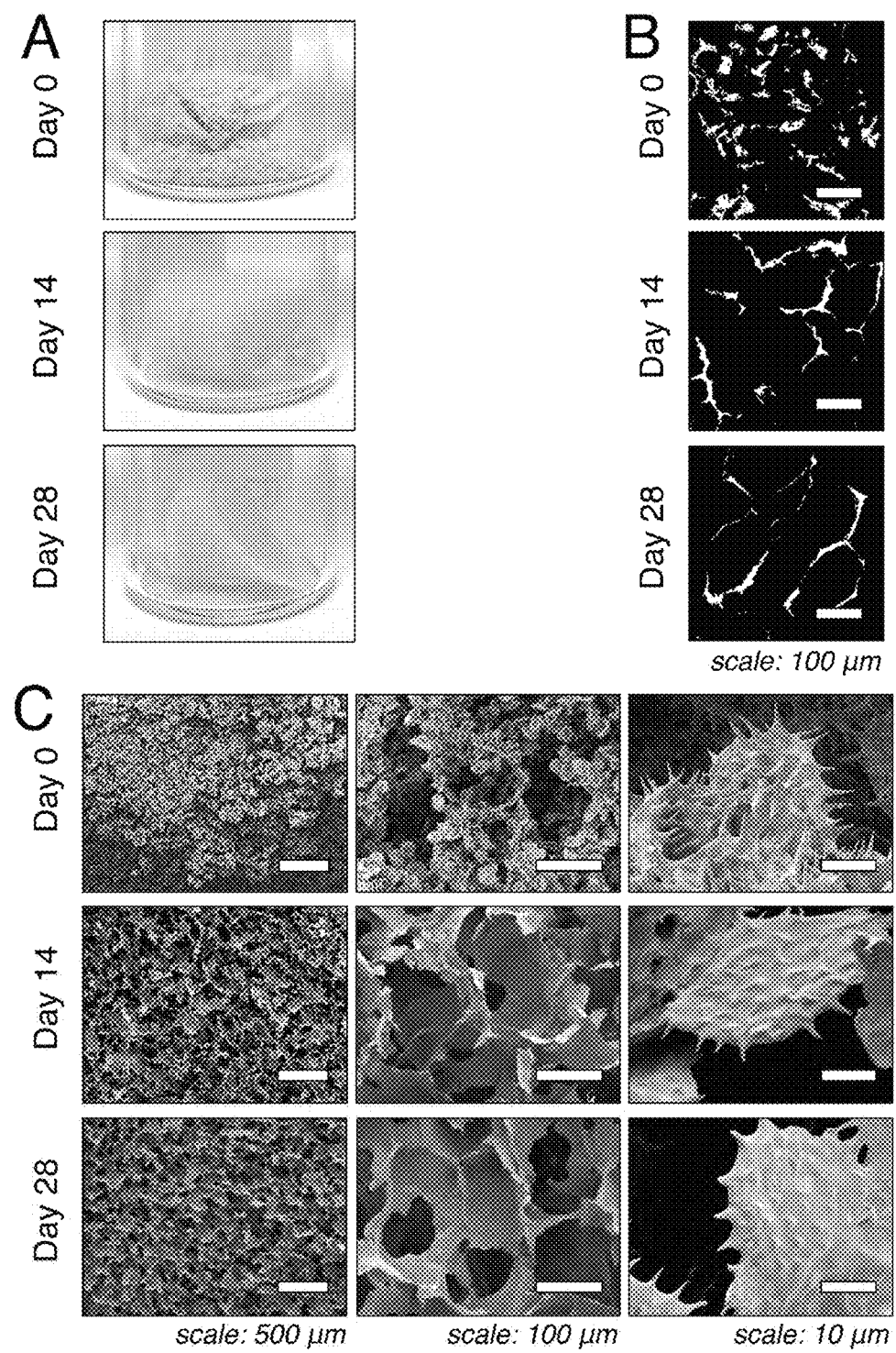
FIG. 8. Characterization of alkaline-treated sunflower pollen sponges with respect to duration of extended KOH incubation. (A) Photographs of sunflower pollen sponges. (B) Confocal laser scanning microscopy (CLSM) cross-section images of sunflower pollen sponges. (C) Scanning electron microscopy (SEM) images of sunflower pollen sponges.
Figure 9:
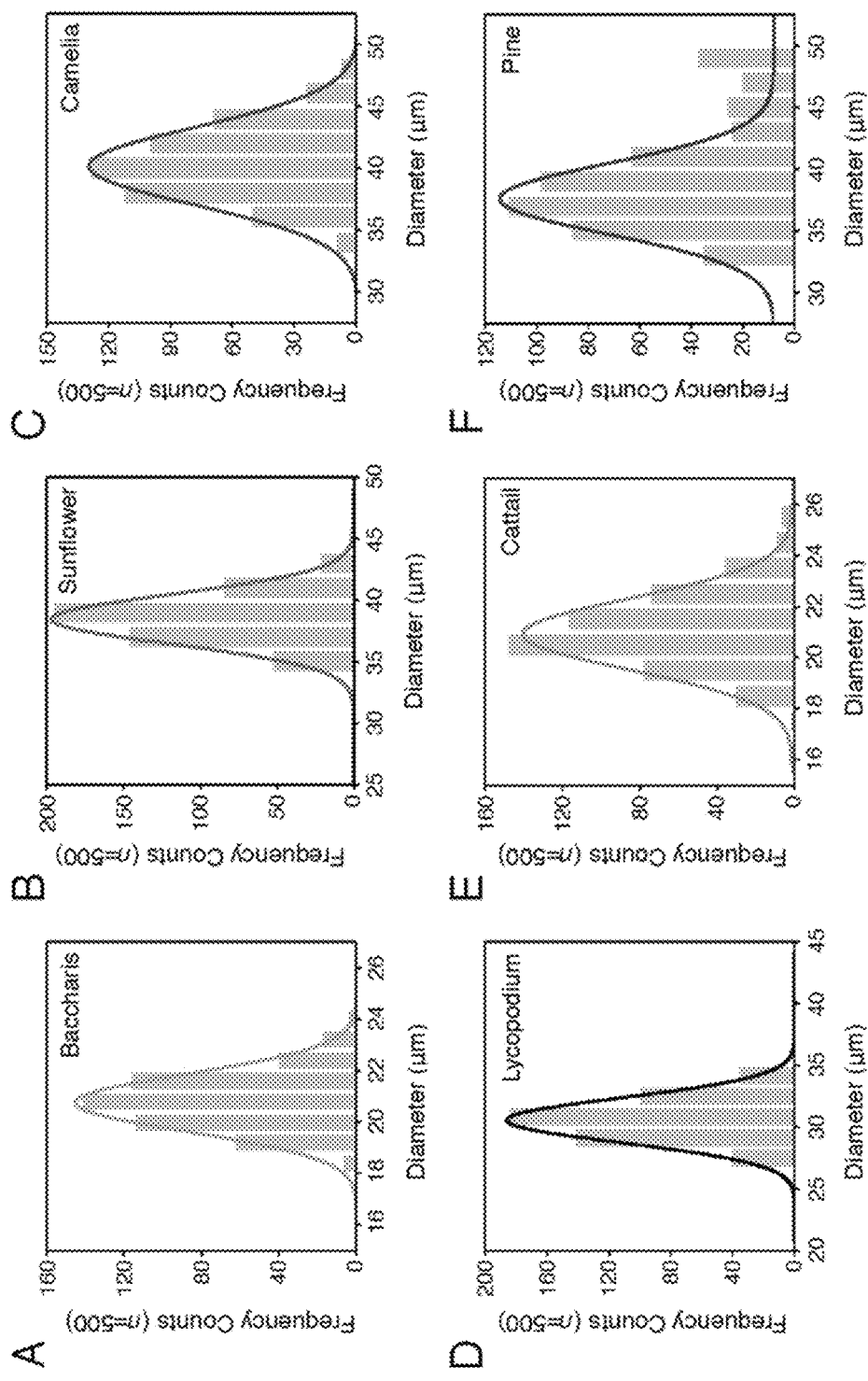
FIG. 9. Particle size distributions of defatted pollen grains from various plant species. The measurements were conducted using dynamic image particle analysis (DIPA) (n=500 particles).
Figure 10:
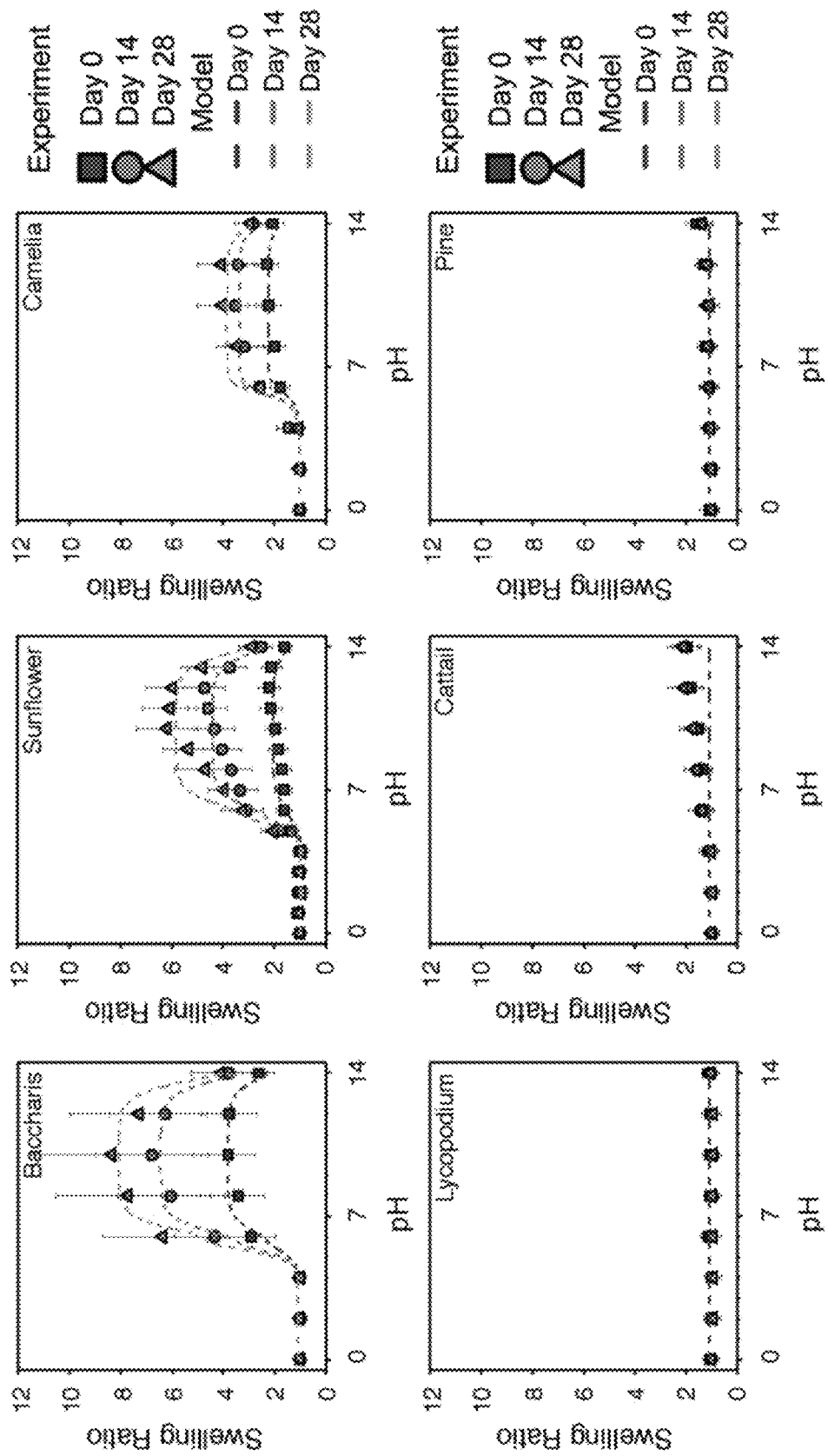
FIG. 10. Experimental swelling data and curve fit of 0-, 14- or 28 day-treated pollen grains as a function of solution pH, compared to unprocessed pollen grains. Dotted lines correspond to theoretical fits of swelling ratios for sporopollenin polymer network. Data depict mean±s.d. (n=50 particles).
Figure 11:
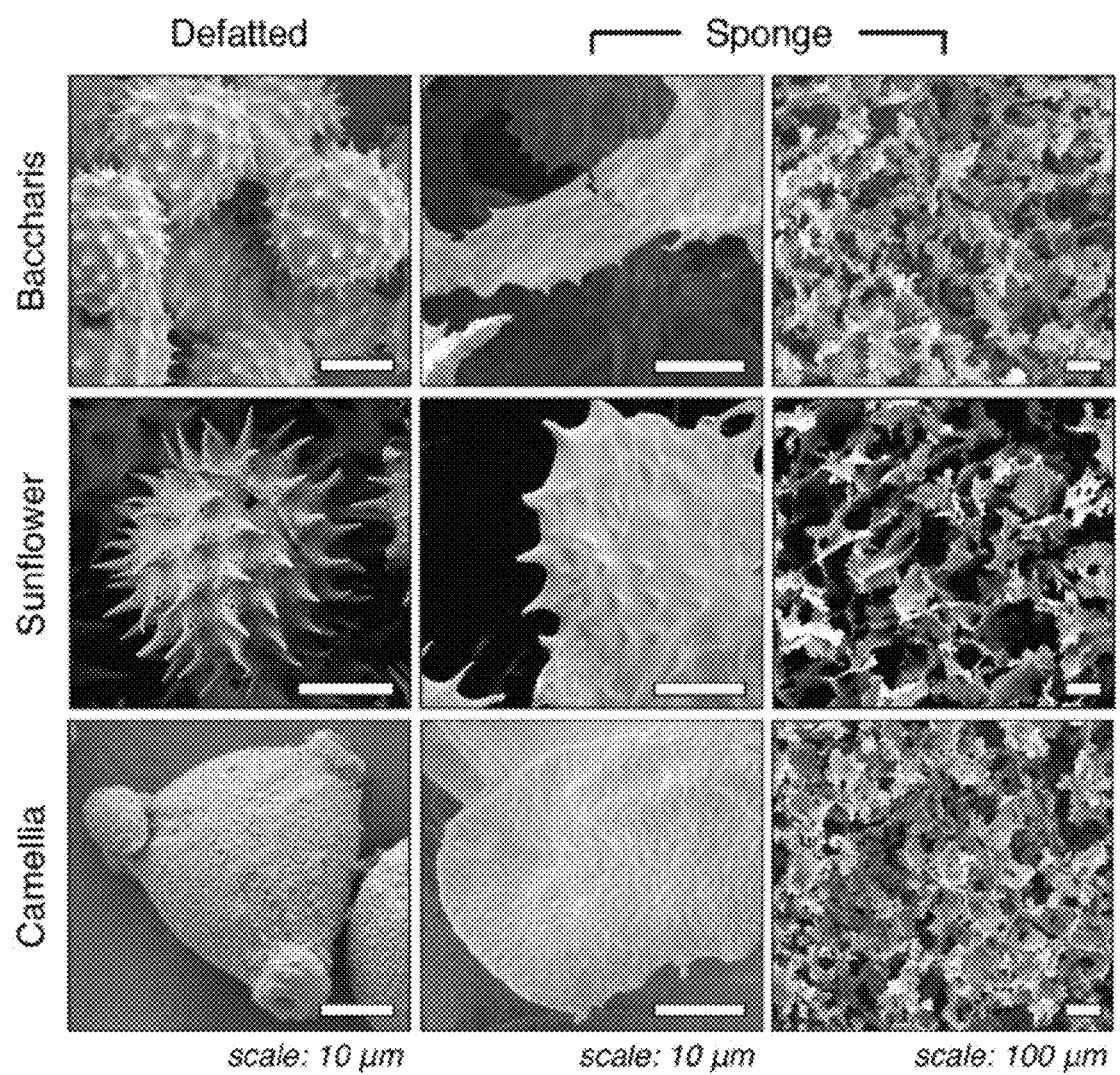
FIG. 11. Profiling gelation properties of different pollen species from the eudicot clade. Representative images of defatted pollen grains before and after alkaline KOH treatment and sponge processing. Results indicate that the tested pollen species all appear to form porous 3D sponges.
Figure 12:
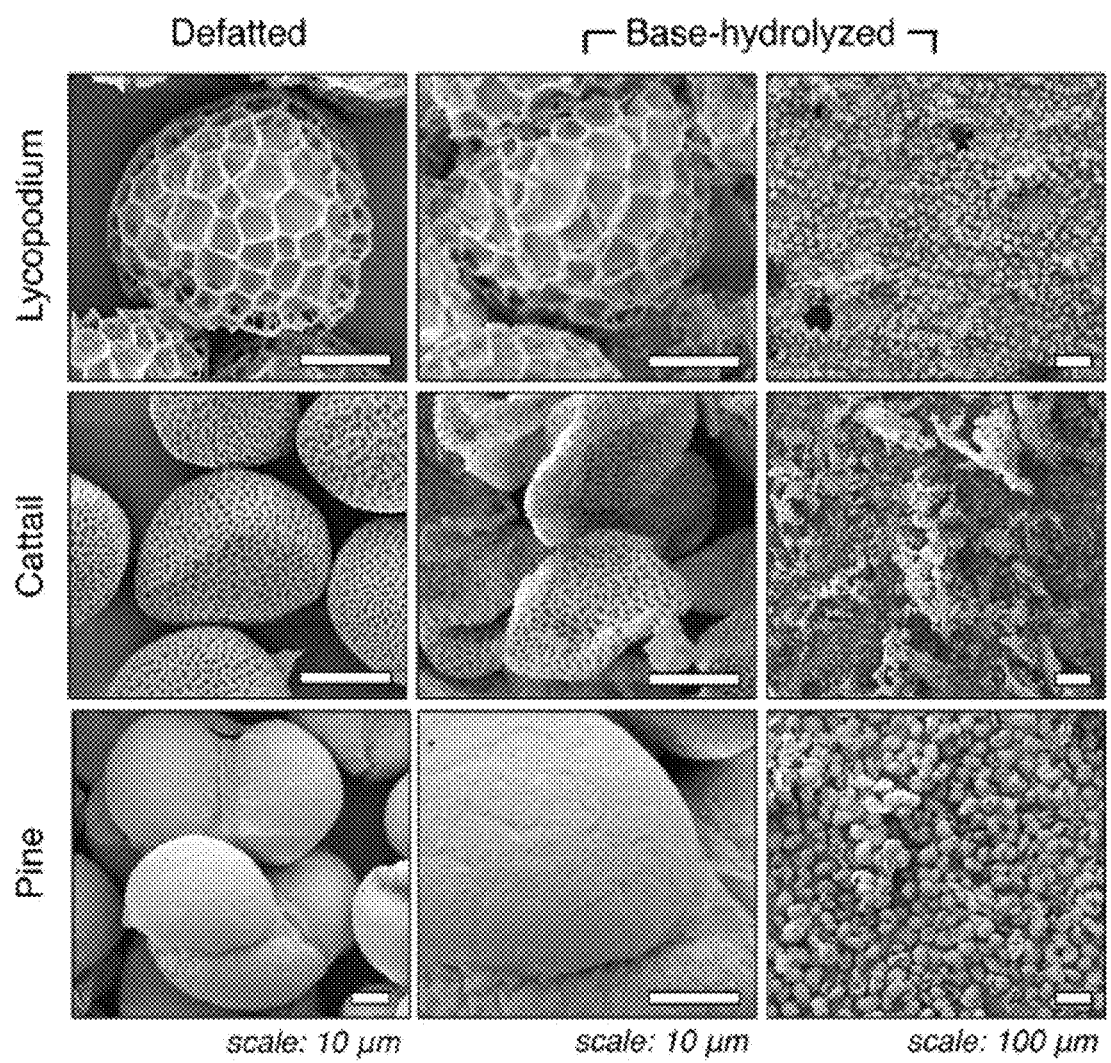
FIG. 12. Profiling gelation properties of additional types of pollen grains and spores from non-eudicot clades. Representative images of defatted pollen grains and spores before and after alkaline KOH treatment and sponge processing. Results indicate that the tested grains and spores do not form microgels and do not yield sponges.
Figure 13:
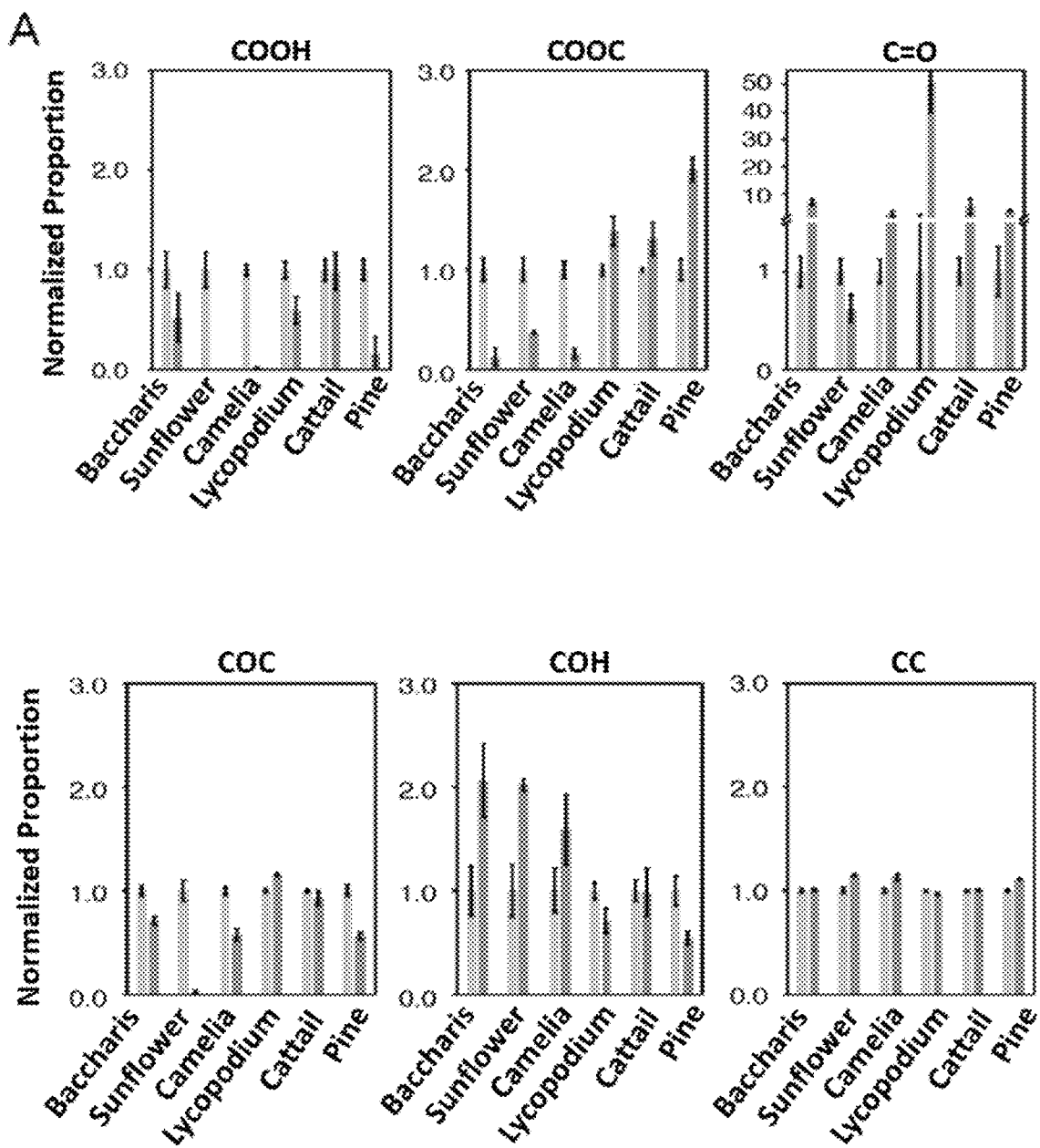
FIG. 13. X-ray photoelectron spectroscopy (XPS) analysis of pollen grains and spores before and after alkaline treatment. (A) Normalized proportional shifts of bond types before and after alkaline treatment. (B) Relative percentage change in bond proportions due to alkaline treatment. Mean±s.d. are reported from 3 independent samples.
Figure 13:
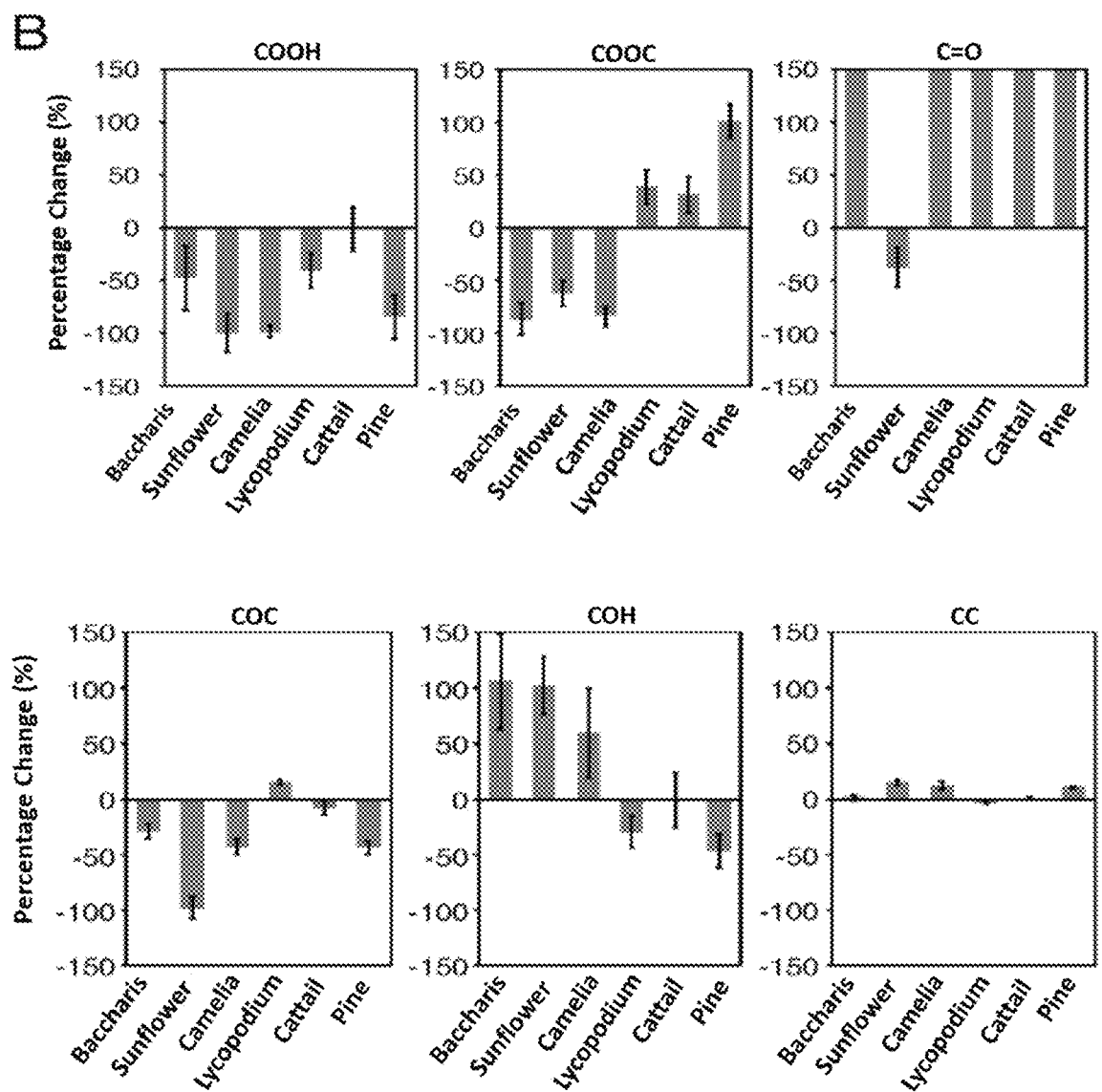
Figure 14:
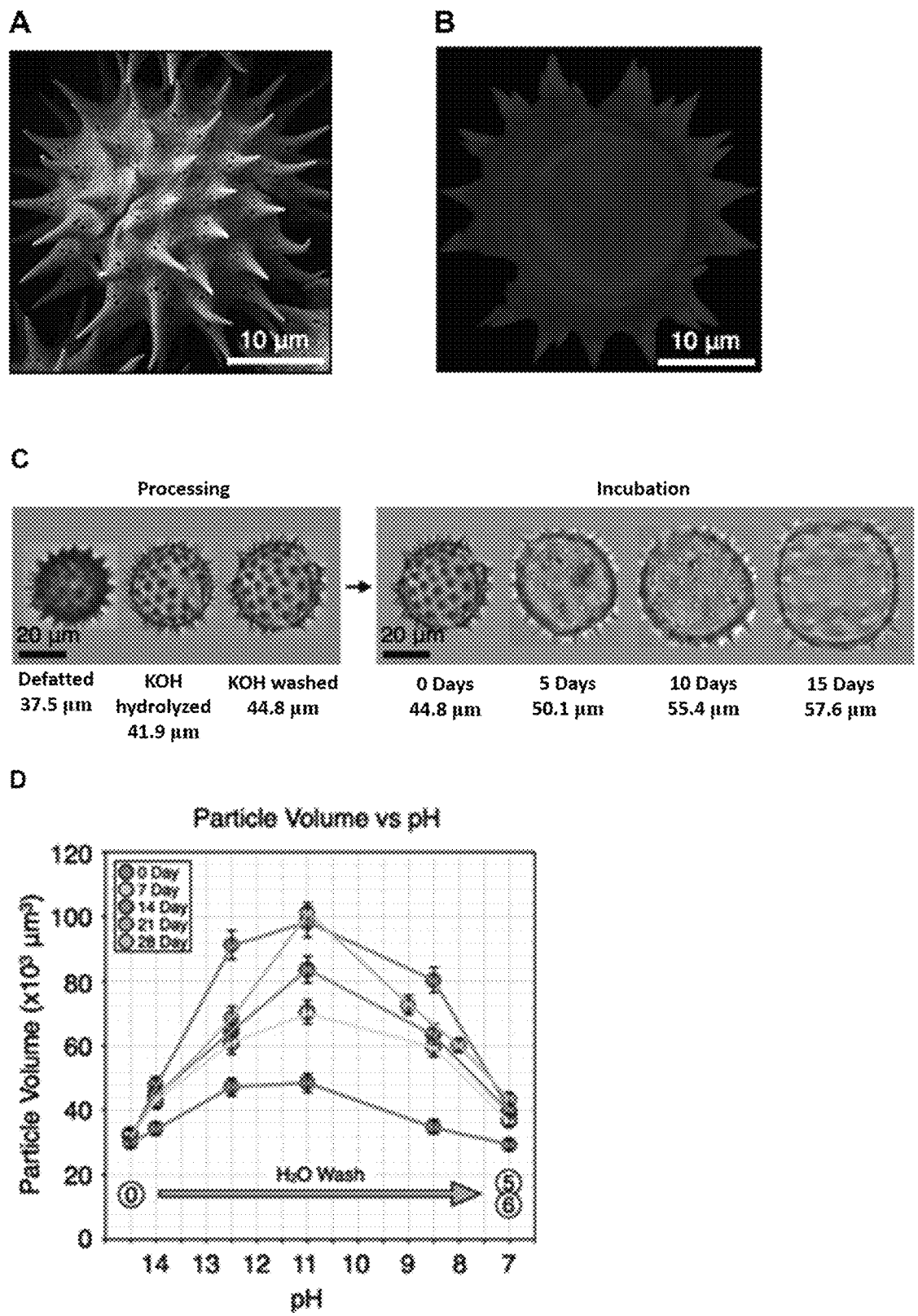
FIG. 14. Sporoderm polymer complex (SPC) microgels. (A) Scanning electron microscopy (SEM) image of *H. annuus* pollen grain. (B) Confocal laser scanning microscopy (CLSM) 3D cross-section of SPC micro-capsule (MC) after cytoplasmic removal. (C) Dynamic imaging particle analysis (DIPA) optical microscopy images of SPC-MCs during washing after various stages of processing and alkaline incubation, and (D) SPC-MC particle volume during washing after various stages of processing and alkaline incubation. (E) SPC-MC spike volume during washing after various stages of processing and alkaline incubation. (F) pH dependent volumetric variation of SPC-MCs after 28-day alkaline incubation, and (G) second derivative analysis of volumetric variation defining five distinct regions. (H) Photograph of SPC-MC gel and CLSM gel cross-section. (I) Shear storage (G') and loss (G") moduli for SPC-MC gel at various stages of incubation measured as a function of shear strain amplitude, $\gamma_0$ ($\gamma=\gamma_0 e^{i\omega t}$). The composite storage modulus curve has been fit to Eq. 4. (J) Yield strain as extracted from the data in panel I, plotted versus $\phi$, with the dotted line representing a fit. Uncertainties are fitting errors.
Figure 14:
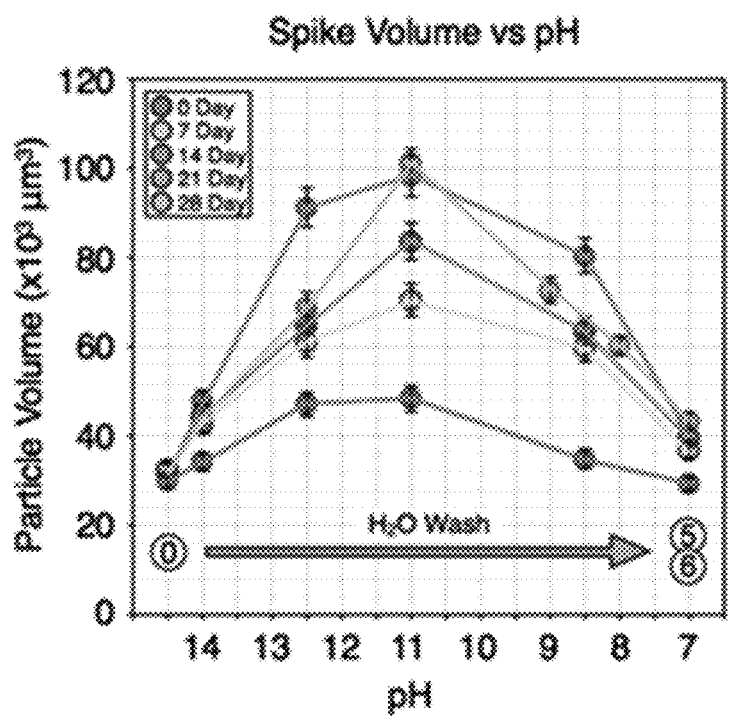
Figure 14:
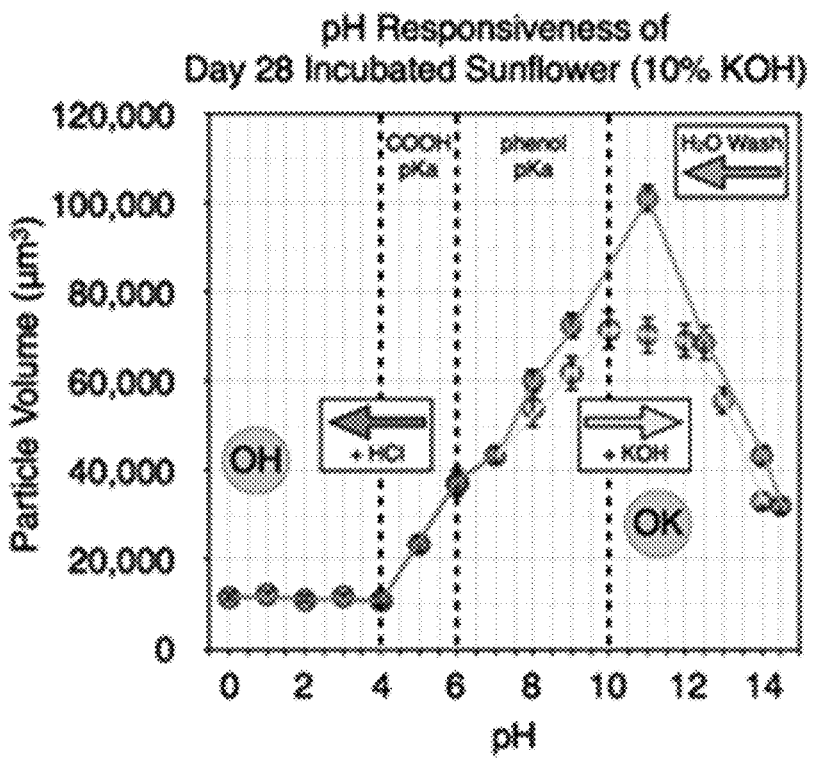
Figure 14:
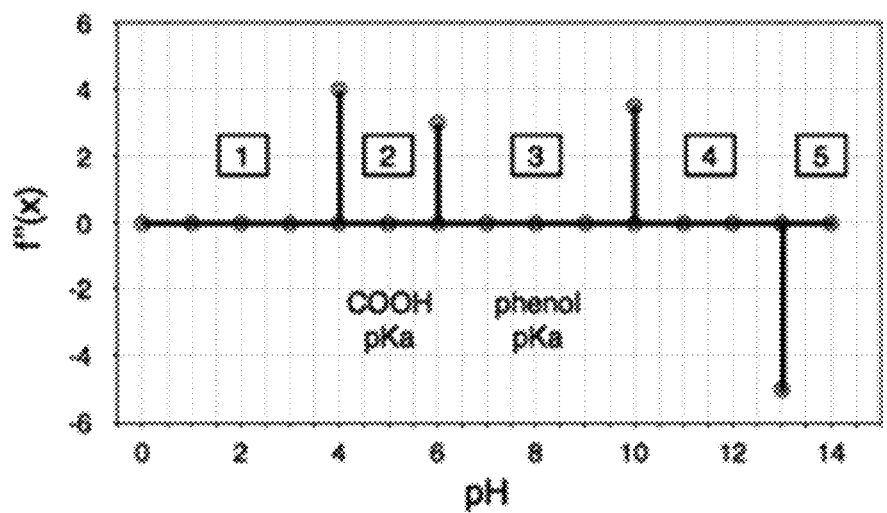
Figure 14:
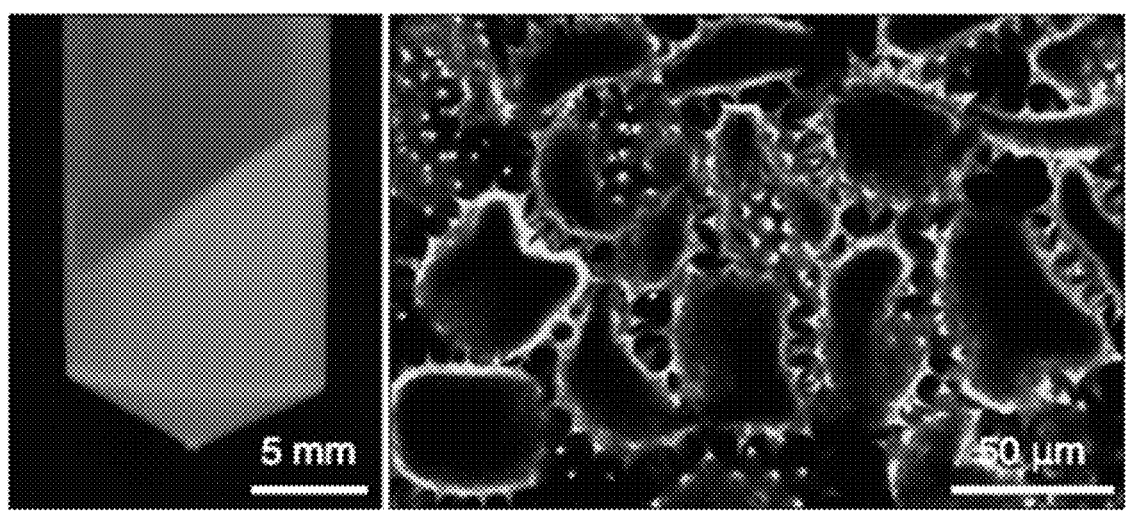
Figure 14:
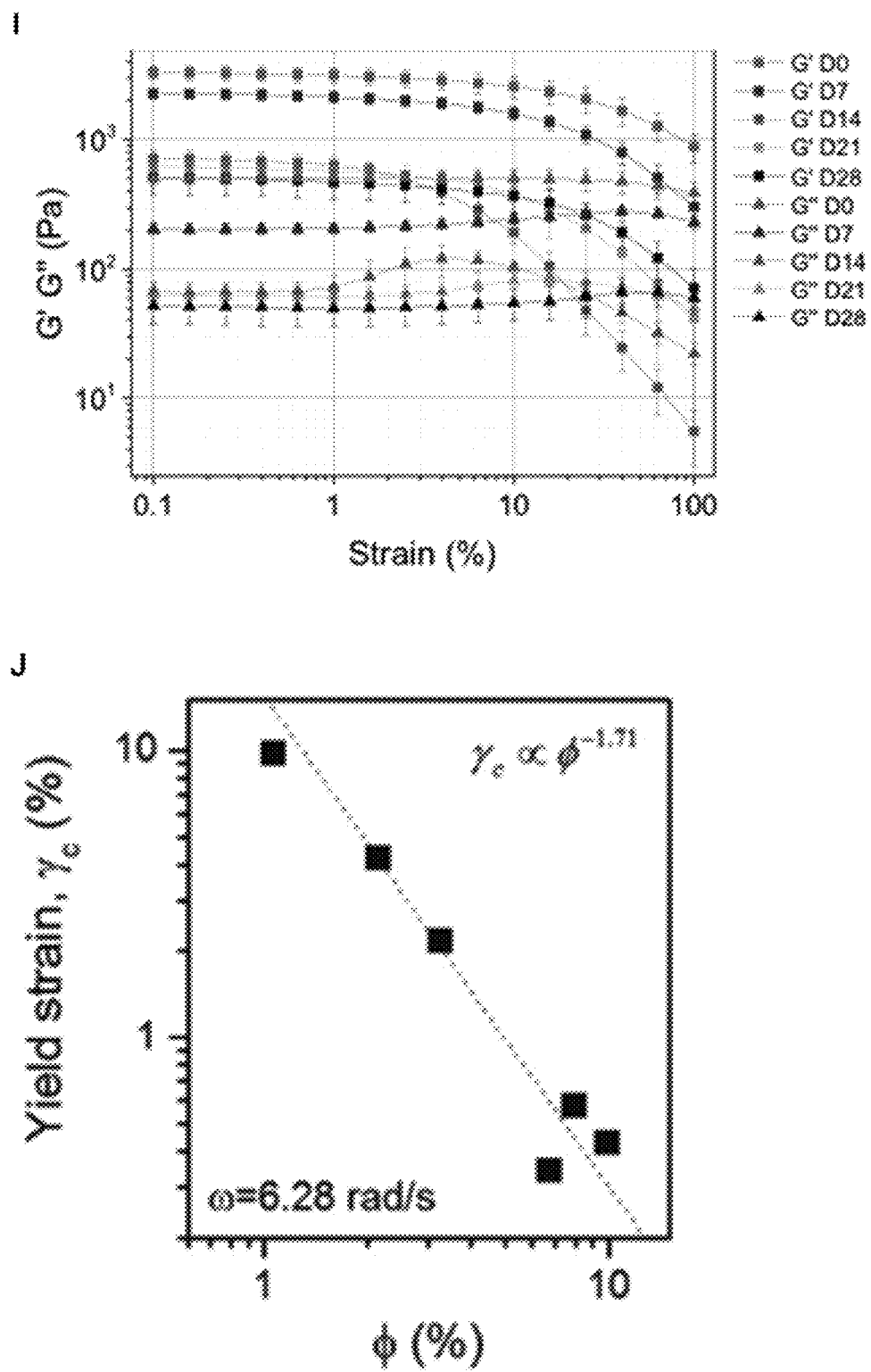

*Helianthus annuus* pollen was used as a representative angiosperm pollen source for the majority of our study due to its interesting tethered-spike morphology (FIG. 1A (*Helianthus annuus*); FIG. 4A (middle); FIG. 5, FIG. 14A, B). The pollen particles were processed by base-hydrolysis in aqueous potassium hydroxide (KOH) solutions, producing porous hollow SPC micro-capsules (SPC-MCs) 37.5±2.2 μm in diameter and devoid of cytoplasmic contents. The SPC-MCs were washed and incubated in aqueous KOH solutions for periods up to 28 days (FIG. 2A, FIG. 14C). At various stages of incubation, the SPC-MCs were washed to pH 7 with water and dynamic imaging particle analysis (DIPA) during washing indicates that increased incubation duration results in increased maximum particle swelling from $4.0\pm0.2\times10^4$ μm³ at day 0 to $10.0\pm0.5\times10^4$ μm³ at day 28. The tethered-spikes of sunflower pollen comprise only sporopollenin with no relation to the cellulosic intine and provide a means to directly observe sporopollenin volumetric variation. Analysis of tethered-spike volume in relation to SPC-MC swelling indicates that spike volumes vary in direct proportion to total capsule volume showing that the *H. annuus* sporopollenin undergoes reversible swelling. However, according to the Flory-Huggins model, the overall polymer density of the SPC decreases relative to incubation time for incubation periods of 0, 7, 14, 21, 28 days.

Detailed analysis of water-washed SPC-MCs in solutions ranging from pH 0 to pH 14 indicate pH-responsive volumetric variations (FIG. 2B, C; FIG. 14D, E), which are consistent with a hollow core-shell microgel system. Derivative analysis of volumetric variation indicates five linear regions (FIG. 2F; FIG. 14F, G). Regions 2 and 3 are consistent with protonation/deprotonation of exposed acidic functional groups resulting in variations of ionic charge, with concomitant osmotic pressure and volumetric variations. Region 5 is consistent with a swollen deprotonated polymeric system shrinking due to charge shielding from high concentrations of salts in solution. Acidic functional groups in a complex binding environment exhibit continuous pKa values of up to four pH units. From pKa's of all moieties present in the SPC system, carboxylic (pKa 4-6) and phenolic (pKa 6-10) moieties present in sporopollenin best explain the volumetric variations observed in regions 2 and 3. Additionally, volumetric variation rates between regions 2 and 3 provide a proportion of 2:1 and reflect the 2:1 ratio of carboxyl:phenolic moieties as proposed for sporopollenin oligomeric units.

Figure 3:
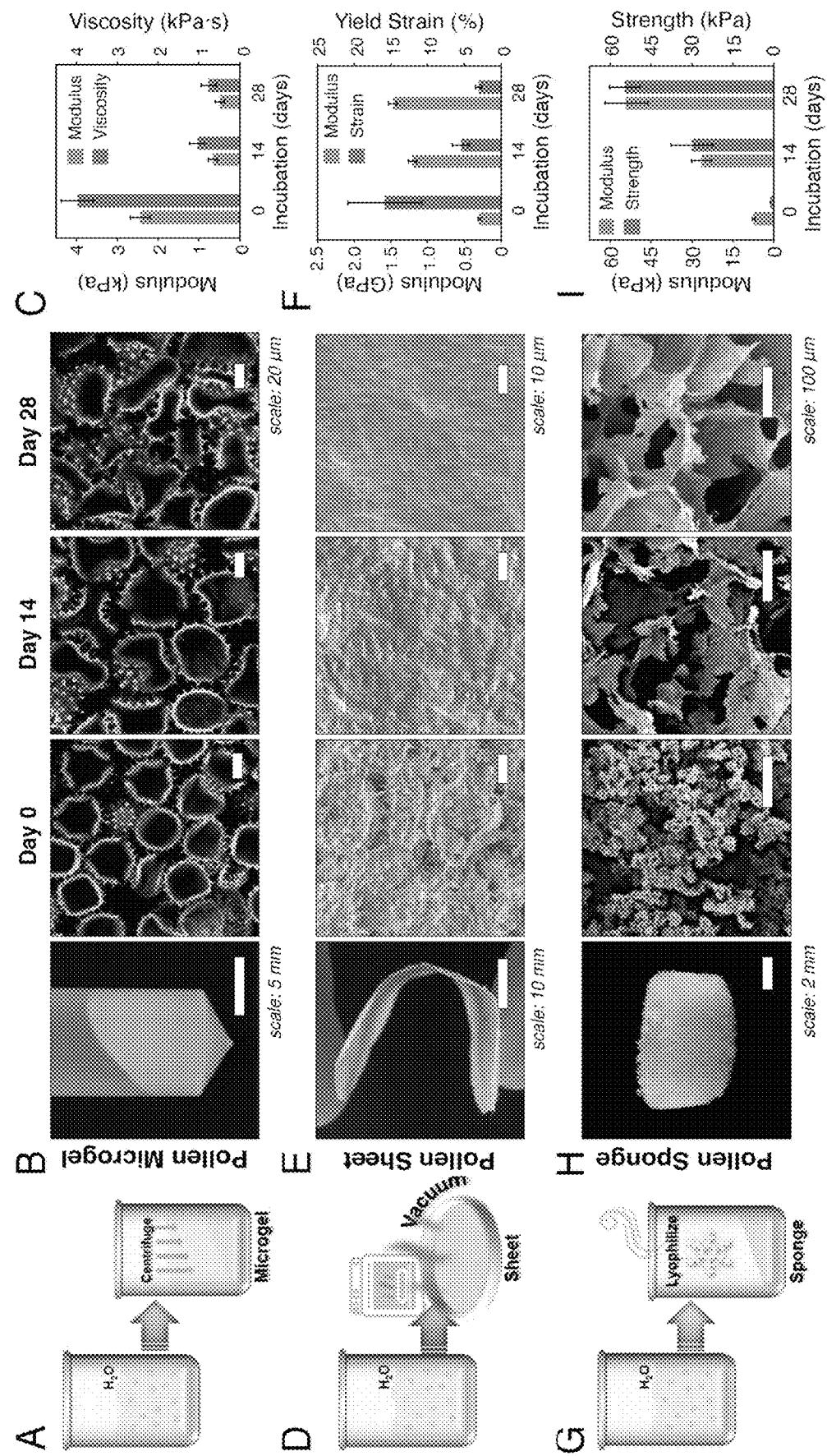
FIG. 3 illustrates the microstructural characterization and mechanical behavior of soft-matter systems derived from microgel building blocks. (A) Schematic illustration of microgel formation. (B) Optical and cross-sectional CLSM images of pollen microgel building blocks produced from 0, 14 and 28 day-treated pollen grains. (C) Storage moduli and viscosity of 3 vol % pollen microgel dispersions at 0.1 Hz. (D) Schematic illustration of sheet formation. (E) Optical and surface SEM images of fabricated sheets derived from 0, 14 and 28 day-treated pollen grains. (F) Tensile moduli and yield strain of pollen-derived sheets. (G) Schematic illustration of sponge formation. (H) Optical and cross-sectional SEM images of fabricated sponges derived from 0, 14 and 28 day-treated pollen grains. (I) Compressive moduli and compressive strength of pollen-derived sponges. Data in C, F, and I depict mean±s.d. (n=5 independent samples).

The water washed SPC-MCs gel was further processed by centrifugation and excess water was removed to obtain viscous gels with weight contents of 3.1±2.0% SPC-MCs and 96.9±2.0% water (FIG. 3A, B, FIG. 14H). Rheological analysis of the SPC-MC gels indicates visco-elastic properties varying with incubation period (FIG. 3C; FIG. 14I), and are consistent with standard models of soft particles in solution wherein particle integrity is decreased. Shown in FIG. 14I, J are plots of storage (G') and loss (G") modulus versus oscillatory strain amplitude, $\gamma_0$. Although both G' and G" decrease with incubation period, the G' versus ϕ behavior can be analyzed via the basic SGR (soft-glassy rheology) model proposed by Sollich et al. ("Soft glassy rheology." In *Molecular Gels*, pp. 161-192. Springer, Dordrecht, 2006) which ascribes a distribution of potential wells for the individual gel elements and accounts for deformation of the material in overcoming the potential wells. As expected the data follow a power law with an exponent 2.5±2.2.

Although G' tends to fall with increasing strain amplitude, G" remains relatively stable, resulting in crossing at high strain for periods of 14, 21, and 28 days incubation. For particulate gel systems, this is known as the SWP (Soft Wobbly Particle) effect and has been explained by the motion of soft particles being greater than the particle size leading to slippage in the system. This model fits the data extremely well. Extracting $\gamma_c$ and plotting versus ϕ in FIG. 14J shows a power law with exponent −1.71±0.3. Combining the fits in FIGS. 14I and J allows estimation of dB=1.4±0.2 and dN=1.6±0.2, which is similar to softening of alginate microgel systems but somewhat smaller than the values of ~2 found for softening of cellulose microgel systems.

Figure 15:
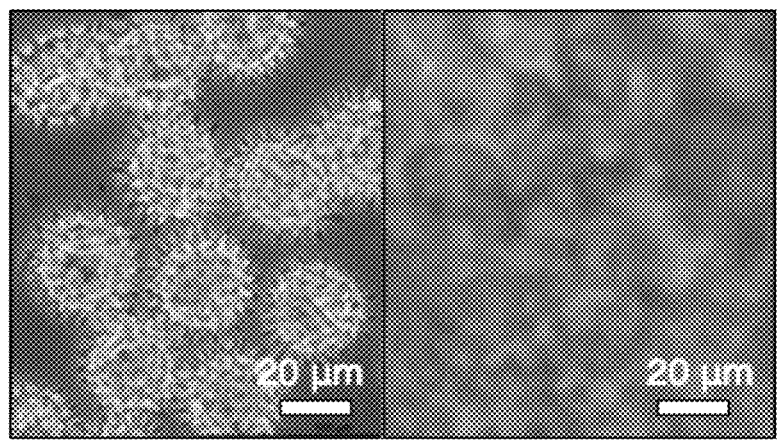
FIG. 15. Analysis of convection dried SPC-microgels. (A) Optical microscope images of SPC-MCs in water and dried agglomerates. (B) SEM images of SPC sheet and interparticle binding. (C) Photographs of SPC sheets from various alkaline incubation periods. (D) Optical microscope images of light transmission through SPC sheets. (E) Relative light transmittance through SPC sheets. (F) Proportions of RGB light in transmitted light from SPC sheets and (G) RGB proportion intensity shifts. (H) Proportion of polarized light rotated 90° during transmission through SPC sheets.
Figure 15:
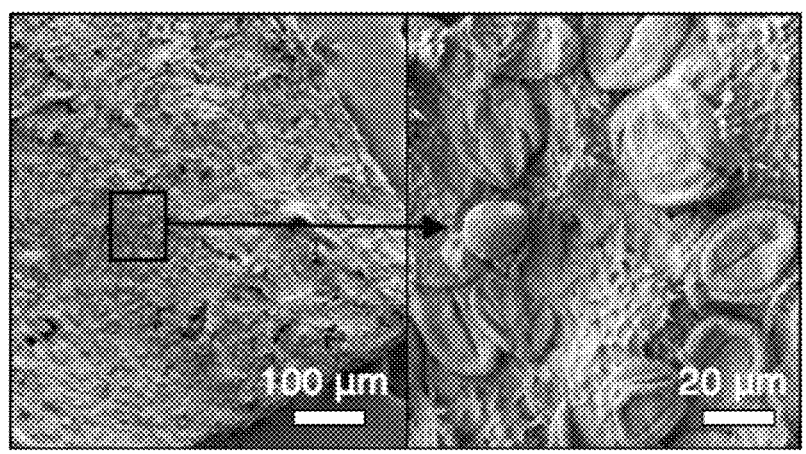
Figure 15:
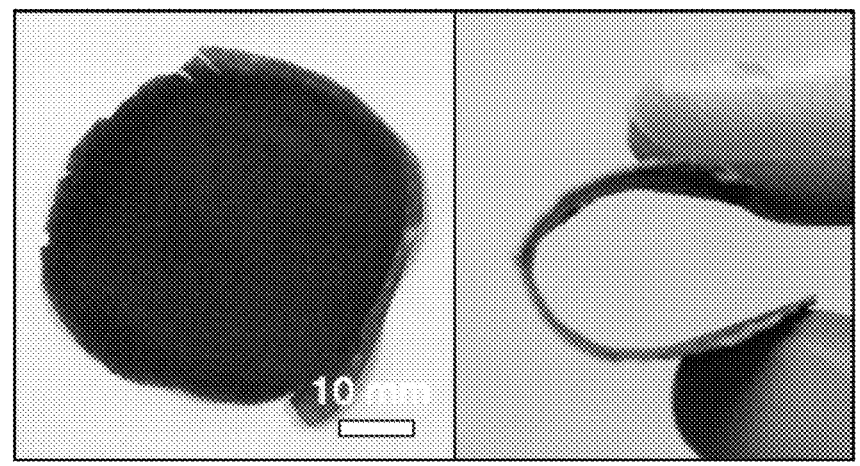
Figure 15:
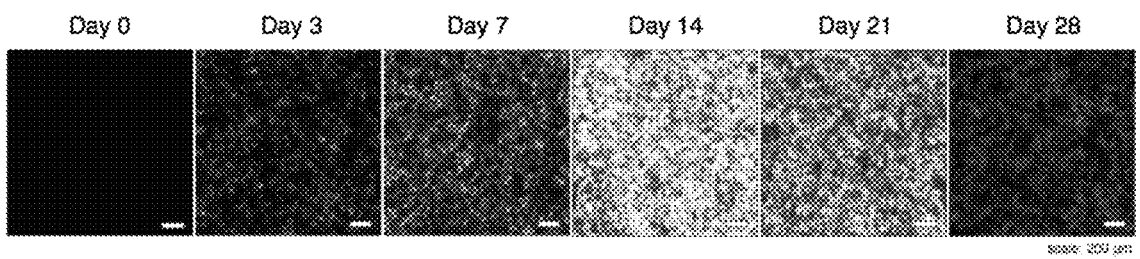
Figure 15:
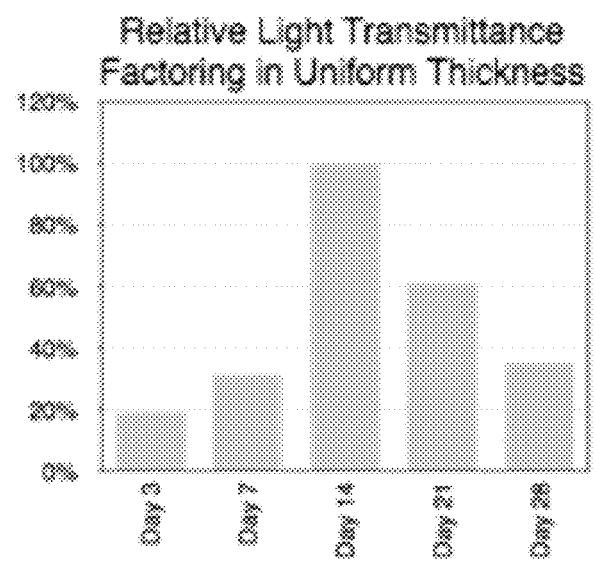
Figure 15:
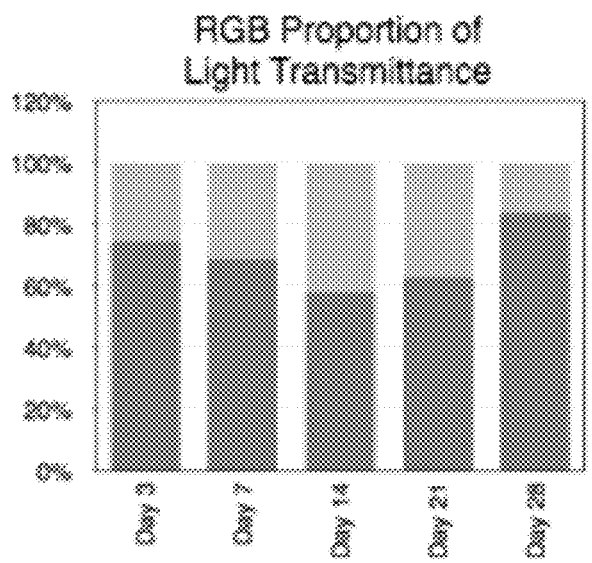
Figure 15:
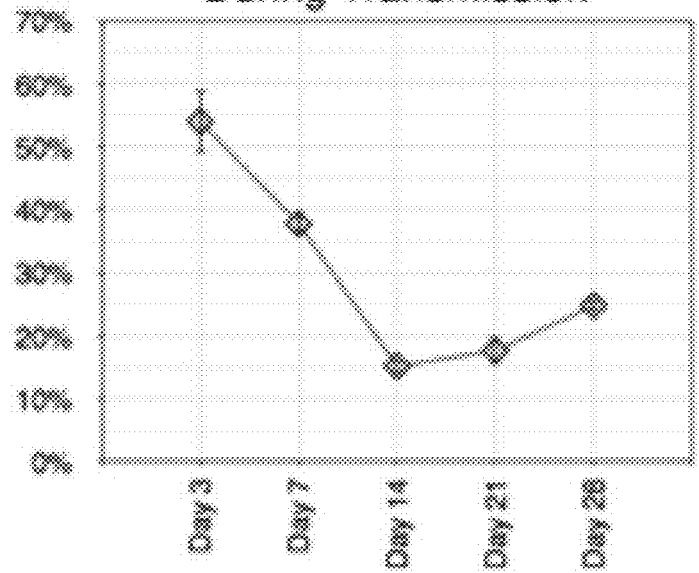
Figure 15:
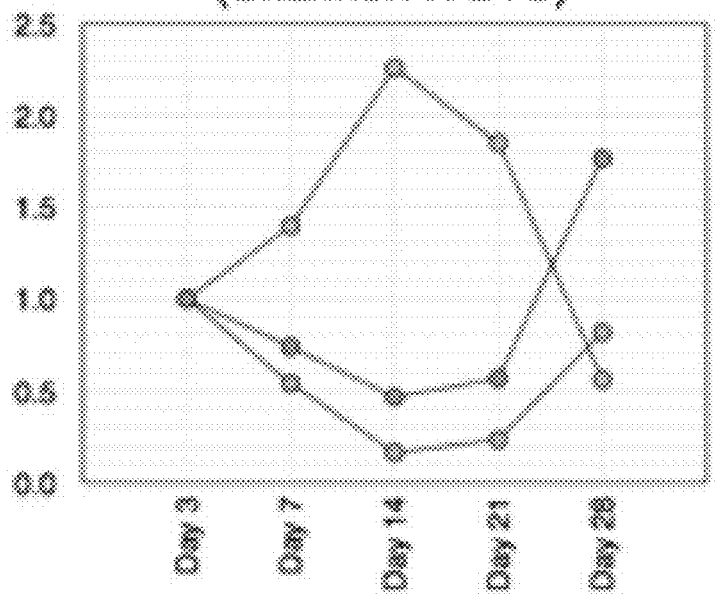

Inter-particle binding is observed when water washed SPC-MCs are dried under convection drying conditions (FIG. 15). Vacuum filtration and drying of washed day 0 to 28 SPC-MCs results in flexible SPC sheets (FIG. 15C). Sheets form with cracks at days 0, 3, and 7, and at day 28 the sheet volume is reduced by 40% compared to day 21. Dried micro-gel systems comprising cellulose have been observed to form solid agglomerates, with binding attributed to inter-particle hydrogen bonding due to the presence of carboxyl surface functional groups. Analysis of light transmittance through the SPC sheets indicates an increase from 0% for the day 0 sample to a relative maximum of 100% at day 14, and a decrease to 37.5±2.1% at day 28 (FIG. 15E). As light transmission is inversely proportional to polymer crystallinity, the SPC is exhibiting reductions in crystallinity to day 14, followed by increases in crystallinity at days 21 and 28. Further analysis of transmitted light composition indicates reductions in red and blue proportions up to day 14 followed by stabilization at day 21 and increases at day 28 (FIG. 15F). Red and blue shifts in light transmission from polymers undergoing increases in crystallization has been attributed to the restructuring of various polymeric structures and is well documented in polymer literature. Polarized light transmission is also reduced up to day 14 and increases at days 21 and 28 (FIG. 15G) indicating reductions and increases of polymer crystallinity. Based on DSC and XRD analysis, the degree of crystallization variation could be estimated to be from 70% at day 0 to 20% at day 14, and 40% at day 28.

Porous sponge-like structures form when SPC-microgel systems are frozen and lyophilized (FIG. 16A). Pollen particle morphology reduces from day 0 to day 14 whereupon smooth pore walls are formed and sponge morphology remains similar for days 21 and 28. Lyophilized SPC-microgel samples were analyzed by Attenuated total reflection-Fourier-transform infrared spectroscopy (ATR-FTIR) to determine general trends in SPC bond degradation. Peak height ratio analysis of ATR-FTIR data identified relative decreases in molecular bond proportions from day 0 to day 14, with stabilization and increases at days 21 and 28 for all major peaks (FIG. 16B). Height ratios were taken relative to the most stable spectra peak, being 1062 cm$^{-1}$ for $H.$ $annuus$ under 10% KOH solution conditions and attributable to a-cellulosic compounds. This trend supports the overall degradation of SPC up to day 14 followed by SPC restructuring.

Averaging total shifts in relative peak height proportions across all incubation periods and major peaks for each of 10%, 20%, 30%, 40%, and 50% $KOH_{aq}$ processing conditions indicates increased total reductions from 10% to 30% $KOH_{aq}$ with decreased reductions at 40% and inhibition at 50% $KOH_{aq}$ (FIG. 16C). This trend indicates an alkaline assisted hydrolytic degradation process. Increasing concentrations of aqueous alkaline solutions has been shown to inhibit degradation in polymer systems due to a lack of bulk water phase $H_2O$ molecules required for hydrolysis.

The generality of alkali-assisted hydrolytic degradation for various SPC sources was explored with 10% $KOH_{aq}$ for an additional 8 plant species, comprising 5 angiosperms: $Baccharis$; $Camellia$; dandelion; ragweed; and rapeseed, and 3 non-angiosperms commonly studied in sporopollenin research literature: cattail; $Lycopodium$; and pine. Four of the five additional angiosperms exhibit ATR-FTIR peak height degradation trends similar to sunflower (FIG. 16D) and result in the formation of porous sponge materials upon gelation, freezing, and lyophilization (FIG. 16E). One angiosperm and the 3 non-angiosperm sourced pollens indicated no significant major peak degradation from FTIR analysis, and upon processing resulted in a powdery discrete particle agglomeration rather than a stable porous sponge.

Normalization of the FTIR spectra to the aromatic B peak at (1512 cm$^{-1}$) and comparison of the 1300 to 1800 cm$^{-1}$ region, highlights that the pollen species which exhibit degradation, gelation, and binding characteristics have a high degree of polymer structural similarity (FIG. 16F). Curve fitting analysis of all pollen species explored shows a close fit for gelated pollens and high variance for non-gelated pollens. Based on this data, the potential for alkali-assisted hydrolytic degradation of the SPC appears to be a general phenomenon that occurs among a wide range of, but not all, pollen species. The similarity of FTIR spectra for the gelling pollens in the 1300 to 1800 cm$^{-1}$ region suggests a high degree of similarity in polymer structure and provides an easy means to screen for other potentially gelling pollen types.

Example 2: Sample Preparation

Alkaline Treatment Processing. Pollens were prepared by defatting in diethyl ether and base-hydrolysis in 30 w/v % $KOH_{aq}$. Defatting was performed by adding pollen (2 g) to a polytetrafluoroethylene (PTFE) round bottom flask with diethyl ether (20 ml) with a 2 cm stirring bead and stirring (200 rpm, 12 h). The defatted pollen was separated using a vacuum filtration flask, and then dried in a fume hood (12 h) followed by removal of residual solvents in a vacuum oven until stable weight (6 h). Base-hydrolysis was performed by adding defatted pollen (2 g) to a PTFE round bottom flask with $KOH_{aq}$ (20 ml; 1%, 10%, or 25 (w/v) %) with a 2 cm stirring bead, followed by uniformly dispersing the pollen by stirring (750 rpm, 2 min), and then heating (80° C., 200 rpm, 2 h). The base-hydrolyzed pollen suspension was transferred to a 50 ml Falcon tube, then centrifuged (4500 rpm, 5 min). The supernatant was removed and the sample was topped up to 20 ml with fresh $KOH_{aq}$ of the same concentration used for the initial base-hydrolysis step. The mixture was vortexed at high speed (2 min), followed by centrifugation (4500 rpm, 5 min). The $KOH_{aq}$ washing was repeated for a total of 5 times. Finally, fresh $KOH_{aq}$ was added up to a total of 20 ml, followed by vortexing at high speed (2 min), and the sample was left to sit at room temperature (25° C.) to incubate for a duration of 0, 14, or 28 days.

Fabrication of Microgel. The pollen microgel was prepared by vortexing (2 min) the $KOH_{aq}$ suspension to ensure uniform mixing, and aliquoting the suspension (2 ml) into a 15 ml falcon tube for water washing. The aliquoted suspension was topped up to 10 ml with distilled water and vortexed at high speed (2 min), followed by centrifugation (4500 rpm, 5 min). The supernatant was removed and measured for pH. If the supernatant pH was greater than 7.5, the tube was topped up to 10 ml with distilled water, followed again by vortexing and centrifugation. The water washing was typically repeated for a total of 4 to 6 washes to achieve neutral pH (~7.5). The remaining base-hydrolyzed and water-washed pollen was transferred to a 2 ml vial using a 3 ml disposable dropper, and topped up to 2 ml with distilled water and vortexed briefly to mix. The suspension was centrifuged (14000 rpm, 5 min) and the supernatant was removed. The centrifugation and supernatant removal process was repeated for a total of 3 times, so as to remove as much free water as possible. Wet samples were used within 4 hours of preparation for morphological analysis of the bulk microgel by CLSM, and rheological analysis of the bulk microgel.

Fabrication of Sheet. Pollen sheets were prepared by vortexing (2 min) the $KOH_{aq}$ suspension to ensure uniform mixing, aliquoting the suspension (20 ml) into a 50 ml falcon tube, centrifugation (4500 rpm, 5 min) with removal of supernatant, then addition of warm water (20 ml, 50° C.), vortexing, transfer to a glass beaker, and the addition of more warm water (130 ml, 50° C.). The suspension was stirred (5 min) and then the water was removed via vacuum filtration using a nylon mesh (10 μm) as the filter. The pollen was recovered into a glass beaker and topped up to 150 ml with water followed by stirring (5 min). The washing and vacuum filtration steps were repeated until the aqueous pollen suspension reached neutral pH (~7.5). After the final filtration step the thin pollen film was allowed to dry by running the vacuum pump (10 min), and convection drying in a fume hood (48 h). Finally, the dried pollen sheet was removed from the nylon mesh and further dried by exposure to a low vacuum environment (10 mbar) until stable weight (~6 h). The dried samples were stored in a dry cabinet until further characterization.

Fabrication of Sponge. The pollen sponge was prepared by vortexing (2 min) the $KOH_{aq}$ suspension to ensure uniform mixing, and aliquoting the suspension (2 ml) into a 15 ml falcon tube for water washing. The aliquoted suspension was topped up to 10 ml with distilled water and vortexed at high speed (2 min), followed by centrifugation (4500 rpm, 5 min). The supernatant was removed and measured for pH. If the supernatant pH was greater than 7.5, the tube was topped up to 10 ml with distilled water, followed again by vortexing and centrifugation. The water washing was typically repeated for a total of 4 to 6 washes to achieve neutral pH (~7.5). The remaining base-hydrolyzed and water-washed pollen was transferred to a 2 ml vial using a 3 ml disposable dropper, and topped up to 2 ml with distilled water and vortexed briefly to mix. The suspension was centrifuged (14000 rpm, 5 min) and the supernatant was removed. The centrifugation and supernatant removal process was repeated for a total of 3 times, so as to remove as much free water as possible. The tube was covered with parafilm, and needle holes were added, then additional filter paper was taped over the parafilm to ensure no pollen particles could come out during lyophilization. The covered tube was frozen (12 h, −20° C.) and lyophilized (24 h) until stable weight. The lyophilized samples were stored in a dry cabinet until further characterization.

Characterization Methods

Scanning Electron Microscopy (SEM). Scanning electron microscopy was performed for analysis of pollen surface and cross-section morphology, pollen sheet morphology, and pollen sponge morphology. Samples were sputtered with gold (~10 nm thickness) prior to analysis and analyzed in a JSM 7600F (JEOL, Akishima, Tokyo, Japan) system. For cross-section morphological analysis, samples were applied to carbon tape, dipped in liquid nitrogen for 5 min, and multiple cuts were made across the sample coated tape with a diamond edged scalpel.

Elemental Analysis. Elemental analysis of bulk samples was performed with a Vario EL III CHN elemental analyzer (Elementar Analysensysteme GmbH, Langenselbold, Hesse, Germany) with appropriate calibration standards. Samples were dried until stable weight (5 mg) and analyzed. Percent nitrogen was multiplied by 6.25 to estimate the weight percent of protein (AOAC, Official methods of analysis of AOAC International, G. W. Latimer, Ed. (AOAC International, Rockville, Md., US, Ed. $20^{th}$, 2016)).

Rheometry. Bulk microgels samples were tested on a Physica MCR 501 rheometer (Anton Paar, Graz, Styria, Austria) with a CP25-1/TG, 24.990 mm diameter cone plate attachment. Gel samples (70 µl) were applied to the rheometer stage by a pipette tip cut to a nozzle diameter of ~3 mm. Standard rheological property cone-plate analysis was performed (A. Y. Malkin, A. I. Isayev, *Rheology: concepts, methods, and applications*. (Elsevier, 2017)). Viscosity measurements were performed over a shear rate range of 0.1 to 500 1/s. Frequency sweep measurements were performed over a frequency range of 0.1 to 10 Hz at a strain amplitude of 0.5%. Strain sweep measurements were performed over a strain range of 0.1 to 100% at a frequency of 1 Hz.

Mechanical Analysis. Tensile and compressive mechanical testing was performed with a DMA Q800 (TA Instruments, New Castle, Del., USA) to determine tensile properties of pollen sheets and compression properties of pollen sponges (C. M. Yakacki, S. Willis, C. Luders, K. Gall, Deformation Limits in Shape-Memory Polymers. *Advanced Engineering Materials* 10, 112-119 (2008)). For tensile analysis, pollen sheets (20 mm×5 mm) were clamped in place and a force was applied at a rate of 2 N/min until material failure to obtain stress/strain curves. For compression analysis, pollen sponges (9 mm×2 mm) were positioned centrally between compression plates and a compression force was applied at a rate of 1.5 N/min to a maximum force of 18 N to obtain stress/strain curves. Data was processed with Universal Analysis 2000 software (TA Instruments, New Castle, Del., USA).

Dynamic Image Particle Analysis. Dynamic image particle analysis was performed on samples for defatted pollen particle characterization and for pH responsive volumetric variation of microgel particles based on standard analysis methods (R. C. Mundargi et al., Eco-friendly streamlined process for sporopollenin exine capsule extraction. *Scientific reports* 6, 19960 (2016)). Samples were analyzed in benchtop FlowCamVS (Fluid Imaging Technologies, Scarborough, Me., USA), with a 200 µm flow cell, and a 10× or 20× lens. The system was calibrated with polystyrene microspheres (50±1 µm) to ensure optimal focus and settings. Particle characterization of defatted pollens was conducted with aqueous suspensions of pollen (2 mg/ml). For pH responsive volumetric variation studies, neutral pH microgel samples (pH 7) were modified down to an acidic pH (pH 0 to pH 6) by the addition of HCl, or up to a basic pH (pH 8 to pH 14) by the addition of KOH. Each sample suspension (115 µl, 2 mg/ml) was primed into the flow cell before running. The flow rate was set to 0.25 ml/min, the run volume was set to 0.1 ml, and image capture rate was set to 15 images/s, to obtain an efficiency of 12.4%. The optical settings were: brightness 100, contrast 40, sharpness 6, and gain 400. Particle diameter measurements are based on at least 50 well focused particles. All studies were performed in triplicate and data is presented as representative of triplicate batches.

Optical Microscopy. Time-lapse optical microscopy was performed to determine morphological variations and rates of pH responsive swelling and deswelling for microgel particles. Samples were analyzed in an inverted optical microscope (Nikon Corporation, Shinagawa, Tokyo, Japan) with a 20× lens, and images were captured every 0.64 s up to 21.59 s. Neutral pH microgel samples (20 µL, 12.5 mg/ml) were placed in the centre of a 2×2 cm nylon mesh (300 µm mesh size) in a petri dish, and covered with a glass slide. To achieve volumetric shrinking, pH 2 HCl solution (500 µL) was added to the dish and allowed to flow into the nylon mesh network, whereas pH 12 KOH solution (500 µl) was added to achieve volumetric swelling.

X-Ray Photoelectron Spectroscopy (XPS). Analysis was conducted based on standard XPS methodologies (J. F. Watts, J. Wolstenholme, An introduction to surface analysis by XPS and AES. *An Introduction to Surface Analysis by XPS and AES*, by John F. Watts, John Wolstenholme, pp. 224. ISBN 0-470-84713-1. Wiley-VCH, May 2003, 224 (2003)). Wide scan (160 eV) and narrow scan (20 eV) X-ray photoelectron spectroscopy was performed on defatted and base-hydrolyzed pollens. Samples were deposited on carbon tape (5 mm×5 mm) adhered to a silicon wafer, then dried using a freeze drier (12 h) before analysis. Samples were analyzed using an AXIS Supra (XPS) surface analysis instrument (Kratos Analytical Ltd, Stretford, Greater Manchester, England) equipped with a monochromatic Al/Mg X-ray source (225 W, $2 \times 10^{-9}$ mbar). Spectra were obtained using an aluminum anode (Al Kα=1491.600 eV) and charge neutralization. Data was processed using ESCApe software (Kratos Analytical Ltd, Stretford, Greater Manchester, England).

Atomic Force Microscopy (AFM). AFM force spectroscopy was performed to estimate Young's modulus of defatted and base-hydrolyzed pollen (T. Young et al., The use of the PeakForce™ quantitative nanomechanical mapping AFM-based method for high-resolution Young's modulus measurement of polymers. *Measurement Science and Technology* 22, 125703 (2011)). A commercial AFM system (Park Systems Corp., Suwon, Gyeonggi-do, South Korea) with an inverted optical microscope (Nikon Corporation, Shinagawa, Tokyo, Japan) was used for all AFM measurements. pH neutral microgel was spread on a polyethylene petri dish and analysis was performed on individual particles. The center position of pollen was confirmed by inverted optical microscopy, and then force spectroscopy was performed at that point using AFM. Force-distance curves were recorded at 20 random points for each particle analyzed, and three particles were analyzed for each sample. A commercial AFM cantilever (Biolever mini, Olympus, Shinjuku, Tokyo, Japan) with a nominal spring constant of approximately 0.09 N/m was used. The AFM cantilever was cleaned using ethanol and exposed to UV light for 30 min to remove contamination on the AFM cantilever and tip. Before and after force spectroscopy, the spring constant of the AFM cantilever was calibrated by monitoring the thermal vibration of the AFM cantilever (approximately 0.1126 N/m). The Young's modulus was obtained from the force-distance curves by adopting a Hertz model for curve fitting, and Young's modulus was calculated by a commercial SPM data analysis program (XEI, Park Systems Corp., Suwon, Gyeonggi-do, South Korea), a custom analysis program (in Python), and Origin Pro 9.1 (OriginLab Corp., Northampton, USA). It was assumed that the AFM tip shape is a four-sided pyramid with a half cone angle $\alpha'$, so that the force on the cantilever F is expressed as $$F = \frac{E}{1-v^2} \frac{\tan \alpha}{\sqrt{2}} \delta^2 \tag{1}$$

where E is the Young's modulus, v is Poisson's ratio, and $\delta$ is the indentation (depth). v and a were set to be 0.5 and 35°, respectively. The speed of the AFM cantilever approach and retraction were set to be 1,200 nm/s with a maximum loading force of 3 µN.

Confocal Laser Scanning Microscopy (CLSM). CLSM was performed to determine microgel particle morphology and pollen sponge morphology based on the autofluorescence of pollen shell constituents (C. Pöhlker, J. A. Huffman, J.-D. Förster, U. Pöschl, Autofluorescence of atmospheric bioaerosols: spectral fingerprints and taxonomic trends of pollen. *Atmospheric Measurement Techniques* 6, 3369-3392 (2013)). Microgel samples (20 µl) were applied to a thin glass slide by a pipette tip cut to a nozzle diameter of ~3 mm. A drop (20 µl) of lens oil was added to the top of the gel samples to ensure that the sample did not lose moisture during analysis. Pollen sponges were placed on a thin glass slide for imaging. CLSM imaging was performed with an LSM 710 confocal microscope (Carl Zeiss, Oberkochen, Baden-Wurttemberg, Germany). Imaging was performed successively with three laser excitation channels: 405 nm, 488 nm, and 561 nm, with three respective emission filters: 416-477 nm, 498-550 nm, 572-620 nm. A 10× or 20× optical lens was used for imaging and at least three images were obtained per sample. Images were processed using ZEN software (Zen Software Ltd, Rochdale, Greater Manchester, England) and ImageJ software.

Model of Pollen Microgel Swelling Effect

After alkaline treatment, some pollen species exhibited hollow core-shell microgel-like properties and pH-responsive swelling behavior. Based on the experimental data, the pH-responsive swelling behavior of pollen microgels was explored through curve fitting with the constitutive model of a pH-sensitive hydrogel, proposed by Drozdov et al. (A. Drozdov, J. deClaville Christiansen, Modeling the effects of pH and ionic strength on swelling of polyelectrolyte gels. *The Journal of chemical physics* 142, 114904 (2015)) and Ricka et al. (J. Ricka, T. Tanaka, Swelling of ionic gels: quantitative performance of the Donnan theory. *Macromolecules* 17, 2916-2921 (1984)) with polyelectrolyte (PE) gels (R. Skouri, F. Schosseler, J. P. Munch, S. J. Candau, Swelling and Elastic Properties of Polyelectrolyte Gels. *Macromolecules* 28, 197-210 (1995). S. K. De et al., Equilibrium swelling and kinetics of pH-responsive hydrogels: models, experiments, and simulations. *Journal of Microelectromechanical Systems* 11, 544-555 (2002)). The basic model describes the overall pH-responsive behavior of a hydrogel system, also capturing its deswelling behavior at high pH conditions. In the constitutive model, pollen systems consist of three key phases: i) solid from covalently crosslinked network of sporopollenin polymer chains, ii) solvent from water, and iii) solutes from mobile ions. Also, it was assumed that the pH of water is varied by adding only monovalent salts, hydrochloric acid (HCl) and potassium hydroxide (KOH). To describe the swelling behavior of a pollen microgel, the following conditions were set for equilibrium swelling.

1) Chemical potentials of water and four solutes ($H^+$, $K^+$, $OH^-$, $Cl^-$) in a gel and in the bath satisfy the following relations:

$\mu = \bar{\mu}$, $\mu_{H^+} = \bar{\mu}_{H^+}$, $\mu_{K^+} = \bar{\mu}_{K^+}$, $\mu_{OH^-} = \bar{\mu}_{OH^-}$, $\mu_{Cl^-} = \bar{\mu}_{Cl^-}$ 2) Cauchy stress (T) induced by volume change due to swelling becomes zero for a specimen with a traction-free boundary surface:

$$T = -\Pi I + \frac{1}{1+Q}[W_{eq,1}B_e - J_{e3}W_{eq,1}B_e^{-1} + (J_{e3}W_{eq,1} + J_{e3}W_{eq,1})I] = 0,$$

where $W_{eq}$ is the elastic energy at equilibrium with principal invariants, $J_{e1}$, $J_{e2}$, $J_{e3}$ and the Cauchy-Green, tensor, $B_e$, $\Pi$ is an arbitrary function, and Q is the degree of swelling.

Using those key equilibrium conditions, the following two equations are derived in terms of two variables, the degree of swelling Q, and the concentration of positively charged mobile ions X.

$$X\left[X - \frac{Q_b}{Q}\alpha\right] = \frac{1}{\kappa^2}(10^{-pH} + [K^+])^2 \tag{S1}$$

$$\ln\frac{1}{1+Q} + \frac{1}{1+Q} + \frac{x}{(1+Q)^2} +$$

$$\frac{g}{1+Q}\left[\left(\frac{1+Q}{1+q_0+\bar{q}\alpha}\right)^{\frac{2}{3}} - 1\right] - \frac{1}{X}\left(X - \frac{1}{\kappa}(10^{-pH} + [K^+])\right)^2 = 0 \tag{S2}$$

$$\alpha = K_a'\left(K_a' + \frac{10^{-pH} + R[K^+]}{10^{-pH} + [K^+]}X\right)^{-1} \tag{S3}$$

$$[K^+] = 10^{pH-14} - 10^{-pH} \tag{S4}$$

$$K_a' = \kappa K_a, \tag{S5}$$

where $K_a = 10^{-pK_a}$ and $\kappa = 1000/18$ (molarity of water). At a given pH, $[K^+]$ is determined from the equation (S4). Eight material constants are fitting parameters to solve equations (S1) and (S2): (i) dimensionless elastic modulus, g, (ii) acid dissociation constant, $K'_a$, (iii) volume fraction of functional groups in the initial state, $Q_b$, (iv) the ratio of dissociation constants for hydroxylated functional groups and ion pairs, R, (v) the Flory-Huggins parameter, $\chi$, (vi) the reference state of a gel with non-ionized functional groups, $q_0$, and (vii) the evolution of the stress-free state of polymer chains induced by their ionization, $\bar{q}$, which is highly dependent on the average molecular weight between cross-linkers. To reduce the number of fitting parameters, $q_0=0$, and $\chi=0.35$ were set, assuming the water is a common good solvent of pollen microgels.

The nominal stiffness of polymer chains, g, can be determined at low pH where a gel is not ionized. Since all the pollen microgels exhibited almost the same swelling ratios at low pH (pH<4) regardless of different KOH treatment time, g=0.3~0.4 provided the best fit, indicating that the chain stiffness did not change under the strongly basic conditions. $pK_a$ and $Q_b$ are related to the onset of pH-sensitive swelling associated with the ionization of polymer chains over pH changes. The ionized carboxyl groups of sporopollenin chains begin to induce swelling of pollens around pH 4, which could be captured at $pK_a=4.5$ for Camellia and $pK_a=6$ for Sunflower and Baccharis. Changes of $pK_a$ and $Q_b$ did not appear from changes in the duration of alkaline treatment. Moreover, the swelling ratios of a pollen microgel reach the maximum around pH 7-12 and then decrease after pH 12, addressed by R, where ion pairs start being formed due to an abundance of hydroxide ions, leading to decreased water uptake.

Finally, the overall swelling ratios of the three pollen microgels were best-fit by varying $\bar{q}$. The longer the duration of alkaline treatment, the larger $\bar{q}$ is required to be to optimize fitting. Thus, the swelling behavior of pollen microgels is highly dependent on the length of chain segments linked to $\bar{q}$. The larger $\bar{q}$ values directly correlate with increased average molecular weight between cross-linkers, implying that the cross-linking density of the network reduces with increasing alkaline treatment duration. Since the base-hydrolysis of pollen sporopollenin is shown to mostly cleave the ester and ether bonds and generate hydroxyl functional groups, the total number of carboxyl groups should remain almost constant. Also, the generated hydroxyl groups likely have high pKa >10. (42) The effect of those hydroxyl groups on swelling should be negligible under lower pH conditions (pH 4-10). Instead, the cleavage of the ester and ether groups decreased the cross-linking density, resulting in longer chain segments in between the reduced number of cross-linkers. Best-fit modelling parameters show good agreement with the XPS analysis characterizing the chemical bonds in the pollen microgel system, providing an understanding of the swelling mechanism through a structure-property relationship.

Therefore, from model fitting to experimental results with parameter estimations, two important structural features of the sporopollenin network in pollen systems after alkaline treatment were identified. First, alkaline treatment does not appear to induce sizeable chemical and mechanical changes of sporopollenin backbones, preserving the inherent chain characteristics (e.g., chain stiffness, volume fraction, $pK_a$ of functional groups). Second, the alkaline treatment cleaves cross-linking ester and ether bonds of the sporopollenin network, reducing the cross-linking density, yet increasing the length of chain segments in between cross-linkers, which leads to the enhanced swelling behavior of pollen gels.

TABLE S1

Best-fit parameter estimations to describe pH-dependent swelling behavior of pollen microgel particles from various plant species within eudicot clade.

| Plant Species | KOH treatment (Day) | Fitting parameters | | | | | Best fit |
|---|---|---|---|---|---|---|---|
| | | g | $pK_a$ | $Q_b$ | R | $\bar{q}$ | $R^2$ |
| Sunflower | 0 | 0.38 | 6 | $2 \times 10^{-10}$ | $1.5 \times 10^{-6}$ | 1.15 | 0.84 |
| | 14 | | | | | 3.65 | 0.95 |
| | 28 | | | | | 4.80 | 0.94 |
| Camellia | 0 | 0.35 | 4.5 | $5 \times 10^{-10}$ | $2 \times 10^{-5}$ | 1.24 | 0.92 |
| | 14 | | | | | 2.50 | 0.94 |
| | 28 | | | | | 3.00 | 0.93 |
| Baccharis | 0 | 0.3 | 6 | $2 \times 10^{-10}$ | $1.5 \times 10^{-6}$ | 2.85 | 0.95 |
| | 14 | | | | | 5.55 | 0.98 |
| | 28 | | | | | 7.20 | 0.95 |

Example 3: Write-In and Write-Out with Pollen Microgels

Materials Defatted sunflower (*Helianthus annuus* L.) pollen was purchased from Greer Labs (USA). Potassium hydroxide (KOH) was purchased from Sigma-Aldrich (Singapore).

Preparation of the sunflower pollen gel Sunflower pollen (2 g) was mixed with aqueous 10 or 30 (w/v) % KOH (20 mL) in a 100 ml PTFE round bottom flask under magnetic stirring at 400 rpm. The suspension was refluxed for 2 h at 80° C. with stirring at 200 rpm. The suspension was transferred to a 50 ml falcon tube, then centrifuged at 4500 rpm for 5 min. The supernatant was removed and the sample was topped up to 40 ml with fresh KOHaq of the same concentration used for the initial base-hydrolysis step. The mixture was vortexed at high speed for 2 min, followed by centrifugation at 4500 rpm for 5 min. The KOHaq washing was repeated for 5 times. Finally, fresh KOHaq was added up to 40 mL, followed by vortexing at high speed for 2 min, and the sample was left to sit at hot plate oven at 80° C. for a setting time (e.g. 3 hours, 6 hours, 12 hours).

Dynamic image particle analysis Dynamic image particle analysis was performed in a bench-top FlowCAM SYSTEM with a 200 μm flow cell, and a ×10 lens. The system was calibrated with 50 μm polystyrene beads (BRAND) to ensure optimal focus and settings. Pollen gel samples (7 μL) was well dispersed in media (180 μL) (e.g. water or electrolyte solution) and then loaded into the sample funnel. Sample was drawn into the flow chamber by a pump at a speed of 0.25 mL/min. When pollen particles passing through the laser fan has sufficient laser light scatter, the camera was triggered to capture an image of the field of view at an interval of 15 images/s with an efficiency of 12.4%. The optical settings were: brightness 100, contrast 40, sharpness 6, and gain 400. The pollen particles properties such as particle number, particle edge gradient, particles circularity, et al., are then saved by a software named VisualSpreadsheet (USA). Particle analysis measurements are based on at least 300 well focused particles. All studies were performed in triplicate and data is presented as representative of triplicate batches.

Optical Microscopy pH and ion responsive behavior of pollen microgel was observed by using a Time-lapse optical microscopy with a ×20 lens, and images were captured every 0.74 s up to 120 s. For the study of pollen microgel pH responsive behavior, the pollen gel sample (10 μL) was firstly diluted in deionized water (40 μL), then dropped on a 0.5×2 cm nylon mesh (150 μm mesh size), which was fixed in the middle of a glass slide (75.5 mm×25.5 mm). Then the glass slide was attached onto sticky-slide I Luer (75.5 mm×25.5 mm) (ibidi, Germany) with a 60 μL channel (50 mm in length, 5 mm in width). The sticky-slide I Luer was connected with a tubing pump (REGLO Digta) by two silicone tubes. For pH responsive study, pH 2 HCl solution and pH 14 KOH solution was allowed to flow through the channel at the speed of 300 μL/min. The morphology was photographed at a frequency of 1 time/s. For $Ca^{2+}$ responsive study, 10 mM $CaCl_2$) solution and 10 mM EDTA solution was pumped through the channel at the speed of 300 μL/min. The frequency of the camera was set as 2 times/s.

Fourier-transform infrared (FTIR) spectroscopy The sunflower pollen gel samples was frozen at −20° C. for 12 hours then lyophilized in a freeze dryer for 2 days. FTIR measurements were conducted using a PerkinElmer Spectrum (Seer Green, Buckinghamshire, UK) with a diamond cell attenuated total reflection (ATR) accessory. Reflectance infrared spectra were collected at 4000-650 $cm^{-1}$, with 16 scans per measurement, and 3 replicate measurements per sample. Background spectra were collected prior to sample readings and automatically subtracted from each measurement. Baseline correction was carried out using the Spectrum 10 software (Seer Green, Buckinghamshire, UK). Following baseline correction, each spectrum was standardized as follows: Briefly, $(x-\bar{x})/\sigma$ values were used, where x refers to the absorbance value, $\bar{x}$ to the spectrum arithmetic mean and σ to the spectrum standard deviation.

Confocal Laser Scanning Microscopy (CLSM) Sunflower pollen gel samples (about 20 μL) were dropped onto a thin glass slide. A drop (20 μl) of lens oil was added to the top of the gel samples to ensure that the sample did not lose moisture during analysis. CLSM imaging was performed with a Carl Zeiss LSM710, Jena, Germany. Imaging was performed successively with three laser excitation channels: 405 nm, 488 nm, and 561 nm, with three respective emission filters: 416-477 nm, 498-550 nm, 572-620 nm. A ×20 optical lens was used for imaging and at least three images were obtained per sample. A laser scan speed of 67 seconds per each phase (1024×1024: 84.94 μm2 sizes) was used in conjunction with plane mode scanning of pixel dwell 12.6 μs. To obtain the 2D images, the mid region of the pollen particles was imaged. The 3D images were constructed by the CLSM z-stack function staring from the bottom layer of the pollen particles and ending at the layer 40 μm far from the bottom layer.

Rheometry Rheological properties of prepared pollen microgels were determined via oscillatory measurements on a stress-controlled rheometer (MCR 501, Anton Paar, Graz, Austria) at 25° C. in a cone/plate geometry (angle 4°/diameter 50 mm, 0.5 mm gap). For each test, 75 μl of prepared microgel or microgel-alginate samples was loaded onto the stage. Strain sweep, frequency sweep, and time sweep tests were performed in triplicates. Strain sweeps were performed by increasing the strain logarithmically from 0.1% to 100% at a frequency of 6.28 rad/s (1 Hz). The linear viscoelasticity (LVE) region of the microgels were determined from the amplitude sweep. From the measurements, the storage (G') and loss (G") moduli and the loss tangent (tan δ) were calculated as a function of the strain. Frequency sweeps were performed by increasing the frequency logarithmically from 0.1 to 10 Hz at a strain amplitude of 0.5%, to keep within the LVE region. The storage (G') and loss (G") moduli and the loss tangent (tan δ) were calculated as a function of the angular frequency. Time sweep flow experiments were conducted with a logarithmic shear rate sweep (0.1-500.0 $s^{-1}$). The shear stress and viscosity were calculated as a function of the shear rate. Thixotropic tests were performed with three oscillation intervals at strain amplitudes of 1%, 70% and 1%, respectively, and a fixed frequency of 1 Hz. Thixotropic time and total recovery time were defined as the intervals between the onset time of the third oscillation interval and the point of time for 95% recovery and full recovery, respectively.

Printing in a pollen gel The supporting bath was prepared using 10 v/v % pollen hydrogels obtained from 6 h-incubation in 10 w/v % KOH solution at 80° C. For 3D printing with alginate inks, 7 w/w % alginate solution (Sigma Aldrich) was prepared with black food ink. The black alginate ink was directly printed in the pollen microgel support bath without physical crosslinking at the feed rate of 6 mm/s and air pressure of 5.5 bar using the regenHU 3D discovery printer. The scaffold was then exposed to UV light for 5 min and incubated at 37° C. to melt and remove the support bath. For 3D printing with polydimethylsiloxane (PDMS), SE1700 inks (Dow Corning, Inc.) were prepared with the composition of white base:catalyst:silicon oil=10:1:1.5 with an orange food dye and then printed at the feed rate of 3-4 mm/s and air pressure of 5.5 bar. The nozzle tips with an inner diameter of 0.33 mm were used for the printing.

Printing with pollen microgel inks The pollen microgel-alginate inks were prepared, varying the ratios of pollen microgels to alginate from 1:0, 2:1, 1:1, 1:2, and 0:1, by mixing 10 v/v % pollen microgels with 7 w/w % alginate. The composite inks were printed at the feed rate of 6 mm/s under various air pressure from 0.5 to 2 bar depending on the ink viscosity. The nozzle tips with an inner diameter of 0.33 mm were used for the printing. For the 3D scaffold of pollen-alginate composites, the gelatin bath was prepared: In brief, gelatin (5% w/v) was dissolved in a 0.01 M $CaCl_2$) solution at 40° C. The solution was then gelled at 4° C. Subsequently, 5 mL of the gelatin gel and 15 mL of the 0.01 M $CaCl_2$) solution was homogenized at 10000 rpm for 1 min. The mixture was centrifuged at 4000 rpm for 2 min and the supernatant was removed to obtain a gelatin slurry support bath. The composite inks with the ratio of microgels to alginate=1:1 were printed at the feed rate of 6 mm/s under various air pressure from 1 bar in the gelatin bath using the nozzle tip with an inner diameter of 0.33 mm. 0.01 M $CaCl_2$) solution was poured into the gelatin bath for the post-curing of composite scaffolds. The scaffolds were removed from the bath and washed using saline solution and distilled water. For UV-curable pollen microgel-hydrogel inks were also prepared by mixing pollen microgels with glycidyl methacrylate hyaluronic acid (GM-HAc). Two types of pollen hydrogels were prepared for UV-curable composite hydrogel inks. The normal pollen microgels were obtained from 6 h-incubation in 10 w/v % KOH solution at 80° C. The Rhodamine B (RhB)-loaded sunflower pollen gel were prepared as follows: 160 μL sunflower pollen gel were dispersed in 0.5 mL of 1 mg/mL RhB solution with the addition of 50 μL of 100 mM EDTA then vortex for 5 min. The mixture was kept at 4° C. for 20 h in the absent light. After 20 h, 50 μL of $CaCl_2$) was added into the RhB-loaded sunflower pollen gel suspension and the pollen gel was separated by centrifuging at 4500 rpm for 5 min then washed by deionized water to get rid of the free RhB. 1 mL of pollen with or without RhB was mixed with 1.5 mL of DI water. Subsequently, 80 mg of GMHA, 10 mg of alginate, 200 μL of N-vinyl-pyrrolidinone (NVP) and 40 mg of Irgacure 2959 was dissolved in the pollen solution to make the ink for 3D printing. The scaffold was then printed in the gelatin slurry support bath at feed rate of 5 mm/s and air pressure of 3 bar using regenHU 3D discovery printer. The scaffold was exposed to UV light for 15 min and then removed from the support bath after incubation at 37° C. for 5 min.

Controlled release study of pollen microgels The Rhodamine B (RhB)-loaded sunflower pollen gel were prepared as follows: 160 μL sunflower pollen gel were dispersed in 0.5 mL of 1 mg/mL RhB solution with the addition of 50 μL of 100 mM EDTA then vortex for 5 min. The mixture was kept at 4° C. for 20 h in the absent light. After 20 h, 50 μL of $CaCl_2$ was added into the RhB-loaded sunflower pollen gel suspension and the pollen gel was separated by centrifuging at 4500 rpm for 5 min then washed by deionized water to get rid of the free RhB. A control group was prepared with the same procedure but without addition of RhB. Loading efficiency were determined using an UV-spectrophotometer (Boeco-S220, Germany) at 558 nm using the following equations:

Loading efficiency (%)=amount of RhB in gel/initial amount of DOX in the system×100

4 mg of DOX-loaded sunflower pollen gel was suspended in 2 mL of deionized water and incubated at 37° C. while stirring at 110 rpm in an orbital shaker incubator (LM-450D, Yihder, Taiwan). At predetermined time points, 0.4 mL of release media was collected and replenished with deionized water. For the experimental group, 200 μL of 100 mM EDTA solution were added in the system at 25 min. A control group was processed with the same procedure but without addition of EDTA at 25 min. The absorbance in the release sample was measured using a UV spectrometer (Boeco-S220, Germany) at 558 nm.

Engineering control of pollen microgel system It was found that pollen can be converted into microgels through well-designed strong alkali treatments which, inter alia, hydrophilize, gelatinize and soften the pectin network of intine. The intine has a bi-layered structure consisting of the granular exintine consisting of pectine and proteins and facing the exterior and the underlying microfibrillar cellulose layer, the endintine, facing the interior of the pollen. The pectin network is known to interact with the cellulose network through both covalent ester linkages and non-covalent hydrogen bonding. Similar to pectinase, the treatment with strong alkali (potassium hydroxide; KOH) at high temperature (80° C.) de-esterifies pectin through an alkaline hydrolysis reaction, increasing water absorption capability due to the resultant gelation. Besides the influence on pectin, strong alkali not only disrupts hydrogen bonding between hemicellulose and cellulose microfibrils or between pectin and cellulose microfibrils, but also degrades pectin and cellulose molecules along with the increased duration of alkali treatment, ultimately leading to softening of intine. As a result, pollen transforms from the close state (or termed as "off") to the open state (or termed as "on") due to opening of apertures which are the weakest spots of the pollen surface, providing the main route for uptake of water and nutrients from the environments and serving as the exit point of a pollen tube.

A sunflower pollen system with a unique trilobite structure where three apertures symmetrically, yet partially divide the spiky pollen shell into three equal parts like a pattern cut was chosen as a model system. The process for the production of sunflower pollen microgels is illustrated in FIG. 17A. Harvested from *Helianthus annuus*, sunflower pollens are defatted with acidic solutions for the removal of lipids and proteins. The defatted sunflower pollen exhibits spiky and nano-porous surface. Then the first alkali treatment using 10 w/v % KOH (1.8 M KOH) solution extracts bi-layered pollen shells at high temperature (80° C.) within short treatment time (2 hr) by removing cytoplasm of the pollen. After cleansing the pollen shells with the same KOH solution, the second alkali treatment with 10 w/v % KOH solution is applied to the extracted pollen shells by varying the incubation time from 0 hour to 12 hours at 80° C., leading to extensive demethylation of pectin (also termed "de-esterification") along with both gelation and degradation. The pH of this pollen can be neutralized (from high pH to pH 7) by washing with deionized water and then centrifuged for increased packing density of the pollen dispersion.

The optical images of pollen dispersion in the glass vials show the gel-like behavior (FIG. 17B). Even though the pollen dispersion is appended, it remains in the original position, instead of flowing downward. This gel-like behavior becomes more prominent as the de-esterification process time increases. The gel matrix and the hollow structure of pollen microgels can be observed in CLSM photos due to the virtue of their auto-fluorescence (FIG. 17B). The 2D scanning images showed the hollow cross-section of the pollen microgels with the presence of green spiky circular rings of the pollen wall and the absence of interior content. More importantly, as opposed to the relatively continuous shell for microgels with 0 hr de-esterification, 3-, 6-, and 12-hr treated microgels clearly exhibit the discrete rings with increased diameters due to opened apertures of the shell, verifying that the microgels are "on" state with opened aperture structures. The pollen wall is also sufficiently strong, maintaining its circular cross-sectional structure without significant collapse. The packing arrangement of pollen spheres was further observed by the z-stack reconstructed photos. Each individual pollen sphere is separated from other surrounding pollen spheres by their own spikes, avoiding direct contact with each other.

Structural characteristics of pollens depending on the treatment conditions were further investigated through the FT-IR analyses (FIG. 17C). Due to the existence of cytoplasm, the FT-IR absorption spectrum of defatted pollen was more complicated and distinctive than those of KOH-treated pollen specimens. Regardless of the different treatment time with strong alkali, the characteristic absorbance peaks of all KOH-treated pollen grains appear almost identical. It was presumed that one of key components, pectin, should be observed through the FT-IR spectra, which has two important characteristic peaks at ~1740 and ~1620 $cm^{-1}$ due to stretching of esterified and de-esterified carboxyl groups (—$COOCH_3$ and —COOH) besides other peaks (1411, 1101, and 1019 $cm^{-1}$) within the fingerprint zone (800-1800 $cm^{-1}$). The peak shift may occur due to the existence of potassium ions and the influence of other cell wall components. All pectin peaks were more clearly observed for KOH-treated pollen grains than defatted pollen. However, up to 12 hr incubation with KOH, no significant structural changes of pollen grains were observed through FT-IR even though the existence of de-esterified carboxyl group for pectin was confirmed. With further extended incubation time up to 90 hrs, it was clearly observed that the peak intensity of the band at ~1600 $cm^{-1}$ was increased with the increased treatment time, implying a higher degree of de-esterification. The existence of de-esterified pectin in the pollen shell was attributed to the formation of pollen microgels. After the KOH treatment, the pollen surface is covered by negative charge due to de-esterified carboxyl groups, and then a combined charge neutralization and ionic strength effect is responsible for the KOH-induced gelation of pollen grains.

Besides de-esterification reaction during the second KOH treatment, the degradation of pectin in addition to the dissociation between pectin and cellulose should take place due to the existence of strong alkali at high temperature, which those reactions likely decrease the mechanical properties of hydrogels contrary to the crosslinking reaction related to de-esterification.

For instance, hemicellulose is known to be solubilized in strong alkali due to the disrupted hydrogen bonding between hemicellulose and cellulose microfibrils. The storage moduli of defatted pollen dispersion are two orders of magnitude larger than those of KOH-treated pollen microgel dispersion (FIG. 17D). Moreover, depending on the incubation time during the second alkali treatment, the further mechanical degradation gradually occurred. Interestingly, after 24 hr incubation, storage moduli of the pollen dispersion appeared slightly increased, compared with those of 12-hr treated pollen. From the FT-IR analyses, 24 hr-treatment increased the de-esterification of pectin, which may lead the enhanced crosslinking density of the gel. Thus, the increased cross-linking density of pollen gels contributed to the enhanced gel stiffness despite the longer alkali treatment associated with material degradation.

It was also confirmed that strong alkali treatment can activate and gelatinize pectin of intine, transforming stiff polymeric pollen to soft pollen microgels. It was known that intine layer was predominantly composed of polysaccharide, such as pectin and cellulose, especially pectin which can undergo gelation in the presence of alkali hydroxide in a concentration-depended manner. To verify gelation of pectin, stimulus-responsive swelling-deswelling behavior of pollen microgels induced by pH or EDTA treatment was evaluated (FIG. 18). The reduced degree of esterification led by ether pectinase or alkali-induced hydrolysis increased the total number of carboxyl groups in the pectin backbone, enhancing the swelling capability of the pectin gels.

First, to investigate the size and morphology of the pollen microgel at different pH conditions in a range of pH 2-14, Dynamic imaging particle analysis (DIPA) experiments were conducted with a Flowcam instrument as shown in FIG. 18. In response to pH change from pH 10 to pH 2, deswelling of 3 h-treated pollen with KOH was clearly observed, decreasing the diameter from 45±3 to 28±2 µm. The pH-responsive swelling/deswelling mechanism of pollen microgels is reversible (FIG. 18A). After increasing pH from 2 to 10, the diameter of the pollen microgel was fully recovered to 45±3 µm. The association or dissociation of hydrogen protons in carboxyl groups influence the repulsion of the neighboring pectin chains in the gel network, governing pH-responsive swelling and deswelling behavior of the pectin gel. The association or dissociation of hydrogen protons influence the repulsion of the neighboring pectin chains in the gel network, governing pH-responsive swelling and deswelling behavior of the pectin gel. The reversibility of pH-sensitivity of the pollen microgel was examined with real-time observation in a modified micro-chamber. FIG. 18B showed the multiple measurement of the diameter of a representative pollen microgel during pH variation from 2 to 14. The result indicated that the pollen microgel showed good reversibility in term of its pH-responsive behavior. Meanwhile, the dynamic of the swelling and shrinking state was examined based on a sequence of video images of the representative pollen microgel. Surprisingly, it only took 3 s to transform the "off" state to the "on" state under the pH 14 buffer at a flow speed of 300 µL/min, and 3 s from the "on" to "off" under the pH 2 buffer at the same flow speed. Based on the knowledge that structure evolution of polyelectrolyte matrix-based microgel is driven by solvent diffusive process, it is assumed that the fast response of pollen microgel to pH variation is attributed to its hollow- and three apertures-structure, which allowed for the fast solvent exchange with the environment. The KOH incubation time also influenced the pH-responsive swelling behavior of pollen microgels (FIG. 18C). The weakened gel network along with the 3-6 hr KOH treatment increased the equilibrium swelling diameter of pollen microgels, maximizing the difference between swelling and deswelling diameter of the gels. However, the further degradation of pectin chains due to longer alkali treatment more than 6 hr eventually reduced the swelling capability of the gel network, due to shorter chain length, decreasing the max swelling diameter by ~10%.

On the other hand, those carboxyl groups of pectin molecules can be physically linked through interaction with divalent cations (e.g., $Ca^{2+}$). By increasing the concentration of calcium ions, the density of crosslinking in the pectin gel can be elevated with the reduced swelling capability. In contrast, with EDTA chelating, the calcium ions can± be removed, decreasing the density of crosslinking with the enhanced swelling behavior. $Ca^{2+}$ was used as an external stimulus to tune the size of 3 h-kOH treated pollen microgels (FIG. 18D). The DIPA data showed the calcium response of pollen microgels in the solution of increasing $CaCl_2$) concentration. The diameter of pollen microgels showed significant decrease from 43±3 to 30±3 µm at 1 mM of $CaCl_2$). The reversibility of $Ca^{2+}$-sensitivity of the pollen microgel was investigated by the same method that was used in the pH responsiveness study (FIG. 18E). Similarly, the sunflower pollen microgel also showed good reversibility after multiple cycles of $Ca^{2+}$ stimuli and EDTA treatment, during which the diameter of pollen microgels repeated changing from 30±3 µm to 43±3 µm. As expected, the large amount of the charge on the inner layer surface enable the fast $Ca^{2+}$-response of pollen microgel due to de-esterified carboxyl groups of pectin. However, the $Ca^{2+}$ responsiveness of pollen microgels is slightly slower (12 s to turn "on" and 12 s to turn "off") than their pH responsiveness, which might due to the lower dissociation rate of $-(COO)_2Ca$. The morphology of the pollen microgels were also affected by the concentration of $Ca^{2+}$: slight shrinkage in 0.1 mM of $CaCl_2$) and strong shrinkage at mM of $CaCl_2$) (FIG. 18F). Interestingly, the $Ca^{2+}$-induced the pollen microgel deformation can be totally recovered by adding EDTA regardless of calcium concentration. Instead, the equilibrium diameter of pollen microgels decrease till the smallest size 28±3 at ≥100 mM of $CaCl_2$). It was also noted that the high $Ca^{2+}$ concentrate (≥10 mM) could lead to aggregation of pollen microgels. $Ca^{2+}$ could play a role as a cross linking agent for the adjacent pollen microgels.

Microgels have been introduced for biomedical applications, has been used as the three-dimension (3D) bioprinting materials due to its useful rheological properties and their jamming behavior. By using this technique, the "ink" material could be injected into the microgel medium and finally trapped in space by packed microgels, which temporarily fluidize under the stress generated by a translating injection tip and then rapidly return to a jammed solid state. In order to precisely control the 3D printing, the proper rheological properties of the microgel medium, such as modulus, yield stress and the period of elastic recovery need to be optimized. Recent studies on hydrophilic Carbopol and hydrophobic polystyrene-polybutadiene-polystyrene (SBS) microgels discovered that viscoplastic granular gel systems with Oldroyd number (Od)<1 and strong thixotropic behavior possess a self-healing capability, providing continuous support to deposited inks during printing. Thus, the rheological behavior of pollen microgel systems regarding viscoplastic behavior, storage modulus and thixotropic time were rigorously assessed for the confirmation of their feasibility as supporting matrices of 3D printed soft matters like Carbopol. Since 6 hr-treated pollen microgels with KOH shows the stable gel behavior with the maximum swellability, they were chosen as a model system. First, to determine the yield stress of pollen microgels, shear stress was measured as a function of shear rate ($\dot{\gamma}$) (FIG. 19A). The pollen microgel dispersion clearly exhibits Bingham plastic behavior. The Herschel-Burkley (H-B) model ($\tau=\tau_0+k\dot{\gamma}^n$) was used to fit the shear stress-shear rate curve, providing the H-B parameters, the yield stress, $\tau_0=\sim3.5$ Pa, the consistency index, k=~6.5 Pa·s and the flow index, n=~0.3 (FIG. 19A). Also measured were stress-dependent storage and loss moduli from oscillatory shear rheometer tests and found the yield stress, by definition, which is the onset shear stress where storage modulus begins decreased and loss modulus increases. The onset stress was ~3 Pa, which is almost identical to the yield stress obtained from the H-B curve fitting. Additionally, yield strain of the microgel pollen system could be determined by strain-dependent storage and loss moduli (FIG. 19B). In this case, the cross-over point of storage and loss moduli, $\gamma^Y=\sim40\%$, where tan δ becomes one and the material starts behaving like a fluid was chosen. Later, the fluid-like behavior of pollen microgel dispersion from the frequency-dependent rheological behavior, at a strain of 40% was further validated.

As a proof-of-concept, 3D printing in the pollen microgel medium using two types of inks—alginate and polydimethylsiloxane (PDMS) as shown in FIGS. 19C and 19D was carried out. Both inks show shear-thinning behavior and have relatively comparable storage moduli (G') to those of pollen microgels. To demonstrate the supportability of the pollen-gel medium during 3D printing, complex printing paths were designed for both inks. Writing a Chinese word, 花粉 (English: Pollen) requires multiple starting points and junctions for the total seventeen strokes of the two letters during printing. Each stroke of the Chinese words with a diameter of 500 μm was drawn in a single pass, either intercepting or adjoining the pre-printed strokes at the optimal printing speed. The un-crosslinked alginate inks were stable during or after printing, being clearly visible even after 3 hrs from the completion of printing (FIG. 19C). Moreover, also used was PDMS ink made of SE1700 which requires high temperature curing at 50-80° C. The meshed dome frame was printed and, subsequently cured at 75° C. for 24 hours inside the gel medium (FIG. 19D). Due to the evaporation of water, the gel medium was dried. However, the printed PDMS dome maintained its original structure without any significant deformation or collapse. Even though a pollen microgel medium has great potential as a supportive matrix for 3D freeform printing, two features should be carefully considered for real applications: visibility of printed objects during printing and recyclability of the microgel systems. The visibility of pollen microgel mediums is ~2 mm from an outer surface. If the demonstration of printability for various printing structures with different ink materials can be done near an outer surface as several test printing cases, 3D printing within the pollen microgels can be easily optimized with minimum trial-and-errors. Regarding recyclability, the pollen gels have great long-term structural stability without any significant agglomeration among adjacent microgels, and maintain their rheological properties at room temperature due to the existence of the outer hydrophobic exine layer with a spiky surface topography. However, high temperature incubation causes degradation of the pectin network, decreasing storage modulus and thixotropic behavior of pollen microgel systems. Increased cross-linking density of pectin may improve thermal stability of the pollen microgels.

Finally, microgels were introduced as additives into various hydrogel inks since the shell structure of pollen microgels allows pollen to be applied as drug carriers. Particularly, the pH or $Ca^{2+}$/EDTA-associated stimulus-responsive behavior of pectin in the microgels provide "smart" functions of pollen microgels. The viscosity of pollen grains is clearly varied with the treatment conditions during the pollen process (FIG. 20A). 10 v/v % defatted pollen exhibit two orders of magnitude larger viscosity than 10 v/v % KOH-treated pollen. The decreased viscosity of pollen microgels can increase the volumetric concentration of pollen in 3D printing inks. For instance, as one of common hydrogel inks, alginate has been applied to various 3D printing systems due to its simple and cell-friendly cross-linking process. Various alginate-pollen composite inks with different volumetric ratios of 0:1, 1:2, 1:1, 2:1 and 1:0 were prepared in order to confirm the viscosity of those inks depending on the composition of inks (FIG. 20B). All composite inks show lower viscosity than pure alginate inks due to the higher water content of pollen microgels. All prepared inks were printable, maintaining their printed structure after the post-treatment using 153 mM $CaCl_2$) solution. The 3D porous scaffold of alginate-pollen composite was successfully fabricated where pollen microgels were well-dispersed within the alginate strut (FIG. 20C). Even though the post-treatment was applied with than higher concentration (>1 mM) of $CaCl_2$) solution, pollen microgels inside alginate did not aggregate with their adjacent neighbors, indicating that the existence of the matrix material avoids aggregate issues of pollen microgels. Unfortunately, pollen microgels themselves cannot be printed alone due to inhomogeneous crosslinking reactions at the interface of pollen microgels, which induce partial consolidation of the pollen microgel building blocks.

Smart pollen microgel carriers were assessed using a fluorescent dye, Rhodamine B. The $Ca^{2+}$/EDTA-associated stimulus-responsive mechanism of pectin was used for EDTA-initiated release of drugs for pollen microgels. First of all, the Rhodamine B-loaded pollen microgels were prepared. To avoid the influence of EDTA to other ink materials, a photo-crosslinkable hyaluronic acid (HAc)/alginate/pollen system was used. Printability of the HAc-based composite inks was good. However, for printing quality, a gelatin granular medium was used for the printing of the HAc-based composite inks. With Rhodamine B-loaded pollen microgels, the printed scaffolds became red due to the passive diffusion of Rhodamine B. The EDTA-responsive release behavior of Rhodamine B-loaded pollen microgels was quantitatively assessed as shown in FIG. 20D. Due to the existence of abundant nanopores in the exine layer of pollen, passive diffusion was clearly observed for normal 'off' samples. Once EDTA is introduced, the pectin network can be swollen, opening the apertures which becomes a main channel of mass transfer. As a result, after EDTA treatment, the release of Rhodamine B was significantly increased. If nanopores in the exine layer can be selectively closed through an additional coating layer on the top of exine layer, the stimulus-responsive release behavior of drugs loaded onto the pollen microgels may be tuned, minimizing uncontrolled release due to passive diffusion.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. A method for formation of microgels of sporoderm polymer complex microcapsules (SPC-MCs), the method comprising the steps of:
   (a) providing pollen comprising pollen grains from eudicot plants;
   (b) deproteinizing the pollen by contacting the pollen with an aqueous base solution at a temperature of 40 to 95° C. for up to 10 hours to obtain porous SPC-MCs; and
   (c) hydrolytically degrading the porous SPC-MCs by contacting the porous SPC-MCs with an aqueous base solution at a temperature of 10 to 30° C. for periods up to 60 days to obtain microgels of the SPC-MCs.

2. The method of claim 1, wherein the pollen is from a flowering plant of the genus *Baccharis, Helianthus* or *Camellia*.

3. The method of claim 1, wherein the pollen is defatted pollen or the method further includes a step of defatting the pollen prior to step (b).

4. The method of claim 1, wherein the aqueous base solution used in step (b) and/or (c) comprises an aqueous alkaline metal hydroxide solution.

5. The method of claim 4, wherein the alkaline metal hydroxide concentration ranges from 0.5 to 40% (w/v).

6. The method of claim 1, wherein step (b) is carried out for a period of 1 to 6 hours.

7. The method of claim 1, wherein step (c) is carried out for 7 to 35 days.

8. The method of claim 1, wherein step (c) further includes a step of neutralizing a suspension of partially degraded SPC-MCs obtained after the hydrolytic degradation by washing the partially degraded SPC-MCs with water until the suspension has a pH in the range of 6.0 to 8.5, to obtain a neutralized microgel solution.

9. The method of claim 1, wherein the microgel obtained is a viscous aqueous gel comprising 1 to 6 wt.-% SPC-MCs and the remainder being water.

10. A method for formation of flexible sheets or sponge structures, comprising the steps of forming microgels of sporoderm polymer complex microcapsules (SPC-MCs) according to claim 1 and further comprising the steps of
   (d) forming a film of the microgel on a substrate and drying the film to obtain a flexible sheet of the SPC-MCs; or
   (e) lyophilizing the microgel to obtain sponge structures of the SPC-MCs.

11. The method of claim 1, wherein the porous SPC-MCs obtained in step (b) are in a suspension comprising the porous SPC-MCs and proteinaceous debris, and the method further comprises mixing the suspension with an aqueous base solution to remove the proteinaceous debris from the porous SPC-MCs.

* * * * *